US011827921B2

(12) United States Patent
Kartalov et al.

(10) Patent No.: US 11,827,921 B2
(45) Date of Patent: *Nov. 28, 2023

(54) SIGNAL ENCODING AND DECODING IN MULTIPLEXED BIOCHEMICAL ASSAYS

(71) Applicant: California Institute of Technology, Pasadena, CA (US)

(72) Inventors: Emil P. Kartalov, Pasadena, CA (US); Aditya Rajagopal, Orange, CA (US); Axel Scherer, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 580 days.

This patent is subject to a terminal disclaimer.

(21) Appl. No.: 16/864,744

(22) Filed: May 1, 2020

(65) Prior Publication Data
US 2021/0098076 A1    Apr. 1, 2021

Related U.S. Application Data

(63) Continuation of application No. 15/914,356, filed on Mar. 7, 2018, now Pat. No. 10,770,170, which is a (Continued)

(51) Int. Cl.
G01N 33/48        (2006.01)
G01N 33/50        (2006.01)
(Continued)

(52) U.S. Cl.
CPC ............. *C12Q 1/6825* (2013.01); *C12Q 1/68* (2013.01); *C12Q 1/6851* (2013.01); (Continued)

(58) Field of Classification Search
CPC ...... C12Q 1/6825; C12Q 1/68; C12Q 1/6851; G01N 21/6486; G06F 17/10; G06F 17/11
See application file for complete search history.

(56) References Cited

U.S. PATENT DOCUMENTS 5,079,351 A    1/1992   Sninsky et al.
5,538,848 A    7/1996   Livak et al.
(Continued)

FOREIGN PATENT DOCUMENTS

CN    1936019 A      3/2007
CN    101570782 A    11/2009
(Continued)

OTHER PUBLICATIONS

Arya, et al., Basic principles of real-time quantitative PCR, 2005, Expert Rev. Mol. Diagn., 5(2), p. 209-219.
(Continued)

*Primary Examiner* — Russell S Negin
(74) *Attorney, Agent, or Firm* — Sheppard Mullin Richter & Hampton LLP

(57) ABSTRACT

This disclosure provides methods, systems, compositions, and kits for the multiplexed detection of a plurality of analytes in a sample. In some examples, this disclosure provides methods, systems, compositions, and kits wherein multiple analytes may be detected in a single sample volume by acquiring a cumulative measurement or measurements of at least one quantifiable component of a signal. In some cases, additional components of a signal, or additional signals (or components thereof) are also quantified. Each signal or component of a signal may be used to construct a coding scheme which can then be used to determine the presence or absence of any analyte.

19 Claims, 8 Drawing Sheets

Specification includes a Sequence Listing.

Related U.S. Application Data continuation of application No. 14/451,876, filed on Aug. 5, 2014, now Pat. No. 10,068,051, which is a continuation of application No. 13/756,760, filed on Feb. 1, 2013, now Pat. No. 8,838,394.

(60) Provisional application No. 61/703,093, filed on Sep. 19, 2012, provisional application No. 61/594,480, filed on Feb. 3, 2012.

(51) Int. Cl.

| | | |
|---|---|---|
| *C12Q 1/6825* | (2018.01) | |
| *G16B 25/00* | (2019.01) | |
| *G16B 5/00* | (2019.01) | |
| *C12Q 1/6851* | (2018.01) | |
| *G16B 25/20* | (2019.01) | |
| *G16B 40/10* | (2019.01) | |
| *C12Q 1/68* | (2018.01) | |
| *G01N 21/64* | (2006.01) | |
| *G06F 17/10* | (2006.01) | |
| *G06F 17/11* | (2006.01) | |
| *G16B 40/00* | (2019.01) | |

(52) U.S. Cl.
CPC .......... *G01N 21/6486* (2013.01); *G16B 5/00* (2019.02); *G16B 25/00* (2019.02); *G16B 25/20* (2019.02); *G16B 40/10* (2019.02); *G06F 17/10* (2013.01); *G06F 17/11* (2013.01); *G16B 40/00* (2019.02); *Y02A 50/30* (2018.01)

(56) References Cited

U.S. PATENT DOCUMENTS

| | | |
|---|---|---|
| 5,618,711 A | 4/1997 | Gelfand et al. |
| 5,677,152 A | 10/1997 | Birch et al. |
| 5,723,591 A | 3/1998 | Livak et al. |
| 5,773,258 A | 6/1998 | Birch et al. |
| 5,789,224 A | 8/1998 | Gelfand et al. |
| 5,804,375 A | 9/1998 | Gelfand et al. |
| 5,834,203 A | 11/1998 | Katzir et al. |
| 5,876,930 A | 3/1999 | Livak et al. |
| 5,882,856 A | 3/1999 | Shuber |
| 5,928,862 A | 7/1999 | Morrison |
| 5,948,360 A | 9/1999 | Rao et al. |
| 5,981,180 A | 11/1999 | Chandler et al. |
| 5,994,056 A | 11/1999 | Higuchi |
| 6,030,787 A | 2/2000 | Livak et al. |
| 6,103,463 A | 8/2000 | Chetverin et al. |
| 6,127,155 A | 10/2000 | Gelfand et al. |
| 6,171,785 B1 | 1/2001 | Higuchi |
| 6,258,569 B1 | 7/2001 | Livak et al. |
| 6,534,266 B1 | 3/2003 | Singer |
| 6,534,274 B2 | 3/2003 | Becker et al. |
| 6,548,259 B2 | 4/2003 | Ward et al. |
| 6,642,062 B2 | 11/2003 | Kauvar et al. |
| 6,893,875 B2 | 5/2005 | Tsuji et al. |
| 7,101,663 B2 | 9/2006 | Godfrey et al. |
| 7,141,377 B2 | 11/2006 | Gelfand et al. |
| 7,348,141 B2 | 3/2008 | French et al. |
| 7,385,043 B1 | 6/2008 | Kramer |
| 7,410,764 B2 | 8/2008 | Gocke et al. |
| 7,413,708 B2 | 8/2008 | Mayrand |
| 7,473,767 B2 | 1/2009 | Dimitrov |
| 7,507,575 B2 | 3/2009 | Bedingham et al. |
| 7,575,864 B2 | 8/2009 | Bedzyk et al. |
| 7,667,024 B2 | 2/2010 | Mao et al. |
| 7,671,184 B2 | 3/2010 | Haener et al. |
| 7,709,249 B2 | 5/2010 | Bedingham et al. |
| 7,767,423 B2 | 8/2010 | Kopreski et al. |
| 7,771,949 B2 | 8/2010 | Kramer |
| 7,919,237 B2 | 4/2011 | Dimitrov et al. |
| 7,919,244 B2 | 4/2011 | Madejon et al. |
| 7,930,106 B2 | 4/2011 | Carrick et al. |
| 7,941,279 B2 | 5/2011 | Hwang et al. |
| 8,039,215 B2 | 10/2011 | Higuchi et al. |
| 8,148,512 B2 | 4/2012 | Dimitrov et al. |
| 8,426,132 B2 | 4/2013 | Li et al. |
| 8,455,184 B2 | 6/2013 | Atchley et al. |
| 8,492,094 B2 | 7/2013 | Dimitrov et al. |
| 8,519,115 B2 | 8/2013 | Webster et al. |
| 8,614,061 B2 | 12/2013 | Brabetz et al. |
| 8,771,955 B2 | 7/2014 | Reed et al. |
| 8,838,394 B2 | 9/2014 | Kartalov et al. |
| 8,877,464 B2 | 11/2014 | Babiel et al. |
| 8,962,250 B2 | 2/2015 | Stanley et al. |
| 9,133,506 B2 | 9/2015 | Katzir et al. |
| 9,222,128 B2 | 12/2015 | Saxonov et al. |
| 9,260,761 B2 | 2/2016 | Tyagi et al. |
| 9,366,632 B2 | 6/2016 | Link et al. |
| 9,422,593 B2 | 8/2016 | Rothmann et al. |
| 9,441,266 B2 | 9/2016 | Larson et al. |
| 9,447,457 B2 | 9/2016 | Chun et al. |
| 9,458,497 B2 | 10/2016 | Hassibi et al. |
| 9,791,372 B2 | 10/2017 | Malik et al. |
| 10,066,263 B2 | 9/2018 | Rajagopal et al. |
| 10,068,051 B2 | 9/2018 | Kartalov et al. |
| 10,301,668 B2 | 5/2019 | Jacky |
| 10,770,170 B2 | 9/2020 | Kartalov et al. |
| 2002/0022273 A1 | 2/2002 | Empedocles et al. |
| 2002/0146734 A1 | 10/2002 | Ortyn et al. |
| 2003/0134320 A1 | 7/2003 | Barrus et al. |
| 2003/0148280 A1 | 8/2003 | Harris et al. |
| 2003/0148544 A1 | 8/2003 | Nie et al. |
| 2004/0053230 A1 | 3/2004 | Schaffer et al. |
| 2004/0191794 A1 | 9/2004 | Weindel et al. |
| 2004/0248082 A1 | 12/2004 | Scallon |
| 2005/0053950 A1 | 3/2005 | Zudaire Ubani et al. |
| 2005/0064435 A1 | 3/2005 | Su et al. |
| 2005/0106607 A1 | 5/2005 | Yin et al. |
| 2005/0164264 A1 | 7/2005 | Shipwash |
| 2005/0214753 A1 | 9/2005 | Shultz et al. |
| 2005/0250146 A1 | 11/2005 | McMillan |
| 2005/0260640 A1 | 11/2005 | Andersen et al. |
| 2006/0039918 A1* | 2/2006 | Albani ............... A61P 25/00 424/185.1 |
| 2006/0216708 A1 | 9/2006 | Venema |
| 2007/0072211 A1 | 3/2007 | Newton et al. |
| 2007/0178485 A1 | 8/2007 | El-Deiry et al. |
| 2007/0231824 A1 | 10/2007 | Chee et al. |
| 2008/0050737 A1 | 2/2008 | Arieli et al. |
| 2008/0069733 A1 | 3/2008 | Maltezos et al. |
| 2008/0096767 A1 | 4/2008 | Kohn |
| 2008/0124705 A1 | 5/2008 | Kramer |
| 2009/0042735 A1 | 2/2009 | Blair et al. |
| 2009/0048785 A1 | 2/2009 | Katzir et al. |
| 2009/0062129 A1 | 3/2009 | McKernan et al. |
| 2010/0015607 A1 | 1/2010 | Geiss et al. |
| 2010/0041092 A1 | 2/2010 | Lin et al. |
| 2010/0047924 A1 | 2/2010 | Webster et al. |
| 2010/0112710 A1 | 5/2010 | Geiss et al. |
| 2010/0120043 A1 | 5/2010 | Sood et al. |
| 2010/0151443 A1 | 6/2010 | Xiang et al. |
| 2010/0159447 A1 | 6/2010 | Li et al. |
| 2010/0210472 A1 | 8/2010 | Empedocles et al. |
| 2010/0233686 A1 | 9/2010 | Higuchi et al. |
| 2010/0248257 A1 | 9/2010 | Jacobsen et al. |
| 2010/0261026 A1 | 10/2010 | Ferree et al. |
| 2010/0267064 A1 | 10/2010 | Kartalov et al. |
| 2010/0273173 A1 | 10/2010 | Hirai et al. |
| 2010/0317005 A1* | 12/2010 | Hardin ............... C12Q 1/6869 435/6.14 |
| 2010/0324834 A1 | 12/2010 | Treptow et al. |
| 2011/0104684 A1 | 5/2011 | Hooper |
| 2011/0151459 A1 | 6/2011 | Rothmann et al. |
| 2011/0151550 A1 | 6/2011 | Sagner et al. |
| 2011/0171658 A1 | 7/2011 | Carrick |
| 2011/0183884 A1 | 7/2011 | Miller et al. |
| 2011/0207623 A1 | 8/2011 | Dimitrov et al. |
| 2011/0223602 A1 | 9/2011 | Whitman et al. |
| 2011/0237459 A1 | 9/2011 | Nova et al. |
| 2012/0003646 A1 | 1/2012 | Joo et al. |
| 2012/0040349 A1 | 2/2012 | Von Lode et al. |

(56) References Cited

U.S. PATENT DOCUMENTS

| | | |
|---|---|---|
| 2012/0040352 A1 | 2/2012 | Wangh et al. |
| 2012/0045756 A1 | 2/2012 | Rothmann et al. |
| 2012/0077195 A1 | 3/2012 | Li et al. |
| 2012/0101740 A1 | 4/2012 | Orpana et al. |
| 2012/0122704 A1 | 5/2012 | Atchley et al. |
| 2012/0141995 A1 | 6/2012 | Li et al. |
| 2012/0171677 A1 | 7/2012 | Ludowise |
| 2012/0184017 A1 | 7/2012 | Chatterjee |
| 2012/0190030 A1 | 7/2012 | Chun et al. |
| 2012/0196283 A1 | 8/2012 | Babiel et al. |
| 2012/0244534 A1 | 9/2012 | Ching et al. |
| 2012/0252014 A1 | 10/2012 | Loeffert et al. |
| 2012/0252017 A1 | 10/2012 | Reed et al. |
| 2012/0258457 A1 | 10/2012 | Jarosch et al. |
| 2012/0302448 A1 | 11/2012 | Hutchison et al. |
| 2013/0017971 A1 | 1/2013 | Geiss et al. |
| 2013/0040841 A1 | 2/2013 | Saxonov et al. |
| 2013/0078626 A1 | 3/2013 | Wasserstrom et al. |
| 2013/0116780 A1 | 5/2013 | Miller et al. |
| 2013/0261019 A1 | 10/2013 | Lin et al. |
| 2013/0288244 A1 | 10/2013 | Deciu et al. |
| 2014/0004520 A1 | 1/2014 | Mohapatra et al. |
| 2014/0038195 A1 | 2/2014 | Malik et al. |
| 2014/0171341 A1 | 6/2014 | Jouvenot et al. |
| 2014/0213471 A1 | 7/2014 | Rajagopal et al. |
| 2014/0274774 A1 | 9/2014 | Li et al. |
| 2015/0057178 A1 | 2/2015 | Kartalov et al. |
| 2015/0140554 A1 | 5/2015 | Snyder et al. |
| 2015/0211054 A1 | 7/2015 | Kostem et al. |
| 2015/0275295 A1 | 10/2015 | Wang et al. |
| 2016/0040256 A1 | 2/2016 | Chen et al. |
| 2016/0108464 A1 | 4/2016 | Saxonov et al. |
| 2016/0201122 A1 | 7/2016 | Bushkin et al. |
| 2016/0273048 A1 | 9/2016 | Roperch |
| 2017/0145490 A1 | 5/2017 | Chiu et al. |
| 2017/0314073 A1 | 11/2017 | Grömminger et al. |
| 2017/0362636 A1 | 12/2017 | Rajagopal et al. |
| 2018/0030551 A1 | 2/2018 | Rajagopal et al. |
| 2018/0052110 A1 | 2/2018 | Malik et al. |
| 2018/0057864 A1 | 3/2018 | Jacky et al. |
| 2019/0002963 A1 | 1/2019 | Rajagopal |
| 2019/0032112 A1 | 1/2019 | Rajagopal et al. |
| 2019/0112636 A1 | 4/2019 | Rajagopal et al. |
| 2019/0233882 A1 | 8/2019 | Jacky et al. |
| 2020/0010876 A1 | 1/2020 | MacDonald |

FOREIGN PATENT DOCUMENTS

| | | |
|---|---|---|
| EP | 0519338 A1 | 12/1992 |
| EP | 1448581 B1 | 11/2008 |
| EP | 2224017 A1 | 9/2010 |
| EP | 1963531 B1 | 9/2011 |
| EP | 1629108 B1 | 12/2014 |
| WO | WO-9746714 A1 | 12/1997 |
| WO | WO-9919515 A1 | 4/1999 |
| WO | WO-99/52708 | 10/1999 |
| WO | WO-0107640 A2 | 2/2001 |
| WO | WO-02056014 A2 | 7/2002 |
| WO | WO-03002979 A2 | 1/2003 |
| WO | WO-03020967 A1 | 3/2003 |
| WO | WO-02056014 A3 | 10/2003 |
| WO | WO-2004087950 A2 | 10/2004 |
| WO | WO-2006079049 A2 | 7/2006 |
| WO | WO-2007076128 A2 | 7/2007 |
| WO | WO-2007076129 A2 | 7/2007 |
| WO | WO-2007076132 A2 | 7/2007 |
| WO | WO-2007076132 A3 | 9/2007 |
| WO | WO-2007076128 A3 | 11/2007 |
| WO | WO-2007139766 A2 | 12/2007 |
| WO | WO-2007076129 A3 | 3/2008 |
| WO | WO-2008118998 A2 | 10/2008 |
| WO | WO-2008124847 A2 | 10/2008 |
| WO | WO-2007139766 A3 | 12/2008 |
| WO | WO-2008124847 A3 | 2/2009 |
| WO | WO-2009036514 A2 | 3/2009 |
| WO | WO-2010007355 A1 | 1/2010 |
| WO | WO-2010013017 A1 | 2/2010 |
| WO | WO-2010017543 A1 | 2/2010 |
| WO | WO-2010019826 A1 | 2/2010 |
| WO | WO-2010128206 A1 | 11/2010 |
| WO | WO-2011047087 A2 | 4/2011 |
| WO | WO-2011047087 A3 | 8/2011 |
| WO | WO-2011100541 A2 | 8/2011 |
| WO | WO-2011116088 A2 | 9/2011 |
| WO | WO-2011100541 A3 | 1/2012 |
| WO | WO-2011116088 A3 | 2/2012 |
| WO | WO-2012058638 A2 | 5/2012 |
| WO | WO-2012106428 A2 | 8/2012 |
| WO | WO-2012135340 A2 | 10/2012 |
| WO | WO-2012058638 A3 | 12/2012 |
| WO | WO-2012135340 A3 | 12/2012 |
| WO | WO-2013096851 A1 | 6/2013 |
| WO | WO-2013116780 A1 | 8/2013 |
| WO | WO-2014022827 A1 | 2/2014 |
| WO | WO-2014116884 A1 | 7/2014 |
| WO | WO-2015147370 A1 | 10/2015 |
| WO | WO-2016154600 A1 | 9/2016 |
| WO | WO-2017139354 A1 | 8/2017 |
| WO | WO-2017173035 A1 | 10/2017 |
| WO | WO-2017218777 A1 | 12/2017 |
| WO | WO-2018081178 A1 | 5/2018 |
| WO | WO-2019006023 A1 | 1/2019 |
| WO | WO-2019079204 A1 | 4/2019 |
| WO | WO-2019169043 A1 | 9/2019 |

OTHER PUBLICATIONS

Beige, et al. Clinical evaluation of a *Mycobacterium tuberculosis* PCR assay. J Clin Microbiol. Jan. 1995;33(1):90-5.

Blacket et al. Universal primers for fluorescent labeling of PCR fragments—an efficient and cost-effective approach to genotyping by fluorescence. Moleular Ecology Resources 12(3):456-463 (2012) Epub Jan. 24, 2012.

Chamberlain, et al. Deletion screening of the Duchenne muscular dystrophy locus via multiplex DNA amplification. Nucleic Acids Res. Dec. 9, 1988;16(23):11141-56.

Chapin et al., Rapid microRNA profiling on encoded gel microparticles. Angewandte Chemie International Edition, 50(10):2289-2293, 2011.

Chen, et al. A Homogeneous, ligase-mediated DNA diagnostic test. Genome Research, 1998, vol. 8, pp. 549-556.

Chong, et al. Single-tube multiplex-PCR screen for common deletional determinants of alpha- thalassemia. Blood. Jan. 1, 2000;95(1):360-2.

Chromatogram, 2011, 2 pages. Dorland's illustrated medical dictionary. Retrieved online on Jan. 22, 2014 from «http://www.credoreference.com».

Chun et al. Dual priming oligonucleotide system for the multiplex detection of respiratory viruses and SNP genotyping of CYP2C19 gene. Nucleic Acids Res. 35(6):e40 (2007).

Craig, et al. Ordering of cosmid clones covering Herpes simplex virus type I (HSV-I) genome: a test case for fingerprinting by hybridisation. Nucleic Acids Research, 1990, vol. 18, pp. 2653-2660.

Dos Santos, et al. A simple one-step real-time RT-PCR for diagnosis of dengue virus infection. J Med Virol. Aug. 2008;80(8):1426-33.

El-Hajj, et al. Detection of rifampin resistance in *Mycobacterium tuberculosis* in a single tube with molecular beacons. J Clin Microbiol. Nov. 2001;39(11):4131-7.

EMBL-Bank: AJ303204. http://www.ebi.ac.uk/Tools/dbfetch/emblfetch?db=embl&id=AJ303204&format=default&style=default&Retrieve=Retrieve. Accessed Feb. 2012.

EMBL-Bank: GQ395623. http://www.ebi.ac.uk/Tools/dbfetch/emblfetch?db=embl&id=GQ395623&format=default&style=default&Retrieve=Retrieve. Accessed Feb. 2012.

EP17814096.8 Extended European Search Report dated Dec. 2, 2019.

European Office Action for Patent Application No. EP13824744.0 dated Nov. 6, 2018.

(56) References Cited

OTHER PUBLICATIONS

European Patnet Application No. 17776626 Office Action dated Oct. 18, 2019.
Evans et al. Digital PCR for Noninvasive Detection of Aneuploidy: Power Analysis Equations for Feasibility. Fetal Diagn. Ther. 31:244-247(2012).
Extended European Search Report for Patent Application No. 13744261.2 dated May 3, 2016.
Extended European Search Report for Patent Application No. EP13824744.0 dated Feb. 26, 2016.
Fodor, et al. Multiplexed biochemical assays with biological chips. Nature. Aug. 5, 1993;364(6437):555-6.
Fortina, et al. Digital mRNA profiling. Nat Biotechnol. Mar. 2008;26(3):293-4.
Fu et al. Multiplex detection and SNP genotyping in a single fluorescence channel. PLoS One 7(1):Article No. e30340 (Jan. 2012).
Gandelman, et al., Novel Bioluminescent Quantitative Detection of Nucleic Acid Amplification in Real-Time, PLoS One, 2010, 5(11):e14155, 14 pages.
GenBank: M93130.1. Dengue type 3 virus complete genome RNA, complete cds. http://www.ncbi.nlm.nih.gov/nuccore/M93130. Accessed Feb. 2012.
Han, et al., Quantum-dot-tagged microbeads for multiplexed optical coding of biomolecules. Nature Biotechnology 19.99 (Jul. 2001): 631-635.
Hartman, et al. Development of a novel internal positive control for Taqman based assays. Mol Cell Probes. Feb. 2005;19(1):51-9. Epub Dec. 10, 2004.
Haustein et al. Fluorescence correlation spectroscopy: novel variations of an established technique. Ann Rev Biophys Biomol Struct 36:151-69 (2007).
Heidari, et al. Detection of Plasmodium falciparum Directly from Blood Samples Using the Polymerase Chain Reaction. Journal of Sciences, Islamic Republic of Iran. 2005 16(1):21-24.
Henegariu, et al. Multiplex PCR: critical parameters and step-by-step protocol. Biotechniques. Sep. 1997;23(3):504-11.
HIV databases. http://www.hiv.lanl.gov/content/index. Accessed Feb. 2012.
Holland, et al., Detection of specific polymerase chain reaction product by utilizing the 5' to 3' exonuclease activity of Thermus aquaticus DNA polymerase. PNAS (USA) 88:7276-7280, 1991.
Horejsh, et al. A molecular beacon, bead-based assay for the detection of nucleic acids by flow cytometry. Nucleic Acids Res. Jan. 19, 2005;33(2):e13.
Huang, et al. Identification of 8 foodborne pathogens by multicolor combinational probe coding technology in a single real-time PCR. Clin Chem. Oct. 2007;53(10):1741-8. Epub Aug. 10, 2007.
Huang, et al. Multicolor combinatorial probe coding for real-time PCR. PLoS One. Jan. 14, 2011;6(1):e16033.
Hudecova, I. et al. Maternal Plasma Fetal DNA Fractions in Pregnancies with Low and High Risks for Fetal Chromosomal Aneuploidies. PLoS One 9(2):e88484 (2014).
International Search Report and Written Opinion dated Nov. 21, 19 for PCT/US2019/050050.
Jothikumar, et al. Design of FRET-TaqMan probes for multiplex real-time PCR using an internal positive control. Biotechniques. Jun. 2009;46(7):519-24.
Klostranec et al., Convergence of quantum dot barcodes with microfluidics and signal processing for multiplexed high-throughput infectious disease diagnostics. Nano Letters, 7(9):2812-2818, 2007.
Kuhn et al. Hybridization of DNA and PNA molecular beacons to single-stranded and double-stranded DNA targets. J Am Chem Soc. 124(6):1097-103 (2002).
Lao, et al. Multiplexing RT-PCR for the detection of multiple miRNA species in small samples. Biochem Biophys Res Commun. Apr. 28, 2006;343(1):85-9. Epub Feb. 28, 2006.
Lee, et al. Novel multiplex PCR using dual-priming oligonucleotides for detection and discrimination of the *Mycobacterium tuberculosis* complex and M. bovis Bcg. J Clin Microbiol. Dec. 2010;48(12):4612-4. Epub Oct. 13, 2010.
Lee, et al. Seven-color, homogeneous detection of six PCR products. Biotechniques. Aug. 1999;27(2):342-9.
Li et al., Multiplexed detection of pathogen DNA with DNA-based fluorescence nanobarcodes. Nature Biotechnology, 23(7):885-889, 2005.
Liew, et al. Validating a custom multiplex ELISA against individual commercial immunoassays using clinical samples. Biotechniques. Mar. 2007;42(3):327-8, 330-3.
Lin et al., Self-assembled combinatorial encoding nanoarrays for multiplexed biosensing. Nano Letters, 7(2):507-512, 2007.
Livak, et al. Oligonucleotides with fluorescent dyes at opposite ends provide a quenched probe system useful for detecting PCR product and nucleic acid hybridization. PCR Methods Appl. Jun. 1995;4(6):357-62.
Loftis et al., Principles of real-time PCR. Veterinary PCR Diagnostics pp. 3-17 (2012).
Logan, et al., An Overview of real-time PCR platforms. 2004, in Real-time PCR: An essential guide, p. 13-30.
Morgan et al., A commercial line probe assay for the rapid detection of rifampicin resistance in *Mycobacterium tuberculosis*: a systematic review and meta-analysis. BMC Infectious Diseases. 5:62 doi:10.1186/1471-2334-5-62 (2005).
Morrison, et al. Two-color ratio-coding of chromosome targets in fluorescence in situ hybridization: quantitative analysis and reproducibility. Cytometry. Apr. 1, 1997;27(4):314-26.
Myers et al., A Handheld Point-of-Care Genomic Diagnostic System. PLoS One 8(8): e70266; pp. 1-9 (2013).
Navarro et al., Real-time PCR detection chemistry. Clin Chim Acta. 439:231-250 (2015).
Noordhoek, et al. Sensitivity and specificity of PCR for detection of *Mycobacterium tuberculosis*: a blind comparison study among seven laboratories. J Clin Microbiol. Feb. 1994;32(2):277-84.
Oliveira, et al. Multiplex PCR strategy for rapid identification of structural types and variants of the mec element in methicillin-resistant *Staphylococcus aureus*. Antimicrob Agents Chemother. Jul. 2002;46(7):2155-61.
Ou, et al. DNA amplification for direct detection of HIV-1 in DNA of peripheral blood mononuclear cells. Science. Jan. 15, 1988;239(4837):295-7.
Paton, et al. Detection and characterization of Shiga toxigenic *Escherichia coli* by using multiplex PCR assays for stx1, stx2, eaeA, enterohemorrhagic *E. coli* hlyA, rfbO111, and rfbO157. J Clin Microbiol. Feb. 1998;36(2):598-602.
Patterson, et al. Detection of HIV-1 DNA and messenger RNA in individual cells by PCR-driven in situ hybridization and flow cytometry. Science. May 14, 1993;260(5110):976-9.
PCT/US19/40392 International Search Report and Written Opinion dated Nov. 6, 2019.
PCT/US2013/024509 International search report and written opinion dated Apr. 12, 2013.
PCT/US2013/053512 International Search Report and Written Opinion dated Oct. 16, 2013.
PCT/US2017/24933 International search report and written report dated Jun. 22, 2017.
PCT/US2017/37682 International Search Report and Written Opinion dated Nov. 16, 2017.
PCT/US2018/039846 International Preliminary Report on Patentability dated Dec. 31, 2019.
PCT/US2018/055927 International Preliminary Report on Patentability dated Apr. 21, 2020.
PCT/US2018/39846 International Search Report and Written Opinion Mailed Sep. 14, 2018.
PCT/US2019/019906 International Preliminary Report on Patentability Sep. 1, 2020.
PCT/US2019/019906 International Search Report and Written Opinion dated May 6, 2019.
PCT/US2019/027751 International Preliminary Report on Patentability dated Oct. 20, 2020.
PCT/US2019/027751 International Search Report and Written Opinion dated Jun. 26, 2019.

(56) References Cited

OTHER PUBLICATIONS

PCT/US2019/035129 International Search Report and Written Opinion dated Nov. 1, 2019.
PCT/US2019/035129 Invitation to Pay Additional Fees dated Aug. 19, 2019.
PCT/US2019/040392 International Preliminary Report on Patentability dated Jan. 5, 2021.
PCT/US2019/041239 International Preliminary Report on Patentability dated Jan. 21, 2021.
PCT/US2019/041239 International Search Report and Written Opinion dated Sep. 30, 2019.
Petersen, et al. Short PNA molecular beacons for real-time PCR allelic discrimination of single nucleotide polymorphisms. Mol Cell Probes. Apr. 2004;18(2):117-22.
Pierce, et al. Linear-After-The-Exponential (LATE)-PCR: primer design criteria for high yields of specific single-stranded DNA and improved real-time detection. Proc Natl Acad Sci U S A. Jun. 14, 2005;102(24):8609-14. Epub Jun. 3, 2005.
Plasmodium falciparum (Plasmodium falciparum) Genome Browser Gateway. http://microbes.ucsc.edu/cgi-bin/hgGateway?hgsid=612764&clade=eukaryota-protista&org=0&db=0. Accessed Feb. 2012.
Ptak, et al. Inhibition of human immunodeficiency virus type 1 replication in human cells by Debio-025, a novel cyclophilin binding agent. Antimicrob Agents Chemother. Apr. 2008;52(4):1302-17. Epub Jan. 22, 2008.
Rajagopal et al. Supercolor Coding Methods for Large-Scale Multiplexing of Biochemical Assays. Analytical Chemistry 85:7629-7636 (2013).
Rajagopal et al., Significant Expansion of Real-Time PCR Multiplexing with Traditional Chemistries using Amplitude Modulation. Scientific Reports. 9(1): 1053 (2019).
Rickert et al., "Multiplexed Real-Time PCR Using Universal Reporters," Clin. Chem., 50(9):1680- 1683, 2004.
Rosenstraus, et al. An internal control for routine diagnostic PCR: design, properties, and effect on clinical performance. J Clin Microbiol. Jan. 1998;36(1):191-7.
Roth, et al. Feasibility and efficacy of routine PCR screening of blood donations for hepatitis C virus, hepatitis B virus, and HIV-1 in a blood-bank setting. Lancet. Jan. 30, 1999;353(9150):359-63.
Saiki, et al. Primer-directed enzymatic amplification of DNA with a thermostable DNA polymerase. Science, 239(4839):487-491 (Jan. 29, 1988).
Sambrook, et al. Molecular Cloning: A Laboratory Manual. 2nd Edition, 1989.
Sanger et al. DNA sequencing with chain-terminating inhibitors. PNAS USA Dec. 1977;74(12):5463-7 (1977).
Second Office Action for Chinese Patent Application No. 201380049844.9 dated Sep. 19, 2016 (w/translation).
Speicher, et al. Karyotyping human chromosomes by combinatorial multi-fluor FISH. Nat Genet. Apr. 1996;12(4):368-75.
ThermoFisher Scientific Fluorescence SpectraViewer. Retrieved from http://www.thermofisher.com/us/en/home/life-science/cell-analysis/labeling-chemistry/fluorescence-spectraviewer.html on Sep. 25, 2015.
Tirasophon, et al. A novel detection of a single Plasmodium falciparum in infected blood. Biochem Biophys Res Commun. Feb. 28, 1991;175(1):179-84.
Tyagi, et al. Multicolor molecular beacons for allele discrimination. Nat Biotechnol. Jan. 1998; 16(1):49-53.
Tyagi, et al. Wavelength-shifting molecular beacons. Nat Biotechnol. Nov. 2000;18(11):1191-6.
U.S. Appl. No. 16/128,343 Final Office Action dated Mar. 16, 2021.
Urdea, et al. Requirements for high impact diagnostics in the developing world. Nature. Nov. 23, 2006;444 Suppl 1:73-9.
U.S. Appl. No. 13/756,760 Notice of allowance dated Jun. 2, 2014.
U.S. Appl. No. 13/756,760 Office action dated Jan. 24, 2014.
U.S. Appl. No. 13/958,479 Office Action dated Mar. 1, 2016.
U.S. Appl. No. 14/451,876 Office action dated Jun. 6, 2017.
U.S. Appl. No. 14/451,876 Office action dated Nov. 23, 2016.
U.S. Appl. No. 15/623,974 Notice of Allowance dated Jul. 3, 2018.
U.S. Appl. No. 15/623,974 Office Action dated Feb. 22, 2018.
U.S. Appl. No. 15/677,772 Final Office Action Mailed Jun. 7, 2018.
U.S. Appl. No. 15/677,772 Non-Final Office Action Mailed Feb. 8, 2018.
U.S. Appl. No. 15/892,245 First Action Interview—Office Action dated Jul. 19, 2018.
U.S. Appl. No. 15/892,245 Office Action dated Dec. 31, 2018.
U.S. Appl. No. 15/892,245 Preinterview First Interview Office Action dated May 11, 2018.
U.S. Appl. No. 16/020,673 Non-Final Office Action dated Nov. 27, 2020.
U.S. Appl. No. 14/451,876 Notice of Allowance dated Jul. 11, 2018.
U.S. Appl. No. 14/451,876 Notice of Allowance dated Jun. 14, 2018.
U.S. Appl. No. 15/892,245 Office Action dated Dec. 11, 2019.
U.S. Appl. No. 15/892,245 Office Action dated Jun. 17, 2019.
U.S. Appl. No. 16/128,343 Non-Final Office Action dated Jun. 16, 2020.
U.S. Appl. No. 16/128,343 Office Action dated Oct. 15, 2019.
U.S. Appl. No. 15/701,014 Office Action dated Jan. 24, 2020.
U.S. Appl. No. 15/914,356 Office Action dated Jul. 22, 2019.
U.S. Appl. No. 15/914,356 Office Action dated Mar. 8, 2019.
U.S. Appl. No. 16/051,736 Office Action dated Aug. 21, 2020.
U.S. Appl. No. 16/128,343 First Action Interview dated Apr. 18, 2019.
Vet, et al. Multiplex detection of four pathogenic retroviruses using molecular beacons. Proc Natl Acad Sci U S A. May 25, 1999;96(11):6394-9.
Vogelstein, et al., Digital PCR, PNAS Aug. 3, 1999 96 (16) 9236-9241; https://doi.org/10.1073/pnas.96.16.9236.
Wang, et al. Locked nucleic acid molecular beacons. J Am Chem Soc. Nov. 16, 2005;127(45):15664-5.
Waters, et al. Microchip device for cell lysis, multiplex PCR amplification, and electrophoretic sizing. Anal Chem. Jan. 1, 1998;70(1):158-62.
Weidmann, et al. Rapid detection of herpes simplex virus and varicella-zoster virus infections by real-time PCR. J Clin Microbiol. Apr. 2003;41(4):1565-8.
Wiese, et al. Simultaneous multianalyte ELISA performed on a microarray platform. Clin Chem. Aug. 2001;47(8):1451-7.
Xu et al., Multiplexed SNP genotyping using the Qbead system: a quantum dot-encoded microspere-based assay. Nucleic Acids Research, 31(8):e43, 2003.
Yang, L. et al. A novel universal real-time PCR system using the attached universal duplex probes for quantitative analysis of nucleic acids. BMC Molecular Biology, 9:54 (1-13) Jun. 4, 2008.
Zhang, et al. A novel real-time quantitative PCR method using attached universal template probe. Nucleic Acids Res. Oct. 12, 2003;31(20):e123(pp. 1-8).
Zhang, et al. Novel Multiplex PCR Assay for Characterization and Concomitant Subtyping of *Staphylococcal cassette* Chromosome mec Types I to V in Methicillin-Resistant *Staphylococcus aureus*. J Clin Microbiol. Oct. 2005;43(10):5026-33.
Zhao et al. Comprehensive Algorithm for Quantitative Real-Time Polymerase Chain Reaction. Journal of Computational Biology 12(8):1047-1064 (2005).

* cited by examiner

Fig. 2

PCR Control Template
⊗ 1 B

PCR Target One (Dengue Fever)
⊗ 1 B  ⊗ 2 G  ⊗ 3 Y  ⊗ 4 R

PCR Target Two (Tuberculosis)
⊗ 1 B  ⊗ 2 G  ⊗ 4 R

PCR Target Three (P17)
⊗ 1 B  ⊗ 2 G

PCR Target Four (Malaria)
⊗ 1 B  ⊗ 3 Y

PCR Target Five (Herpes)
⊗ 1 B  ⊗ 4 R

B: Blue
G: Green
Y: Yellow
R: Red

SIGNAL ENCODING AND DECODING IN MULTIPLEXED BIOCHEMICAL ASSAYS

CROSS-REFERENCE

This application is a continuation of U.S. patent application Ser. No. 15/914,356, filed Mar. 7, 2018, which is a continuation of U.S. patent application Ser. No. 14/451,876, filed Aug. 5, 2014, now U.S. Pat. No. 10,068,051, which is a continuation of U.S. patent application Ser. No. 13/756,760, filed Feb. 1, 2013, now U.S. Pat. No. 8,838,394, which claims the benefit of U.S. provisional applications 61/594,480, filed Feb. 3, 2012 and 61/703,093, filed Sep. 19, 2012. The content of these applications is incorporated herein by reference in its entirety.

STATEMENT AS TO FEDERALLY SPONSORED RESEARCH

This invention was made with the support of the United States government under Grant No. 1144469 awarded by the National Science Foundation. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 20, 2014, is named 38075-716-301-Seqlist.txt and is 9,260 bytes in size.

BACKGROUND

Multiplexed reactions offer significant advantages over traditional uniplex reactions, including performance of parallel reactions on the same sample, use of the same chamber to perform multiple reactions, and the ability to extract rich information from a sample in a fast and efficient manner. However, to achieve these benefits, multiplexed assays generally require complex reporting mechanisms, namely spectrally resolved fluorescence or chemiluminescence (e.g., PCR, ELISA), spatially resolved signals (e.g., microarrays, gel electrophoresis), temporally resolved signals (e.g., capillary electrophoresis), or combinations thereof (e.g., Sanger sequencing). There is a need for multiplexed reactions that can be carried out in a single solution.

SUMMARY OF THE INVENTION

This disclosure provides methods, compositions, systems, and kits for the multiplexed detection of analytes. In some cases, this disclosure provides assays that are capable of unambiguously detecting the presence or absence of each of at least 7 analytes, in any combination of presence or absence, in a single sample volume without immobilization, separation, mass spectrometry, or melting curve analysis. In some examples, each of the analytes is encoded as a value of one (or at least one) component of a signal.

In some examples, an assay provided in this disclosure is capable of unambiguously detecting the presence or absence of M analytes, in any combination of presence or absence, where $M=\log_2 (F+1)$ and F is the maximum cumulative value of one component of a signal (e.g., an intensity) when all the analytes are present.

In some cases, each analyte is encoded as at least one first value in a first component of a signal (e.g., at least one intensity or range of intensities) and at least one second value in a second component of a signal (e.g., at least one wavelength or range of wavelengths). In some examples, each analyte is encoded as a first value in a first component of a signal at each of a plurality of second values in a second component of a signal (e.g., a signal intensity or range of signal intensities at each of a plurality of wavelengths or ranges of wavelengths).

In some examples, an assay provided herein is capable of unambiguously detecting the presence or absence of M analytes, in any combination of presence or absence, where $M=C*\log_2 (F+1)$, where C is the number of the second values used to encode the analytes and F is the maximum cumulative value of the first component of the signal, for any second value, when all of the analytes are present.

In some cases, an assay provided in this disclosure is capable of unambiguously detecting the presence or absence of M analytes, in any combination of presence or absence, where $M=(P*T)+1$, where P is the number of codes per tier in a coding scheme and T is the number of tiers. In some cases, the number of tiers $T=\log_4 (F+1)$, and F is the maximum cumulative value of a first component of a signal, for any second value, when all of the analytes are present.

In some examples, the first value is an intensity or range of intensities. In some cases, a coding scheme comprises at least three intensities or ranges of intensities.

In some cases, the second value is a wavelength or range of wavelengths. In some examples, the coding scheme comprises at least five wavelengths or ranges of wavelengths.

In some examples, the signal is an electromagnetic signal. In some cases, the electromagnetic signal is a fluorescence emission signal. In some examples, the intensity of the fluorescence emission signal is measured at at least four wavelengths or ranges of wavelengths.

In some cases, an assay provided herein is performed with reagents that are lyophilized prior to use.

In some cases, a detecting step is performed with reagents comprising hybridization probes. In some examples, the number of the hybridization probes is greater than the number of analytes. In some cases, the set of hybridization probes comprise one or more hybridization probes specific for different analytes and comprising an identical fluorophore or combination of fluorophores. In some examples, a sample is contacted with at least 18 of said hybridization probes. In some examples, a detecting step is performed with reagents comprising at least one pair of primers. In some cases, at least one pair of primers are capable of amplifying a region complementary to at least three of said hybridization probes.

In some examples, the signal that is measured is generated during a polymerase chain reaction. In some cases, the polymerase chain reaction is selected from the group consisting of an end-point polymerase chain reaction, a real-time polymerase chain reaction, a digital polymerase chain reaction, and combinations thereof.

In some examples, at least one cumulative measurement is performed on a solution.

In some examples, at least one analyte is encoded by at least one additional value (i.e., at least two values together), wherein the at least one additional value is selected from the group consisting of a value from at least one additional component of a signal, a value from at least one component of a different signal, and combinations thereof. For example, the at least one additional value may be selected from the group consisting of a fluorescence emission intensity, a fluorescence emission wavelength, a Förster resonance energy transfer (FRET) emission intensity, a FRET emission wavelength, an electrochemical signal, a chemiluminescence wavelength, a chemiluminescence intensity, a fluorescence bleaching rate, a chemiluminescence bleaching rate, and combinations thereof.

In some cases, a chromatogram is constructed. The chromatogram may be constructed by plotting all possible combinations of first values and second values for positive control samples for each analyte.

In some examples, at least one of the analytes comprises a polynucleotide. In some cases, the polynucleotide is from a source selected from the group consisting of an animal, a plant, a bacteria, a fungus, a parasite, and a virus. In some examples, the polynucleotide is from a source selected from the group consisting of human immunodeficiency virus, herpes simplex virus, human papilloma virus, *Plasmodium*, *Mycobacterium*, dengue virus, hepatitis virus, and influenza virus. In some cases, the polynucleotide is selected from the group consisting of human immunodeficiency virus polyprotease, human immunodeficiency virus p17, human papilloma virus E6, and human papilloma virus E7.

In some cases, a sample is selected from the group consisting of a clinical sample, a food sample, an environmental sample, a pharmaceutical sample, and a sample from a consumer product.

In some examples, information concerning the presence or absence of an analyte is transmitted through a computer network.

In some cases, information concerning the presence or absence of an analyte is provided to a physician. In some examples, a clinical decision is made based on such information.

In some examples, at least one step of a method provided herein is performed using instructions on a computer readable medium. In some cases, the instructions are located on a remote server. In some examples, the instructions are located on a thermal cycler. In some cases, the instructions are located on a computer in communication with a thermal cycler.

In some cases, at least one of the analytes is a positive control analyte.

In some examples, the coding scheme is non-degenerate. In some cases, the coding scheme is designed to be non-degenerate. In some examples, the coding scheme is made non-degenerate by enumerating every legitimate result that can be obtained from the coding scheme, identifying each legitimate result that is degenerate, and eliminating at least one potential analyte code from the coding scheme to eliminate degeneracy.

In some cases, an assay provided herein is an end-point assay. In some examples an assay provided in this disclosure is ended at a threshold number of cycles set by the limit of detection of an instrument.

In certain examples, an assay provided herein is a liquid phase assay.

In some cases, an assay provided herein is quantitative.

In some cases, this disclosure provides a method of detecting the presence or absence of each analyte of a plurality of analytes, comprising: (a) encoding each of said analytes as a first value of a signal, thereby generating a coding scheme, wherein each of said analytes is represented in said coding scheme by said first value, wherein said encoding is performed in a manner that eliminates degeneracy; (b) providing a sample comprising, or potentially comprising, at least one of said analytes; (c) contacting said sample with analyte-specific reagents that generate said first value, as represented in said coding scheme, when each of said analytes is present; (d) cumulatively measuring said first values of said signal within said sample, thereby providing a cumulative measurement; and (e) determining whether each of said analytes is present or absent based on said cumulative measurement and said coding scheme.

In some examples, the method described in the preceding paragraph is capable of unambiguously detecting the presence or absence of M analytes, in any combination of presence or absence, where $M=\log_2 (F+1)$ and F is the maximum cumulative value of the first values when all of the analytes are present. In some cases, the first value is an intensity or range of intensities. In some examples, the first value has a minimum value in the coding scheme that is selected from the group consisting of at least 1, at least 2, at least 4, at least 8, at least 16, at least 32, and at least 64. In some cases, the first value is incremented in the coding scheme by an amount equal to the cumulative maximum of said preceding first values plus one. In other cases, the first value is incremented in the coding scheme by an amount greater than the cumulative maximum of the preceding first values plus one.

In some cases, this disclosure provides a method of detecting the presence or absence of each analyte of a plurality of analytes, comprising: (a) encoding each of said analytes as at least one first value and at least one second value, wherein said first value is a value from a first component of a signal and said second value is a value from a second component of said signal, thereby generating a coding scheme, wherein each of said analytes is represented in said coding scheme by said at least one first value and said at least one second value, wherein said encoding is performed in a manner that reduces or eliminates degeneracy; (b) providing a sample comprising, or potentially comprising, at least one of said analytes; (c) contacting said sample with analyte-specific reagents that generate said at least one first value and at least one said second value, as represented in said coding scheme, when each of said analytes is present; (d) cumulatively measuring said first values and said second values within said sample, thereby providing a cumulative measurement; and (e) determining whether each of said analytes is present or absent based on said cumulative measurement and said coding scheme, wherein, when degeneracy is eliminated, said method is capable of unambiguously detecting the presence or absence of each of at least six analytes in a single volume, in any combination of presence or absence, when each of said reagents generates only one second value.

In some cases, each of the analytes of the method described in the preceding paragraph is encoded as a first value in a first component of the signal at each of a plurality of second values in a second component of the signal. In some cases, when degeneracy is eliminated, this method is capable of unambiguously detecting the presence or absence of each of at least seven analytes in a single volume using four second values. In some examples, when degeneracy is eliminated, the coding scheme comprises T non-degenerate tiers, wherein $T=\log_4 (F+1)$ and F is the maximum cumulative value of the first component of the signal, for any second value, when all of the analytes are present. In some cases, when degeneracy is eliminated, the method is capable of unambiguously detecting the presence or absence of M analytes, in any combination of presence or absence, where $M=(P*T)+1$ and P is the number of codes per tier. In some examples, when degeneracy is eliminated, the method is capable of unambiguously detecting the presence or absence of M analytes, in any combination of presence or absence, where $M=C*\log_2 (F+1)$, C is the number of second values in the coding scheme, and F is the maximum cumulative value of the first component of the signal, for any second value, when all of the analytes are present.

This disclosure also provides non-degenerate coding schemes capable of unambiguously encoding the presence or absence of each of at least 7 analytes, in any combination of presence or absence, in a single sample volume without immobilization, separation, mass spectrometry, or melting curve analysis.

In some examples, a non-degenerate coding scheme of this disclosure is generated by a method comprising: (a) generating a code for each potential analyte, wherein each potential analyte is encoded by at least one value of at least one component of a signal; (b) enumerating every legitimate cumulative result for all possible combinations of presence or absence of each analyte; (c) identifying each legitimate result that is degenerate; and (d) eliminating at least one code to eliminate degeneracy. In some cases, the coding scheme may be expanded by adding additional codes that are at least one unit greater than the sum of all previous codes in the at least one component of said signal. In some cases a coding scheme is generated by a method of mathematical iteration that guarantees non-degeneracy by construction.

In some cases, this disclosure provides systems for detecting the presence or absence of each analyte of a plurality of analytes, comprising: (a) encoding each of said analytes as a first value of a signal, thereby generating a coding scheme, wherein each of said analytes is represented in said coding scheme by said first value, wherein said encoding is performed in a manner that eliminates degeneracy; (b) providing a sample comprising, or potentially comprising, at least one of said analytes; (c) contacting said sample with analyte-specific reagents that generate said first value, as represented in said coding scheme, when each of said analytes is present; (d) cumulatively measuring said first values of said signal within said sample, thereby providing a cumulative measurement; and (e) determining whether each of said analytes is present or absent based on said cumulative measurement and said coding scheme.

In some cases, this disclosure provides systems for detecting the presence or absence of each analyte of a plurality of analytes, comprising: (a) encoding each of said analytes as at least one first value and at least one second value, wherein said first value is a value from a first component of a signal and said second value is a value from a second component of said signal, thereby generating a coding scheme, wherein each of said analytes is represented in said coding scheme by said at least one first value and said at least one second value, wherein said encoding is performed in a manner that reduces or eliminates degeneracy; (b) providing a sample comprising, or potentially comprising, at least one of said analytes; (c) contacting said sample with analyte-specific reagents that generate said at least one first value and said at least one second value, as represented in said coding scheme, when each of said analytes is present; (d) cumulatively measuring said first values and said second values within said sample, thereby providing a cumulative measurement; and (e) determining whether each of said analytes is present or absent based on said cumulative measurement and said coding scheme, wherein, when degeneracy is eliminated, said system is capable of unambiguously detecting the presence or absence of each of at least six analytes in a single volume, in any combination of presence or absence, when each of said reagents generates only one second value.

In some cases, this disclosure provides methods of detecting the presence or absence of each analyte of a plurality of analytes for a third party, comprising: (a) obtaining the identity of each of said analytes from a party; (b) encoding each of said analytes as a first value of a signal, thereby generating a coding scheme, wherein each of said analytes is represented in said coding scheme by said first value, wherein said encoding is performed in a manner that eliminates degeneracy; (c) providing said party with analyte-specific reagents that generate said first value, as represented in said coding scheme, when each of said analytes is present, said party: (i) contacting a sample comprising, or potentially comprising, at least one of said analytes with said reagents; and (ii) cumulatively measuring said first values within said sample, thereby providing a cumulative measurement; and (d) obtaining said cumulative measurement from said party; (e) determining whether each of said analytes is present or absent based on said cumulative measurement and said coding scheme; and (f) providing said party with information about the presence or absence of each of said analytes.

In some cases, this disclosure provides methods of detecting the presence or absence of each analyte of a plurality of analytes for a third party, comprising: (a) obtaining the identity of each of said analytes from a party; (b) encoding each of said analytes as at least one first value and at least one second value, wherein said first value is a value from a first component of a signal and said second value is a value from a second component of said signal, thereby generating a coding scheme, wherein each of said analytes is represented in said coding scheme by said at least one first value and said at least one second value, wherein said encoding is performed in a manner that reduces or eliminates degeneracy; (c) providing said party with analyte-specific reagents that generate said at least one first value and said at least one second value, as represented in said coding scheme, when each of said analytes is present, said party: (i) contacting a sample comprising, or potentially comprising, at least one of said analytes with said reagents; and (ii) cumulatively measuring said first values and said second values within said sample, thereby providing a cumulative measurement; and (d) obtaining said cumulative measurement from said party; (e) determining whether each of said analytes is present or absent based on said cumulative measurement and said coding scheme; and (f) providing said party with information about the presence or absence of each of said analytes.

In some cases, this disclosure provides compositions for detecting the presence or absence of each analyte of a plurality of analytes, comprising analyte-specific reagents, each reagent generating a signal comprising a first value, wherein said reagents are capable of unambiguously detecting the presence or absence of each of at least seven analytes in a single sample volume, in any combination of presence or absence, without immobilization, separation, mass spectrometry, or melting curve analysis.

In some cases, this disclosure provides compositions for detecting the presence or absence of each analyte of a plurality of analytes, comprising analyte-specific reagents, each reagent generating a signal comprising at least one first value that is a value from a first component of said signal and at least one second value that is a value from a second component of said signal, wherein said reagents are capable of detecting the presence or absence of each of at least six analytes in a single volume, in any combination of presence or absence, when each of said reagents generates only one second value.

In some cases, this disclosure provides kits for detecting the presence or absence of each analyte of a plurality of analytes, comprising analyte-specific reagents, packaging, and instructions, each reagent generating a signal comprising a first value, wherein said kit is capable of unambiguously detecting the presence or absence of each of at least seven analytes in a single sample volume, in any combination of presence or absence, without immobilization, separation, mass spectrometry, or melting curve analysis.

In some examples, this disclosure provides kits for detecting the presence or absence of each analyte of a plurality of analytes, comprising analyte-specific reagents, packaging, and instructions, each reagent generating a signal comprising at least one first value that is a value from a first component of said signal and at least one second value that is a value from a second component of said signal, wherein said kit is capable of detecting the presence or absence of each of at least six analytes in a single volume, in any combination of presence or absence, when each of said reagents generates only one second value.

In some cases, this disclosure provides kits for detecting the presence or absence of each analyte of a plurality of analytes, comprising a kit body (601), clamping slots arranged in the kit body for placing bottles, a bottle comprising probes for the detection of an analyte (602), a bottle comprising primers for amplification (603), and a bottle comprising reagents for amplification (604), wherein said kit is capable of unambiguously detecting the presence or absence of each of at least seven analytes in a single sample volume, in any combination of presence or absence, without immobilization, separation, mass spectrometry, or melting curve analysis.

In some examples, this disclosure provides kits for detecting the presence or absence of each analyte of a plurality of analytes, a kit body (601), clamping slots arranged in the kit body for placing bottles, a bottle comprising probes for the detection of an analyte (602), a bottle comprising primers for amplification (603), and a bottle comprising reagents for amplification (604), each probe generating a signal comprising at least one first value that is a value from a first component of said signal and at least one second value that is a value from a second component of said signal, wherein said kit is capable of detecting the presence or absence of each of at least six analytes in a single volume, in any combination of presence or absence, when each of said probes generates only one second value.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows a schematic representation of detection of six analytes (including control) with four colors. The analytes are detected using hybridization probes attached to a fluorophore (B, G, Y, R; blue, green, yellow, and red, respectively) and a quencher (oval with "X"). The control sequence and the five other sequences (Dengue Fever=dengue virus; Tuberculosis=*Mycobacterium tuberculosis*; P17=HIV p17; Malaria=*Plasmodium falciparum*; and Herpes=herpes simplex virus 2) are all detected using a probe labeled with a blue fluorophore. The non-control analytes are each detected using 1-3 additional probes. For example, the dengue virus analyte is detected using three additional probes with green, yellow, and red fluorophores; the herpes simplex virus 2 analyte is detected using one additional probe with a red fluorophore; and so on.

DETAILED DESCRIPTION OF THE INVENTION

Figure 1:
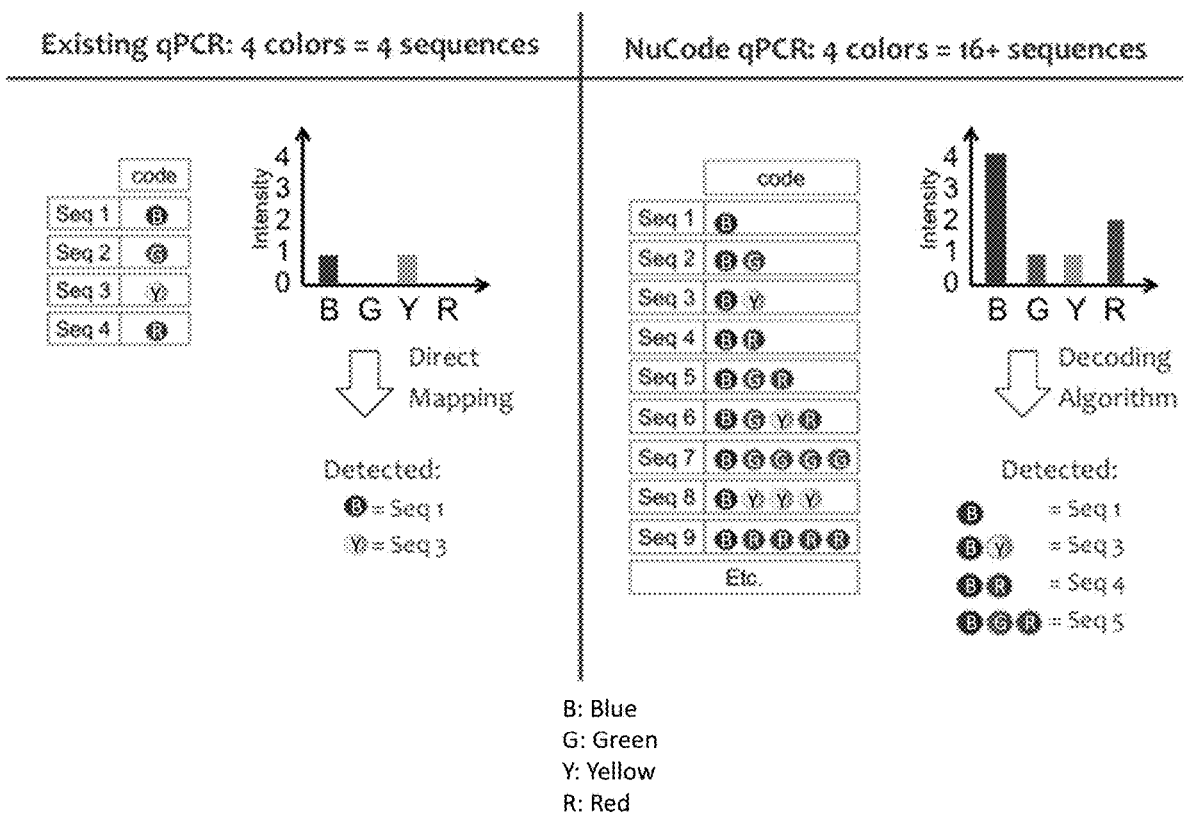
FIG. 1 shows a comparison between a traditional encoding method of detecting four analytes with four colors and an encoding method of the invention able to detect 16 or more sequences with four colors. Colors are indicated by B, G, Y, and R, which indicate blue, green, yellow, and red, respectively.

Fluorescence detection has been a preferred technique for multiplexed assays because of several desirable features, including compatibility with biochemical assays, the relatively small size of fluorescent labels, simple means of conjugation to molecules of interest, affordability, low toxicity, stability, robustness, detectability with inexpensive optics, and an ability to be combined with spatial arrays. However, standard fluorophores have wide emission spectra. Therefore, in order to avoid spectral overlap (i.e., to preserve spectral resolution) only a relatively small number of colors (e.g., 4 to 6) are typically used simultaneously in multiplexed fluorescent assays.

The traditional encoding method for multiplexed fluorescent assays has been to encode each analyte with a single color; i.e., M=N, where M is the number of analytes that can be detected and N is the number of spectrally resolved fluorescent probes. Whenever higher factors of multiplexing are required (i.e., M>N), fluorescence is generally combined with other techniques, such as aliquoting, spatial arraying, or sequential processing. These additional processing steps are labor-intensive and frequently require relatively expensive and complex optical and mechanical systems (e.g., spectrometers, mechanized microscopy stages, microfluidics, droplet generators, scanners, and the like). Such systems are often impractical to deploy in certain settings, particularly point-of care and low-resource settings. Thus, there is a significant need for multiplexed encoding and decoding methods that can provide an inexpensive means of multiplexing while avoiding the use of expensive additional processing steps.

This disclosure provides methods, systems, compositions, and kits for the detection of multiple analytes in a sample. Analytes are detected based on the encoding, analysis, and decoding methods presented herein. In some examples, each analyte to be detected is encoded as a value of a signal (e.g., intensity), where the values are assigned so that the results of the assay unambiguously indicate the presence or absence of the analytes being assayed. In other examples, each analyte to be detected is encoded as a value in each of at least two components of a signal (e.g., intensity and wavelength). The at least two components of a signal may be orthogonal. Similarly, as described more fully elsewhere in this disclosure, multiple orthogonal signals may be used, such as a combination of a fluorescent signal and an electrochemical signal. The analyte may be any suitable analyte, such as a polynucleotide, a protein, a small molecule, a lipid, a carbohydrate, or mixtures thereof. The signal may be any suitable signal such as an electromagnetic signal, a light signal, a fluorescence emission signal, an electrochemical signal, a chemiluminescent signal, and combinations thereof. The at least two components of the signal may be any suitable two components, such as an amplitude and a frequency or an intensity and a wavelength.

After encoding of the analytes, a sample is provided wherein the sample comprises or may comprise at least one of the encoded analytes. The sample is contacted with an analyte-specific reagent or reagents that generate a particular signal, as specified for each analyte in the coding scheme, in the presence of an analyte. A reagent may be any suitable reagent that is capable of generating such a signal in the presence of its corresponding analyte, for example, an oligonucleotide probe attached to a fluorophore and a quencher (e.g., a TAQMAN probe). If the reagent is an oligonucleotide probe attached to a fluorophore and a quencher, a nucleic acid amplification may be performed to generate the signal.

After addition of the reagent(s), the signal is quantified. In some cases, this quantification is performed by measuring one component of the signal (e.g., fluorescence intensity) and determining the presence and absence of certain analytes based on the values used to encode the presence of each analyte and the cumulative value of the signal.

In some cases, at least two components of a signal (e.g., intensity and wavelength) are cumulatively measured for the sample. This measurement can be performed, for example, by measuring the intensity at a particular wavelength or the intensity within a particular range of wavelengths. The presence or absence of an analyte may then be determined based on the values of each of the at least two components of the signal and the values used to encode the presence of the analyte (i.e., those values in the coding scheme).

The encoding may be performed in a manner that reduces or eliminates the number of possible degenerate (e.g., ambiguous) results that can be obtained by the method. As described elsewhere in this specification, the full coding capability of a particular coding scheme may be enumerated, and certain potential analyte codes may be eliminated from the coding scheme to reduce or eliminate degeneracy. Similarly, a coding scheme may be designed to be non-degenerate, so that a reduction or elimination of degeneracy is not necessary. A decoding matrix may be constructed to translate cumulative signal measurements (e.g., intensities or intensities at particular wavelengths) into the presence or absence of certain analytes, corresponding to the constituent signals of the cumulative signal measurement.

I. Definitions

The terminology used herein is for the purpose of describing particular embodiments only and is not intended to be limiting.

As used herein, the singular forms "a," "an," and "the" are intended to include the plural forms as well, unless the context clearly indicates otherwise. Furthermore, to the extent that the terms "including," "includes," "having," "has," "with," "such as," or variants thereof, are used in either the specification and/or the claims, such terms are not limiting and are intended to be inclusive in a manner similar to the term "comprising".

The term "about," as used herein, generally refers to a range that is 15% greater than or less than a stated numerical value within the context of the particular usage. For example, "about 10" would include a range from 8.5 to 11.5.

The terms "dimension" and "component," as used herein when referring to a signal, generally refer to an aspect of the signal that may be quantified. For example, if a signal is generated by a fluorescent molecule, it may be quantified in terms of its wavelength (e.g., a first dimension or component) and its intensity (e.g., a second dimension or component).

The term "decoding," as used herein, generally refers to a method of determining which analytes are present based on the cumulative signal and a coding scheme or decoding matrix that enables the conversion of a cumulative signal to information concerning the presence or absence of one or more analytes.

The term "encoding," as used herein, generally refers to the process of representing an analyte using a code comprising values of a signal, such as intensity, or values in each of at least two components of a signal or signals, such as wavelength and intensity.

The terms "oligonucleotide probe attached to a fluorophore and a quencher" and "TAQMAN probe" generally refer to hydrolysis probes used to detect the presence of an analyte in a polynucleotide amplification assay. These probes comprise an oligonucleotide probe attached to a fluorophore and a quencher. So long as the quencher and the fluorophore are in proximity, the quencher quenches the fluorescence emitted by the fluorophore upon excitation by a light source. The sequence of the oligonucleotide probe is designed to be complementary to a polynucleotide sequence present in an analyte, and therefore capable of hybridizing to the polynucleotide sequence present in the analyte. Hybridization of the oligonucleotide probe is performed in a nucleic acid amplification reaction comprising primers (e.g., a polymerase chain reaction). Upon extension of the primers by a DNA polymerase, the 5' to 3' exonuclease activity of the polymerase degrades the probe, releasing the fluorophore and the quencher into the medium. The proximity between the fluorophore and the quencher is broken and the signal from the fluorophore is no longer quenched. Thus, the amount of fluorescence detected is a function of the amount of analyte present. If no analyte is present, the probe will not hybridize to an analyte, and the fluorophore and quencher will remain in close proximity. Little or no signal will be produced.

The term "orthogonal," as used herein, generally refers to at least two components of a signal (e.g., wavelength and intensity), or at least two different signals (e.g., fluorescence emission and electrochemical signal), that can be varied independently or approximately independently. For example, wavelength and intensity are considered orthogonal or approximately orthogonal when fluorescent molecules are used. Among other factors, the wavelength of fluorescence emission will depend on the composition of the fluorescent molecule and the intensity of the fluorescence will depend on the amount of molecule present. Although wavelength and intensity are examples of two components of a signal that can be varied approximately independently, the methods described herein are not limited to components that can be varied independently or approximately independently. Components of a signal, or signals, that vary non-independently may also be used, so long as the components or signals are characterized well enough to enable encoding, measurement, and decoding. For example, if the variance in one component or signal affects the variance in another component or signal, the two components or signals may still be used so long as the relationship between the variances is understood.

The terms "polynucleotide," "oligonucleotide," or "nucleic acid," as used herein, are used herein to refer to biological molecules comprising a plurality of nucleotides. Exemplary polynucleotides include deoxyribonucleic acids, ribonucleic acids, and synthetic analogues thereof, including peptide nucleic acids.

The term "probe," as used herein, generally refers to a reagent capable of generating a signal in the presence of a particular analyte. A probe generally has at least two portions: a portion capable of specifically recognizing an analyte, or a portion thereof, and a portion capable of generating a signal in the presence of an analyte, or a portion thereof. A probe may be an oligonucleotide probe attached to a fluorophore and a quencher, as described above and elsewhere in this disclosure. A probe may also be any reagent that generates a signal in the presence of an analyte, such as an antibody that detects an analyte, with a fluorescent label that emits or is quenched upon binding of the antibody to an analyte. Any suitable probe may be used with the methods presented in this disclosure, so long as the probe generates a quantifiable signal in the presence of an analyte. For example, the analyte-specific portion of a probe may be coupled to an enzyme that, in the presence of an analyte, converts an uncharged substrate into a charged product, thereby increasing the electrical conductivity in the medium over time. In this case, different analytes may be encoded by coupling the analyte-specific portion of the probe (e.g., hybridization probe or antibody) to an enzyme at different ratios. The resulting rate of increased conductivity in the medium will be cumulative for all analytes present in the medium. Encoding analytes according to the methods provided herein enables conversion of the conductivity measurements into unambiguous (i.e., non-degenerate) results providing information about the presence or absence of particular analytes. Similarly, a probe may comprise an enzyme producing a chemiluminescent product from a substrate. The amount of chemiluminescence may then be used to encode the presence of particular analytes.

II. Encoding and Decoding Methods

A. Traditional Fluorescent Encoding and Decoding Method

A commonly used method of determining the presence of an analyte uses four spectrally resolved fluorescent molecules to indicate the presence or absence of four analytes. An example of this method is presented on the left-hand side of FIG. 1. The left-hand side of FIG. 1 shows an encoding method where four analytes (Seq 1, Seq 2, Seq 3, and Seq 4) are each encoded by a single color (blue, green, yellow, and red, respectively). The color represents a fluorophore attached to an oligonucleotide probe that also comprises a quencher. In the system shown on the left-hand side of FIG. 1, there are four different oligonucleotide probes, each comprising a single fluorophore (blue, green, yellow, or red) and a quencher. The presence or absence of an analyte is determined based on the presence or absence of a signal in a particular color.

The chart on the left-hand side of FIG. 1 shows intensity versus color for a hypothetical sample containing two analytes: Seq 1 and Seq 3. The presence of these analytes is determined based on the measurement of a blue signal (corresponding to Seq 1) and a yellow signal (corresponding to Seq 3). The absence of Seq 2 and Seq 4 is indicated by the absence of a blue and red signal.

Table 1 shows a translation of this coding scheme into a binary format. Each analyte is encoded as a value in each of two components of a fluorescent signal: (1) color (also known as wavelength; or range of wavelengths) and (2) intensity (indicated by the numbers within the table). For example, A (e.g., Seq 1) has a color of blue and an intensity of 1; B (e.g., Seq 2) has a color of green and an intensity of 1; and so on. The intensity of the signal within each color range may be quantified as described herein, for example by measuring the intensity of the signal within a particular wavelength range determined by a band pass filter. A result of 1000 indicates that only analyte A is present; a result of 1100 indicates that analytes A and B are present; and so on.

TABLE 1

Traditional encoding of four analytes with four probes, each probe having a single color, and one probe per analyte.

| | Blue | Green | Yellow | Red |
|---|---|---|---|---|
| A | 1 | 0 | 0 | 0 |
| B | 0 | 1 | 0 | 0 |
| C | 0 | 0 | 1 | 0 |
| D | 0 | 0 | 0 | 1 |

B. Encoding Methods Using More than One Color Per Analyte

The traditional method described above suffers from the fact that it is limited by the number of spectrally resolvable fluorophores. More specifically, the number of detectable analytes is equal to the number of spectrally resolvable fluorophores. Therefore, the number of analytes may only be increased by increasing the number of spectrally resolvable fluorophores.

This disclosure provides methods that overcome this limitation. More specifically, in some cases, by utilizing at least two components of a signal during encoding, the methods described herein may be used to detect more than one analyte per fluorophore. For example, using the method provided herein 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes may be detected per fluorophore. In some cases, the methods provided herein may be used to detect at least 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes may be detected per fluorophore. In some cases, the methods provided herein may be used to detect 1.5-2, 2-4, 1.5-4, 4-6, 2-6, 6-10 analytes per fluorophore.

In some cases, the methods provided in this disclosure may include the use of a control color. The control color may be attached to one or more probes binding a positive control analyte, and each analyte to be detected, in a sample. If the same sequence occurs in the positive control analyte and each analyte to be detected, a single control probe may be used. If the same sequence does not occur in the positive control analyte and each analyte to be detected, different probes may be used, but each probe may still be attached to the control color.

For example, building on the traditional methods described above, one color (e.g., blue) may be used to encode the presence of a control analyte that is always present in the sample. The control analyte may be added to the sample, or may be inherently present in the sample. The remaining colors (e.g., green, yellow, red) may be used to encode the presence of additional analytes. Table 2 shows an example of one such method.

TABLE 2

Encoding of four analytes, including control, with four colors and up to two colors per analyte.

|  | Blue | Green | Yellow | Red |
|---|---|---|---|---|
| Ctrl. (p) | 1 | 0 | 0 | 0 |
| A | 1 | 0 | 0 | 1 |
| B | 1 | 0 | 1 | 0 |
| C | 1 | 1 | 0 | 0 |

In Table 2, the presence of the control (p) is indicated by a result of 1000. The presence of the control and analyte A is indicated by a result of 2001. The presence of the control and all three other analytes is indicated by a result of 4111. The control color (blue) provides an indication that the assay is functioning properly. The intensity of the blue color reports the number of analytes that are present in a test sample. Of course, any color may be used as the control color. One of skill in the art will recognize that certain practical considerations might make it preferable to use one color over another as the control color. For example, if one color is better detected in a particular optical system (or system of fluorophores), it might be practically preferable to use that color as a control color.

The coding scheme shown in Table 2 encodes each analyte using one control color and one additional color (up to 2 probes per analyte). However, as shown below, the number of analytes that can be encoded increases when up to 4 colors are used per analyte. Table 3 shows an exemplary coding scheme where each analyte is encoded by up to 4 colors. In the scheme shown in Table 3, the control color (blue) is generated in the presence of the control sequence and each of the other seven analytes (A-G). The other seven analytes are each encoded by the presence of one to three additional colors. The colors may be contained on different probes (e.g., oligonucleotide probes attached to a fluorophore and a quencher) or on the same probe (which can have multiple fluorophores and multiple quenchers).

TABLE 3

Encoding of eight analytes (including control) with four colors and up to four colors per analyte.

|  | Blue | Green | Yellow | Red |
|---|---|---|---|---|
| Ctrl. (p) | 1 | 0 | 0 | 0 |
| A | 1 | 0 | 0 | 1 |
| B | 1 | 0 | 1 | 0 |
| C | 1 | 1 | 0 | 0 |
| D | 1 | 0 | 1 | 1 |
| E | 1 | 1 | 0 | 1 |
| F | 1 | 1 | 1 | 0 |
| G | 1 | 1 | 1 | 1 |

TABLE 3-continued

Encoding of eight analytes (including control) with four colors and up to four colors per analyte.

In Table 3, the presence of the control and all seven other analytes is indicated by a result of 8444. Three analytes (A, B, and C) are encoded by two colors. Three analytes (D, E, and F) are encoded by three colors, and one analyte (G) is encoded by four colors. The presence of the control (p) is indicated by a result of 1000. The presence of the control and analyte A is indicated by a result of 2001. The presence of the control and analyte G is indicated by a result of 2111. These results express the cumulative intensity of the signal in each color. For example, the result 2111 has a 2× signal intensity in the blue channel, while the result 1000 has only a 1× signal intensity in the blue channel.

Using Table 3, each of the possible cumulative assay results can be enumerated, in terms of color (blue, green, yellow, red) and intensity (0-8). Table 4 shows a "decoding matrix" generated by enumerating each of the possible cumulative assay results based on the encoding method presented in Table 3 and providing the corresponding decoded result of each assay in terms of the analyte(s) present in the sample. A similar decoding matrix may be generated for any coding scheme described herein, by enumerating each of the possible cumulative assay results based on the coding scheme and providing the corresponding decoded result of each assay in terms of the analyte(s) present in (or absent from) the sample. In some cases, as described below, one or more analytes may be removed from the coding scheme in order to reduce or eliminate degeneracy.

TABLE 4

Decoding matrix for encoding method presented in Table 3.

| Cumulative Assay Result | | | | |
|---|---|---|---|---|
| Blue | Green | Yellow | Red | Analyte(s) Present |
| 1 | 0 | 0 | 0 | p |
| 2 | 0 | 0 | 1 | pA |
| 2 | 0 | 1 | 0 | pB |
| 2 | 1 | 0 | 0 | pC |
| 2 | 0 | 1 | 1 | pD |
| 2 | 1 | 0 | 1 | pE |
| 2 | 1 | 1 | 0 | pF |
| 2 | 1 | 1 | 1 | pG |
| 3 | 0 | 1 | 1 | pAB |
| 3 | 1 | 0 | 1 | pAC |
| 3 | 0 | 1 | 2 | pAD |
| 3 | 1 | 0 | 2 | pAE |
| 3 | 1 | 1 | 1 | pAF, pCD, pBE |
| 3 | 1 | 1 | 2 | pAG, pDE |
| 3 | 1 | 1 | 0 | pBC |
| 3 | 0 | 2 | 1 | pBD |
| 3 | 1 | 2 | 0 | pBF |
| 3 | 1 | 2 | 1 | pBG, pDF |
| 3 | 2 | 0 | 1 | pCE |
| 3 | 2 | 1 | 0 | pCF |
| 3 | 2 | 1 | 1 | pCG, pEF |
| 3 | 1 | 2 | 2 | pDG |
| 3 | 2 | 1 | 2 | pEG |
| 3 | 2 | 2 | 1 | pFG |
| 4 | 1 | 1 | 1 | pACB |
| 4 | 0 | 2 | 2 | pABD |

TABLE 4-continued

Decoding matrix for encoding method presented in Table 3.

| Cumulative Assay Result | | | | |
|---|---|---|---|---|
| Blue | Green | Yellow | Red | Analyte(s) Present |
| 4 | 2 | 2 | 0 | pBCF |
| 4 | 2 | 0 | 2 | pACE |
| 4 | 1 | 1 | 2 | pABE, pACD |
| 4 | 1 | 2 | 1 | pABF, pBCD |
| 4 | 2 | 1 | 1 | pACF, pBCE |
| 4 | 1 | 2 | 2 | pADF, pABG, pBDE |
| 4 | 2 | 1 | 2 | pACG, pCDE, pAEF |
| 4 | 2 | 2 | 1 | pBCG, pBEF, pCDF |
| 4 | 2 | 2 | 2 | pCDG, pAFG, pBEG, pDEF |
| 4 | 1 | 1 | 3 | pADE |
| 4 | 1 | 3 | 1 | pBDF |
| 4 | 3 | 1 | 1 | pCEF |
| 4 | 1 | 2 | 3 | pADG |
| 4 | 3 | 2 | 1 | pCFG |
| 4 | 2 | 1 | 3 | pAEG |
| 4 | 2 | 3 | 1 | pBFG |
| 4 | 1 | 3 | 2 | pBDG |
| 4 | 3 | 1 | 2 | pCEG |
| 4 | 2 | 2 | 3 | pDEG |
| 4 | 3 | 2 | 2 | pEFG |
| 5 | 1 | 2 | 2 | pABCD |
| 5 | 2 | 1 | 2 | pABCE |
| 5 | 2 | 2 | 1 | pABCF |
| 5 | 2 | 2 | 2 | pABCG, pABEF, pBCDE, pACDF |
| 5 | 1 | 2 | 3 | pABDE |
| 5 | 2 | 1 | 3 | pACDE |
| 5 | 1 | 3 | 2 | pABDF |
| 5 | 2 | 1 | 3 | pBCDF |
| 5 | 3 | 1 | 2 | pACEF |
| 5 | 3 | 2 | 1 | pBCEF |
| 5 | 2 | 2 | 3 | pABEG, pACDG, pADEF |
| 5 | 2 | 3 | 2 | pABFG, pBCDG, pBDEF |
| 5 | 3 | 2 | 2 | pACFG, pBCEG, pCDEF |
| 5 | 1 | 3 | 3 | pABDG |
| 5 | 3 | 1 | 3 | pACEG |
| 5 | 3 | 3 | 1 | pBCFG |
| 5 | 2 | 3 | 3 | pADFG, pBDEG |
| 5 | 3 | 3 | 2 | pBEFG, pDEFG |
| 5 | 3 | 2 | 3 | pCDEG, pAEFG |
| 5 | 2 | 2 | 4 | pADEG |
| 5 | 2 | 4 | 2 | pBDFG |
| 5 | 4 | 2 | 2 | pCEFG |
| 5 | 3 | 3 | 3 | pDEFG |
| 6 | 2 | 2 | 3 | pABCDE |
| 6 | 2 | 3 | 2 | pABCDF |
| 6 | 3 | 2 | 2 | pABCEF |
| 6 | 2 | 3 | 3 | pABCDG, pABDEF |
| 6 | 3 | 2 | 3 | pABCEG, pACDEF |
| 6 | 3 | 3 | 2 | pABCFG, pBCDEF |
| 6 | 4 | 3 | 2 | pBCEFG |
| 6 | 4 | 2 | 3 | pACEFG |
| 6 | 3 | 3 | 3 | pABEFG, pACDFG, pBCDEG |
| 6 | 3 | 4 | 2 | pBCDFG |
| 6 | 2 | 4 | 3 | pABDFG |
| 6 | 3 | 2 | 4 | pACDEG |
| 6 | 2 | 3 | 4 | pABDEG |
| 6 | 4 | 3 | 3 | pCDEFG |
| 6 | 3 | 4 | 3 | pBDEFG |
| 6 | 3 | 3 | 4 | pADEFG |
| 7 | 4 | 4 | 3 | pBCDEFG |
| 7 | 4 | 3 | 4 | pACDEFG |
| 7 | 3 | 4 | 4 | pABDEFG |
| 7 | 4 | 3 | 3 | pABCEFG |
| 7 | 3 | 4 | 3 | pABCDFG |
| 7 | 3 | 3 | 4 | pABCDEG |
| 7 | 3 | 3 | 3 | pABCDEF |
| 8 | 4 | 4 | 4 | pABCDEFG |

The decoding matrix provided in Table 4 is constructed using two assumptions. First, the decoding matrix assumes that the positive control (p) always produces a positive outcome. Second, the decoding matrix assumes that, within each color, the intensity is additive and scales in the same way with changing probe concentration, regardless of which probe the signal may come from. This essentially means that the signals are additive and digital. The conditions underlying these assumptions may be met by properly preparing the assay. If a fluorescent signal is used, the intensity need only be approximately additive and digital, as demonstrated in the Examples provided herein.

Table 4 allows the conversion of a cumulative measurement of intensity in four ranges of fluorescent wavelengths (i.e., signal intensity within each color range), into the corresponding analytes present in the sample. For example, a result of 4321 indicates that p, C, F, and G are present and the other analytes are not present. This result is referred to as a "legitimate" result, because it is present in the decoding matrix. By contrast, a result of 4000, while possible to measure, does not occur in the decoding matrix. More specifically, the result of 4000 cannot be achieved by adding any combination of control and analyte codes from Table 3. This result is referred to as an "illegitimate" result. An illegitimate result may indicate that the assay malfunctioned. Thus, the control (p) and the decoding matrix provide a means of verifying that the assay is functioning properly.

Table 4 is exhaustive for any combination of fluorophores generating four resolvable emission spectra (e.g., colors). The term "rank" is used to describe the number of detected analytes, including the control. In the example provided above, if the assay functions properly, the rank is equal to the value of the blue signal. For example, a rank of 8 indicates that the control and all seven other analytes (A-G) are present. A rank of 2 indicates that the control and only one analyte are present. The lowest rank is a rank of 1, which indicates that only the control is present. The number of possibilities at each rank can be enumerated. For example, continuing to refer to the encoding and decoding method described in Tables 3-4, there are 7 possibilities for rank 2. The number of possibilities at rank 3 can be calculated as a combination of 7 take 2, or 7!/(5!*2!)=21 possibilities. More generally, the number of possibilities for a combination of N take K is N!/((N−K)!*K!). Analogously, at ranks 4, 5, 6, 7, and 8, the number of possibilities is 35, 35, 21, 7, and 1, respectively. Referring to Table 4 shows that the table agrees with the theoretical prediction. Thus, Table 4 is an exhaustive decoding matrix for the encoding method provided in Table 3.

C. Reducing or Eliminating Degeneracy

The terms "degenerate" and "degeneracy," as used herein, generally describe a situation where a legitimate result is not definitive, because it can indicate more than one possibility in terms of the presence or absence of an analyte. For example, with reference to Table 4, result 5233 is degenerate because it can be decoded as either pADFG or pBDEG. Similarly, result 4222 is degenerate because it can be decoded as any of the following: pCDG, pAFG, pBEG, pDEF. By contrast, result 3110 can only indicate pBC and thus is not degenerate.

This disclosure provides methods of reducing or eliminating degeneracy, thereby increasing the confidence with which an analyte is detected. In one embodiment, degeneracy is eliminated by a method comprising (i) encoding each potential analyte to be detected as a value of a signal and, optionally, as a value in each of at least two components of a signal; (ii) enumerating every legitimate result that can be obtained from the coding scheme; (iii) identifying each legitimate result that is degenerate; and (iv) eliminating at least one potential analyte (or potential analyte code) from the coding scheme, wherein eliminating the at least one potential analyte reduces or eliminates degeneracy. For example, with reference to the coding scheme described in Table 3 and the decoding matrix described in Table 4 (enumerating every legitimate result), eliminating any two of analytes D, E, and F eliminates the degeneracy. Eliminating any one of analytes D, E, and F would not eliminate the degeneracy, but would reduce it.

With continued reference to the coding scheme described in Table 3, eliminating any two of analytes D, E, and F from the coding scheme results in a scheme where six analytes (including control) can be analyzed, with no degeneracy, using only 4 colors. By contrast, conventional methods of multiplexing would allow for only the reporting of 3 analytes and 1 control using 4 colors. Therefore, the number of analytes that can be analyzed is nearly doubled by using the methods provided herein.

FIG. 2 shows an exemplary embodiment of the invention in which 4 colors are used to detect five analytes and a control. The analytes are nucleic acids from dengue virus ("Dengue Fever"), *Mycobacterium tuberculosis* ("Tuberculosis"), human immunodeficiency virus (HIV) p17 (P17), Plasmodium ("Malaria"), and herpes simplex ("Herpes"). The "colors" in this example are fluorophores attached to oligonucleotide probes that also comprise a quencher. The oligonucleotide probes will generally be different for different analytes, whereas the color is the same. For example, all probes designated as Probe 1 have a blue color but generally will have a different oligonucleotide sequence. Of course, probes designated as Probe 1 could also have the same oligonucleotides sequence, if the complementary sequence was present in each of the analytes. The mechanism of detection with these probes is described elsewhere in this disclosure. Probe 1 (blue) hybridizes to all six analytes, including control. Probe 2 (green) hybridizes to analytes from dengue virus, *Mycobacterium*, and HIV p17. Probe 3 (yellow) hybridizes to analytes from dengue fever and *Plasmodium*. Probe 4 hybridizes to analytes from dengue virus, *Mycobacterium*, and herpes simplex. The coding scheme defined by these probes is illustrated in Table 5. With reference to Table 3, potential analytes D (1011) and F (1110) have been eliminated from the coding scheme. Therefore, the coding scheme presented in Table 5 is non-degenerate and each legitimate result from the assay corresponds to the presence or absence of a unique combination of analytes in a sample.

TABLE 5

Coding scheme for detection of dengue virus, *Mycobacterium*, HIV, *Plasmodium*, and herpes simplex, as exemplified in FIG. 2.

| | Blue | Green | Yellow | Red |
|---|---|---|---|---|
| Ctrl. (p) | 1 | 0 | 0 | 0 |
| Herpes Simplex | 1 | 0 | 0 | 1 |
| *Plasmodium* | 1 | 0 | 1 | 0 |
| HIV | 1 | 1 | 0 | 0 |
| *Mycobacterium* | 1 | 1 | 0 | 1 |
| Dengue Virus | 1 | 1 | 1 | 1 |

The methods for encoding and decoding presented above, including the methods for eliminating degeneracy, are all equally applicable to encoding methods using additional colors. For example, Table 3 could be extended by including additional colors and additional intensities (described further below). The decoding matrix is then generated as described above, enumerating every legitimate result that can be obtained from the coding scheme. A decoding matrix analogous to the decoding matrix provided in Table 4 may be constructed for any coding scheme described in this disclosure. The legitimate results that are degenerate are then identified and at least one potential analyte code is eliminated from the coding scheme to reduce or eliminate degeneracy. The method of eliminating degeneracy may be carried out using software on a computer readable medium, or hardware configured to carry out the method (e.g., a microchip).

Although degeneracy can be reduced or eliminated by the methods described above, and elsewhere in this disclosure, this disclosure also provides coding schemes that are non-degenerate by design. For example, after elimination of degeneracy in the coding scheme described in Table 3, the coding scheme may be extended indefinitely in a non-degenerate manner where the non-degeneracy is by design (see, e.g., the coding scheme exemplified in Table 6, described more fully below). Similarly, this disclosure provides coding schemes that are completely non-degenerate by design and therefore do not require any reduction or elimination of degeneracy (see, e.g., the coding scheme exemplified in Table 8, described more fully below). Thus, the coding schemes provided in this disclosure may have reduced or eliminated degeneracy, or be non-degenerate by design.

D. Encoding Methods Using More Than One Color and More Than One Intensity

The encoding method described above (e.g., Tables 3-5) may be further extended by allowing analytes to be encoded by an intensity greater than 1. For example, each of the analytes encoded in the coding scheme provided in Table 5 is encoded by a fluorescence intensity of either 1 or 0. Allowing higher values for the signal intensity in at least one color further increases the number of analytes that can be encoded by any of the methods provided in this disclosure. In some examples, these higher intensity values may be assigned any color except for the control color, in order to maintain the analyte counting capability of the control color.

Table 6 shows the first three tiers of an exemplary coding scheme that utilizes four colors and multiple intensities. Tier 1 of Table 6 is a reproduction of Table 3, showing the encoding of seven analytes and a control with four colors. As described above, any two of potential analytes D, E, and F may be eliminated from the coding scheme in order to produce a non-degenerate coding scheme. Tier 1 of Table 6 indicates that potential analytes D (1011) and F (1110) have been eliminated from the coding scheme to eliminate degeneracy. Therefore, the coding scheme presented in Tier 1 of Table 6 is capable of determining the presence of five analytes and one control using four colors, as described above.

The coding scheme of Tier 1 of Table 6 may be expanded to a second tier (Tier 2) by allowing the intensity in any of the colors to increase. As described above, the intensity of the control color may be maintained at 1, in order to preserve the sequence counting capability of the control. Increasing the intensity of any of the remaining three colors will yield codes 100Y, 10Y0, 1Y00, 10YY, 1Y0Y, 1YY0, and 1YYY, where Y>1. The minimal value of Y for a new tier of encoding is equal to the cumulative maximum value from the prior tier(s) plus 1. As described below, a value greater than 1 could also be used, to maximize the differences between the intensities.

Thus, in this context, the term "tier" is generally used to describe a set of codes that fully utilize the coding capability provided by a particular number of first values (e.g., intensities) and second values (e.g., colors), without degeneracy.

For example, Tier 1 of Table 6 fully utilizes the coding capability provided by four colors with up to one intensity in each color, without degeneracy. As shown in Table 6, Tier 1, this results in six encoded analytes, including the control. To introduce a second tier, the minimum value of Y (described above) may be incremented to equal the cumulative maximum result from the prior tier(s) plus one (or more than one). In the example provided in Table 6, the intensity of the blue (control) color is maintained as one, to preserve the sequence counting capability in this color. Thus, Tier 2 consists of five non-degenerate encoding possibilities obtained by incrementing the intensities in the green, yellow, and red channels to equal the cumulative maximum results in each of these channels from Tier 1, plus one. All possibilities of these codes may then be enumerated for Tier 2, and codes resulting in degeneracy may be eliminated, or Tier 2 may be made non-degenerate by design, using the information used to eliminate the corresponding codes from Tier 1. Further coding capacity may then be achieved by adding a third tier, or further tiers, which are constructed according to analogous methods. A coding scheme may have an infinite number of tiers, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more tiers.

More specifically, with reference to Table 6, Tier 2, analyte H is encoded by 1004. The value of the control color is maintained as 1. The value of the red color is equal to the cumulative maximum result from the prior tier (3) plus 1, or 4. Similarly, analytes I and J are encoded by 1030 and 1400, respectively. Combinations of these codes are used to encode the remaining four analytes (K–N), as was done for analytes D-G in Tier 1. This completes Tier 2. In Tier 2, the inclusion of potential analytes K (1034) and M (1430) results in degeneracy. Therefore, these analytes have been eliminated from the coding scheme, to eliminate degeneracy.

Continuing to refer to Table 6, a third tier (Tier 3) is constructed using the same principles described above. Analyte 0 is encoded by 1-0-0-16. The value of the control color is still maintained as 1. The value of the red color is equal to the cumulative maximum result from the prior tiers (15) plus 1, or 16. Similarly, analytes P and Q are encoded by 1-0-9-0 and 1-16-0-0, respectively. Combinations of these codes are used to encode the remaining four analytes (R–U), as was done for analytes D-G in Tier 1 and analytes K–N in Tier 2. In Tier 3, the inclusion of potential analytes R (1-0-9-16) and T (1-16-9-0) results in degeneracy. Therefore, these analytes have been eliminated from the coding scheme, to eliminate degeneracy.

The three-tier coding scheme shown in Table 6 shows the encoding of 15 analytes and one control using four colors. This coding scheme may be indefinitely extended, by adding more intensities to generate additional tiers and/or adding more colors, to generate additional coding capability within the tiers. The methods of reducing or eliminating degeneracy, as described in this disclosure, may be used with the addition of each intensity and/or color, to reduce or eliminate degenerate results.

More generally, the coding scheme depicted in Table 6 is a non-degenerate, infinite extension of the coding scheme depicted in Tables 3-5. The maximum intensity of the cumulative measurement at the first tier is 6. The maximum intensity of the cumulative measurement at the second tier is 15. The maximum intensity of the cumulative measurement at the third tier is 63, and so on. Given a maximum cumulative intensity value (F), the maximum number of tiers (T) available in this coding scheme is $T=\log_4(F+1)$. The coding scheme depicted in Table 6 provides five non-degenerate codes per tier (P). Thus, the maximum number of codes $M=5*\log_4(F+1)$, or $M=P*T$, where P is the number of non-degenerate codes per tier and T is the number of tiers. For example, given F=63, the maximum number of codes (i.e., analytes) is 15 for 5 non-degenerate codes per tier. This formula does not include the 1000 code, which is reserved for a positive control in Table 6. To include the control in the total number of analytes, one would simply add one, to provide the formula $M=(P*T)+1$.

The methods provided in this disclosure may be used to expand this coding scheme infinitely. For example, by utilizing combinations of different intensities (i.e., first values) and colors (i.e., second values) one can encode any number of analytes (M) by varying the number of non-degenerate codes per tier (P) and the number of tiers (T). For example, the number of non-degenerate codes per tier is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or more. Similarly, the number of tiers may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or more.

TABLE 6

Encoding of 15 analytes and one control using four colors and multiple intensities.

| Tier | Analyte | B | G | Y | R | Comments |
|---|---|---|---|---|---|---|
| 1 | Ctrl. (p) | 1 | 0 | 0 | 0 | |
| | A | 1 | 0 | 0 | 1 | |
| | B | 1 | 0 | 1 | 0 | |
| | C | 1 | 1 | 0 | 0 | |
| | ⋮ | ⋮ | ⋮ | ⋮ | ⋮ | Eliminated from coding scheme to eliminate degeneracy. |
| | E | 1 | 1 | 0 | 1 | |
| | ⋮ | ⋮ | ⋮ | ⋮ | ⋮ | Eliminated from coding scheme to eliminate degeneracy. |
| | G | 1 | 1 | 1 | 1 | |
| Cumulative Maximum Result | | 6 | 3 | 2 | 3 | |
| 2 | H | 1 | 0 | 0 | 4 | |
| | I | 1 | 0 | 3 | 0 | |
| | J | 1 | 4 | 0 | 0 | |
| | ⋮ | ⋮ | ⋮ | ⋮ | 4 | Eliminated from coding scheme to eliminate degeneracy. |
| | L | 1 | 4 | 0 | 4 | |
| | ⋮ | ⋮ | 4 | ⋮ | ⋮ | Eliminated from coding scheme to eliminate degeneracy. |
| | N | 1 | 4 | 3 | 4 | |
| Cumulative Maximum Result | | 11 | 15 | 8 | 15 | |
| 3 | O | 1 | 0 | 0 | 16 | |
| | P | 1 | 0 | 9 | 0 | |
| | Q | 1 | 16 | 0 | 0 | |
| | ⋮ | ⋮ | ⋮ | ⋮ | ⋮ | Eliminated from coding scheme to eliminate degeneracy. |
| | S | 1 | 16 | 0 | 16 | |
| | ⋮ | ⋮ | ⋮ | ⋮ | ⋮ | Eliminated from coding scheme to eliminate degeneracy. |

TABLE 6-continued

Encoding of 15 analytes and one control using four colors and multiple intensities.

| Tier | Analyte | B | G | Y | R | Comments |
|---|---|---|---|---|---|---|
| | U | 1 | 16 | 9 | 16 | |
| Cumulative Maximum Result | | | | | | |
| Cumulative Maximum Result for Three Non-Degenerate Tiers | | 16 | 63 | 26 | 63 | |

The right-hand side of FIG. 1 shows one exemplary embodiment of the method described above. More specifically, the right-hand side of FIG. 1 shows an encoding method where nine or more analytes (Seq 1-Seq 9, etc.) are each encoded by at least two colors, with varying intensities within each color. The color represents a fluorophore attached to an oligonucleotide probe that also comprises a quencher. The system can be designed so that each probe is labeled with single fluorophore, or each probe is labeled with more than one fluorophore. For example, the code for analyte H, in Table 6, is 1004. The intensity of 4 in the red channel may be achieved by either using an H-specific probe comprising 4 red fluorophores, or by using 4H-specific probes each comprising a single red fluorophore. Of course, any combination of probes and fluorophores producing a result of 4 in the red channel would be equally appropriate, such as 2 probes with 2 red fluorophores each, and 1 probe with 1 red fluorophore and 1 probe with 3 red fluorophores, or simply one probe with one red fluorophore but present at 4× amount in the reaction mixture.

The coding scheme depicted on the right-hand side of FIG. 1 may be represented as in Table 7. The result of the analysis shown on the right-hand side of FIG. 1 is 4112, or an intensity of 4 in the blue channel, 1 in the green channel, 1 in the yellow channel, and 2 in the red channel. Using a decoding matrix constructed as described herein, this result is decoded to indicate the presence of Seq 1, Seq 3, Seq 4, and Seq 5.

TABLE 7

Coding scheme illustrated on the right-hand side of FIG. 1.

| Tier | Analyte | B | G | Y | R | Comments |
|---|---|---|---|---|---|---|
| 1 | Seq 1 | 1 | 0 | 0 | 0 | |
| | Seq 2 | 1 | 1 | 0 | 0 | |
| | Seq 3 | 1 | 0 | 1 | 0 | |
| | Seq 4 | 1 | 0 | 0 | 1 | |
| | Seq 5 | 1 | 1 | 0 | 1 | |
| | Seq 6 | 1 | 1 | 1 | 1 | |
| | ~~Eliminated~~ ~~Potential Seq~~ | ~~1~~ | ~~0~~ | ~~1~~ | ~~1~~ | Eliminated from coding scheme to eliminate degeneracy. |
| | ~~Eliminated~~ ~~Potential Seq~~ | ~~1~~ | ~~1~~ | ~~1~~ | ~~0~~ | Eliminated from coding scheme to eliminate degeneracy. |
| Cumulative Maximum Result | | 6 | 3 | 2 | 3 | |
| 2 | Seq 7 | 1 | 4 | 0 | 0 | |
| | Seq 8 | 1 | 0 | 3 | 0 | |

TABLE 7-continued

Coding scheme illustrated on the right-hand side of FIG. 1.

| Tier | Analyte | B | G | Y | R | Comments |
|---|---|---|---|---|---|---|
| | Seq 9 | 1 | 0 | 0 | 4 | |
| | Etc.-i.e. Continue as provided in Table 6. | | | | | |

E. Encoding Methods Using One Color and One Intensity Per Analyte but Different Intensities Among Analytes In some methods provided herein, each analyte is encoded by a single color and intensity combination. For example, in a four color system, the first four analytes may be encoded by 1000, 2000, 4000, and 8000. The next four analytes may be encoded by 0100, 0200, 0400, and 0800. Analytes 9-12 and 13-16 would be assigned analogously, as shown in Table 8.

Like the encoding method described in Table 6, this coding scheme is theoretically infinite, non-degenerate by construction, and only limited by the bandwidth of the instrument used to measure the signal. However, this coding scheme enables more analytes to be quantified per unit of bandwidth than the encoding method described in Table 6. The reason is that the available multiplicity of signal is used with maximal efficiency, as each level of intensity is utilized in the coding (i.e. there are no gaps in the chromatogram; see below for description of chromatograms). Table 8 shows one embodiment of this method, illustrating four tiers of encoding based on four colors and intensities 1, 2, 4, and 8. The coding scheme is non-degenerate, and the result if all 16 analytes are present is 15-15-15-15. This encoding method is more efficient, in terms of bandwidth utilization, than the encoding methods presented above. However, this method does not have the proofreading capability of the first scheme, as all the results decode to legitimate outcomes in the absence of gaps in the chromatogram.

TABLE 8

Example of encoding method using one color and one intensity per analyte, but different intensities among analytes.

| Tier | Analyte | B | G | Y | R |
|---|---|---|---|---|---|
| 1 | A | 1 | 0 | 0 | 0 |
| | B | 2 | 0 | 0 | 0 |
| | C | 4 | 0 | 0 | 0 |
| | D | 8 | 0 | 0 | 0 |
| 2 | E | 0 | 1 | 0 | 0 |
| | F | 0 | 2 | 0 | 0 |
| | G | 0 | 4 | 0 | 0 |
| | H | 0 | 8 | 0 | 0 |
| 3 | I | 0 | 0 | 1 | 0 |
| | J | 0 | 0 | 2 | 0 |
| | K | 0 | 0 | 4 | 0 |
| | L | 0 | 0 | 8 | 0 |
| 4 | M | 0 | 0 | 0 | 1 |
| | N | 0 | 0 | 0 | 2 |
| | O | 0 | 0 | 0 | 4 |
| | P | 0 | 0 | 0 | 8 |
| | | 15 | 15 | 15 | 15 |

The method presented above, and exemplified in Table 8, may be extended by introducing additional colors and/or intensities. For example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or more colors may be used. Additional intensity levels, such as 16, 32, 64, 128, 255, 512, 1024, 2048, 4096, 8192, 16384, 32768, 65536, and so on may also be used. The method is generalizable and may be used to encode an infinite number of analytes. Each analyte is represented by a code in a single color, wherein the value of the code in that single color equal to the sum of all previous values plus one. For example, if the first code contains a 1 in a particular color, the next codes are 2, 4, 8, 16, 32, 64, 128 and so on. Other progressions are possible, but will not be as efficient in terms of usage of the bandwidth. However, one of ordinary skill in the art will recognize that less efficient use of bandwidth may be desirable when one wishes to maximize separation between values. Similarly, the value 1 could be excluded from the coding scheme, for example to maximize the difference in the intensity between the first encoded value and instrumental noise. For example, in some cases a coding scheme may begin with a value of 2, which would provide a progression of 2, 4, 8, 16, 32, 64, 128, and so on for the analyte codes, while the progression of cumulative results would be 2, 4, 6, 8, 10, 12, 14, 16, and so on. This approach generates uniform gaps in the possible cumulative results, allowing for higher tolerance to noise in comparison to an analyte code progression of 1, 2, 4, 8, 16, 32, and so on, and its corresponding cumulative result progression of 1, 2, 3, 4, 5, 6, 7, 8, and so on. In this example, the increased robustness in the measurement comes at a cost of a decrease in the number of available codes within a fixed bandwidth of multiplicity. For example, if only 63 multiplicity states can be measured reliably, the coding scheme starting with 1 offers 7 codes per color whereas the coding scheme starting with 2 offers 6 codes per color. If 4 colors are available, the former will offer 28 codes, while the latter will offer 24 codes. In summary, both the starting signal intensity and the progression (i.e., difference between intensity values) may be scaled in order to maximize the ability to distinguish over instrumental noise and maximize the differences between the intensity values, thereby enhancing the ability to distinguish between distinct experimental outcomes.

The coding scheme illustrated in Table 8 is non-degenerate by design. Although the coding scheme illustrated in Table 8 uses both intensity and color to encode each of the 16 analytes, each of the analytes could also be encoded by simply utilizing intensity. For example, given the 16 analytes provided in Table 8 (A-P), a single color coding scheme encoding all 16 analytes may assign the values 1, 2, 4, 8, 16, 32, 64, 128, 256, 512, 1024, 2048, 4096, 8192, and 16384 to analytes A, B, C, D, E, F, G, H, I, J, K, L, M, N, O, and P, respectively. Such a coding scheme is non-degenerate by design and the cumulative intensity result can be unambiguously decoded to indicate the presence or absence of analytes A-P. This coding scheme is capable of detecting the presence or absence of M analytes, where $M=\log_2 (F+1)$ and F is the maximum cumulative value of a signal (e.g., signal intensity). By adding a second component to this signal (e.g., color, as depicted in Table 8), the capacity of this coding scheme can be increased to $M=C*\log_2 (F+1)$, where C is the number of colors used in said coding scheme.

As described throughout this specification, any suitable value may be used for C or F. For example, C may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or more. F may be at least about 2, 4, 8, 16, 32, 64, 128, 255, 512, 1024, 2048, 4096, 8192, 16384, 32768, 65536, 131072, 262144, 524288, 1048576, and so on. As described elsewhere in this disclosure, both the initial starting value of F and the steps in its progression may also be varied.

III. Analytes

An analyte may be any suitable analyte that may be analyzed using the methods and compositions of the invention, where the analyte is capable of interacting with a reagent in order to generate a signal with at least two components that can be measured. An analyte may be naturally-occurring or synthetic. An analyte may be present in a sample obtained using any methods known in the art. In some cases, a sample may be processed before analyzing it for an analyte. The methods and compositions presented in this disclosure may be used in solution phase assays, without the need for particles (such as beads) or a solid support.

In some cases, an analyte may be a polynucleotide, such as DNA, RNA, peptide nucleic acids, and any hybrid thereof, where the polynucleotide contains any combination of deoxyribo- and/or ribo-nucleotides. Polynucleotides may be single stranded or double stranded, or contain portions of both double stranded or single stranded sequence. Polynucleotides may contain any combination of nucleotides or bases, including, for example, uracil, adenine, thymine, cytosine, guanine, inosine, xanthine, hypoxanthine, isocytosine, isoguanine and any nucleotide derivative thereof. As used herein, the term "nucleotide" may include nucleotides and nucleosides, as well as nucleoside and nucleotide analogs, and modified nucleotides, including both synthetic and naturally occurring species. Polynucleotides may be any suitable polynucleotide for which one or more reagents (or probes) as described herein may be produced, including but not limited to cDNA, mitochondrial DNA (mtDNA), messenger RNA (mRNA), ribosomal RNA (rRNA), transfer RNA (tRNA), nuclear RNA (nRNA), small interfering RNA (siRNA), small nuclear RNA (snRNA), small nucleolar RNA (snoRNA), small Cajal body-specific RNA (scaRNA), microRNA (miRNA), double stranded (dsRNA), ribozyme, riboswitch or viral RNA. Polynucleotides may be contained within any suitable vector, such as a plasmid, cosmid, fragment, chromosome, or genome.

Genomic DNA may be obtained from naturally occurring or genetically modified organisms or from artificially or synthetically created genomes. Analytes comprising genomic DNA may be obtained from any source and using any methods known in the art. For example, genomic DNA may be isolated with or without amplification. Amplification may include PCR amplification, multiple displacement amplification (MDA), rolling circle amplification and other amplification methods. Genomic DNA may also be obtained by cloning or recombinant methods, such as those involving plasmids and artificial chromosomes or other conventional methods (see Sambrook and Russell, *Molecular Cloning: A Laboratory Manual.*, cited supra.) Polynucleotides may be isolated using other methods known in the art, for example as disclosed in *Genome Analysis: A Laboratory Manual Series* (Vols. I-IV) or *Molecular Cloning: A Laboratory Manual*. If the isolated polynucleotide is an mRNA, it may be reverse transcribed into cDNA using conventional techniques, as described in Sambrook and Russell, *Molecular Cloning: A Laboratory Manual.*, cited supra.

An analyte may be a protein, polypeptide, lipid, carbohydrate, sugar, small molecule, or any other suitable molecule that can be detected with the methods and compositions provided herein. An analyte may be an enzyme or other protein. An analyte may be a drug or metabolite (e.g., anti-cancer drug, chemotherapeutic drug, anti-viral drug, antibiotic drug, or biologic). An analyte may be any molecule, such as a co-factor, receptor, receptor ligand, hormone, cytokine, blood factor, antigen, steroid, or antibody.

An analyte may be any molecule from any pathogen, such as a virus, bacteria, parasite, fungus, or prion (e.g., PrP$^{Sc}$). Examples of viruses include those from the families Adenoviridae, Flaviviridae, Hepadnaviridae, Herpesviridae, Orthomyxoviridae, Papovaviridae, Paramyxoviridae, Picornaviridae, Polyomavirus, Retroviridae, Rhabdoviridae, and Togaviridae. Specific examples of viruses include adenovirus, astrovirus, bocavirus, BK virus, coxsackievirus, cytomegalovirus, dengue virus, Ebola virus, enterovirus, Epstein-Barr virus, feline leukemia virus, hepatitis virus, hepatitis A virus, hepatitis B virus, hepatitis C virus, hepatitis D virus, hepatitis E virus, herpes simplex virus (HSV), HSV type 1, HSV type 2, human immunodeficiency virus (HIV), HIV type 1, HIV type 2, human papilloma virus (HPV), HPV type 1, HPV type 2, HPV type 3, HPV type 4, HPV type 6, HPV type 10, HPV type 11, HPV type 16, HPV type 18, HPV type 26, HPV type 27, HPV type 28, HPV type 29, HPV type 30, HPV type 31, HPV type 33, HPV type 34, HPV type 35, HPV type 39, HPV type 40, HPV type 41, HPV type 42, HPV type 43, HPV type 44, HPV type 45, HPV type 49, HPV type 51, HPV type 52, HPV type 54, HPV type 55, HPV type 56, HPV type 57, HPV type 58, HPV type 59, HPV type 68, HPV type 69, influenza virus, JC virus, Marburg virus, measles virus, mumps virus, Norwalk virus, parovirus, polio virus, rabies virus, respiratory syncytial virus, retrovirus, rhinovirus, rotavirus, Rubella virus, smallpox virus, vaccinia virus, West Nile virus, and yellow fever virus.

Examples of bacteria include those from the genuses *Bordetella, Borrelia, Brucella, Campylobacter, Chlamydia, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, and *Yersinia*. Specific examples of bacteria include *Bordetella par apertussis, Bordetella pertussis, Borrelia burgdorferi, Brucella abortus, Brucella canis, Brucella melitensis, Brucella suis, Campylobacter jejuni, Chlamydia pneumoniae, Chlamydia psittaci, Chlamydia trachomatix, Clostridium botulinum, Clostridium difficile, Clostridium perfringens, Clostridium tetani, Corynebacterium diphtherias, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella choleraesuis, Salmonella dublin, Salmonella enteritidis, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Yersinia pestis*, and *Yersinia enterocolitica*.

Examples of parasites include those from the genuses *Acanthamoeba, Babesia, Balamuthia, Balantidium, Blasocystis, Cryptosporidium, Dientamoeba, Entamoeba, Giardia, Isospora, Leishmania, Naegleria, Pediculus, Plasmodium, Rhinosporidium, Sarcocystis, Schistosoma, Toxoplasma, Trichomonas*, and *Trypanosoma*. Specific examples of parasites include *Babesia divergens, Babesia bigemina, Babesia equi, Babesia microfti, Babesia duncani, Balamuthia mandrillaris, Balantidium coli, Dientamoeba fragilis, Entamoeba histolytica, Giardia lamblia, Isospora belli, Naegleria fowleri, Pediculus humanus, Plasmodium falciparum, Plasmodium knowlesi, Plasmodium malariae, Plasmodium ovale, Plasmodium vivax, Rhinosporidium seeberi, Sarcocystis bovihominis, Sarcocystis suihominis, Schistosoma mansoni, Toxoplasma gondii, Trichomonas vaginalis, Trypanosoma brucei*, and *Trypansoma cruzi*.

Examples of fungi include those from the genuses *Apophysomyces, Aspergillus, Blastomyces, Candida, Cladosporium, Coddidioides, Cryptococcos, Exserohilum, Fusarium, Histoplasma, Pichia, Pneumocystis, Saccharomyces, Sporothrix, Stachybotrys*, and *Trichophyton*. Specific examples of fungi include *Aspergillus fumigatus, Aspergillus flavus, Aspergillus clavatus, Blastomyces dermatitidis, Candida albicans, Coccidioides immitis, Crytptococcus neoformans, Exserohilum rostratum, Fusarium verticillioides, Histoplasma capsulatum, Pneumocystis jirovecii, Sporothrix schenckii, Stachybotrys chartarum*, and *Trichophyton mentagrophytes*.

In some cases, the methods provided in this disclosure may be used to detect any one of the analytes described above, or elsewhere in the specification. In some cases the methods provided in this disclosure may be used to detect panels of the analytes described above, or elsewhere in the specification. For example, a panel may comprise an analyte selected from the group consisting of any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more analytes described above or elsewhere in the specification.

An analyte may be obtained from any suitable location, including from organisms, whole cells, cell preparations and cell-free compositions from any organism, tissue, cell, or environment. Analytes may be obtained from environmental samples, biopsies, aspirates, formalin fixed embedded tissues, air, agricultural samples, soil samples, petroleum samples, water samples, or dust samples. In some instances, an analyte may be obtained from bodily fluids which may include blood, urine, feces, serum, lymph, saliva, mucosal secretions, perspiration, central nervous system fluid, vaginal fluid, or semen. Analytes may also be obtained from manufactured products, such as cosmetics, foods, personal care products, and the like. Analytes may be the products of experimental manipulation including, recombinant cloning, polynucleotide amplification, polymerase chain reaction (PCR) amplification, purification methods (such as purification of genomic DNA or RNA), and synthesis reactions.

More than one type of analyte may be detected in each multiplexed assay. For example, a polynucleotide, a protein, a polypeptide, a lipid, a carbohydrate, a sugar, a small molecule, or any other suitable molecule may be detected simultaneously in the same multiplexed assay with the use of suitable reagents. Any combination of analytes may be detected at the same time.

Detection of an analyte may be useful for any suitable application, including research, clinical, diagnostic, prognostic, forensic, and monitoring applications. Exemplary applications include detection of hereditary diseases, identification of genetic fingerprints, diagnosis of infectious diseases, cloning of genes, paternity testing, criminal identification, phylogeny, anti-bioterrorism, environmental surveillance, and DNA computing. For example, an analyte may be indicative of a disease or condition. An analyte may be used to make a treatment decision, or to assess the state of a disease. The presence of an analyte may indicate an infection with a particular pathogen, or any other disease, such as cancer, autoimmune disease, cardiorespiratory disease, liver disease, digestive disease, and so on. The methods provided herein may thus be used to make a diagnosis and to make a clinical decision based on that diagnosis. For example, a result that indicates the presence of a bacterial polynucleotide in a sample taken from a subject may lead to the treatment of the subject with an antibiotic.

In some cases the methods and compositions of the invention may be used to detect at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, or 1000 analytes. In some cases the methods and compositions of the invention may be used to detect 7-50, 8-40, 9-30, 10-20, 10-15, 8-12, or 7-12 analytes.

In some cases, this disclosure provides assays that are capable of unambiguously detecting the presence or absence of each of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, or 1000 analytes, in any combination of presence or absence, in a single sample volume without immobilization, separation, mass spectrometry, or melting curve analysis. In some cases, this disclosure provides assays that are capable of unambiguously detecting the presence or absence of each of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, or 1000 analytes, in any combination of presence or absence, in a single sample volume without immobilization, separation, mass spectrometry, or melting curve analysis. In some cases, this disclosure provides assays that are capable of unambiguously detecting the presence or absence of less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, or 1000 analytes, in any combination of presence or absence, in a single sample volume without immobilization, separation, mass spectrometry, or melting curve analysis.

IV. Signals

The methods presented in this disclosure may be used with any quantifiable signal. In some cases, this disclosure provides coding schemes and methods to encode an infinite number of targets without degeneracy, using a single component of a signal (e.g., intensity). For example, as described above and in Example 3, a coding scheme may rely on a multiplicity of signal intensity without consideration of color. Although fluorescent probes have been used to illustrate this principle, the coding scheme is equally applicable to any other method providing a quantifiable signal, including an electrochemical signal and a chemiluminescent signal, as described elsewhere in this disclosure.

The methods presented in this disclosure may also utilize the measurement of a signal in at least two dimensions, also referred to as the measurement of at least two components of a signal. In comparison to the coding scheme described in the paragraph above, which relies on, for example, signal intensity to differentiate between analytes, utilization of at least two components of a signal (e.g., color and intensity) allows the generation of more unique codes per unit of signal intensity bandwidth. When at least two components of a signal are utilized, a cumulative measurement of the at least two components may be obtained for a single sample volume. For example in the coding scheme described in Table 5, the presence of each analyte results in a particular intensity (one component of the signal) in each of the four colors (a second component of a signal). The combination of these constituent signals leads to a cumulative signal that may be measured by measuring an intensity at each wavelength or range of wavelengths. The corresponding coding scheme or decoding matrix may then be used to convert the cumulative measurement into a determination of the presence or absence of an analyte.

In some cases, a quantifiable signal comprises a waveform that has both a frequency (wavelength) and an amplitude (intensity). A signal may be an electromagnetic signal. An electromagnetic signal may be a sound, a radio signal, a microwave signal, an infrared signal, a visible light signal, an ultraviolet light signal, an x-ray signal, or a gamma-ray signal. In some cases, an electromagnetic signal may be a fluorescent signal, for example a fluorescence emission spectrum that may be characterized in terms of wavelength and intensity.

In certain portions of this disclosure, the signal is described and exemplified in terms of a fluorescent signal. This is not meant to be limiting, and one of ordinary skill in the art will readily recognize that the principles applicable to the measurement of a fluorescent signal are also applicable to other signals. For example, like fluorescent signals, any of the electromagnetic signals described above may also be characterized in terms of a wavelength and an intensity. The wavelength of a fluorescent signal may also be described in terms of color. The color may be determined based on measuring intensity at a particular wavelength or range of wavelengths, for example by determining a distribution of fluorescent intensity at different wavelengths and/or by utilizing a band pass filter to determine the fluorescence intensity within a particular range of wavelengths. Such band pass filters are commonly employed in a variety of laboratory instrumentation, including quantitative PCR machines. Intensity may be measured with a photodetector. A range of wavelengths may be referred to as a "channel."

In some cases, the methods provided in this disclosure may be used with any signal where the cumulative signal scales with the constituent signals of the same color, frequency, absorption band, and so on. However, the cumulative signal need not be digital or scale linearly with the number and intensity of the constituent signals. For example, if the physical principle of measurement is absorption, the cumulative attenuation is a product of constituent attenuations while the constituent concentrations are additive, due to the exponential nature of the Beer-Lambert law. The logarithm of the cumulative attenuation will then scale linearly with constituent concentrations in each absorption band (the equivalent of color, if fluorescent detection is used). The methods of the invention are therefore applicable. The methods of the invention may also be used with chemiluminescent signals and electrochemical signals.

The number of signals, and the number of dimensions or components measured, may also be expanded beyond the numbers shown in the exemplary embodiments of the invention, leading to an expansion in multiplexing capability. The exemplary embodiments provided in this disclosure utilize coding schemes constructed utilizing a fluorescent signal with one or two components measured: wavelength and/or intensity. The number of analytes that can be encoded can be increased by increasing the number of wavelengths and/or intensities. The number of analytes that can be encoded can also be increased by increasing the number of signals, for example by combining a fluorescent signal with an electrochemical signal or a FRET signal (fluorescence resonance energy transfer).

In some cases, more than two components of a signal may be measured. For example, 3, 4, 5, 6, 7, 8, 9, 10, 11, 12, 13, 14, 15, 16, 17, 18, 18, 20 or more components of a signal may be measured. At least 2, 3, 4, 5, 6, 7, 8, 9, 10, 11, 12, 13, 14, 15, 16, 17, 18, 18, or 20 components of a signal may be measured. At least 2, but fewer than 3, 4, 5, 6, 7, 8, 9, 10, 11, 12, 13, 14, 15, 16, 17, 18, 18, or 20 components of a signal may be measured. In some cases, 2-3, 2-4, 2-5, 2-6, 3-5, 3-6, 3-8, or 5-10 components of a signal may be measured. These additional components may include kinetic components, such as a rate of signal decay and rate of photobleaching.

If a fluorescent signal is employed, the number of analytes that can be encoded may be further expanded by utilizing additional fluorophores. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more fluorophores may be used. In some cases, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores may be used. In some cases, fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores may be used. In some cases, 4-6, 4-7, 4-8, 4-9, 4-10, 5-6, 5-7, 5-8, 5-9, 5-10, 10-15, or 10-20 fluorophores may be used.

Generally, the number of analytes that can be encoded may be further expanded by utilizing additional first values (e.g., intensities) that are values or ranges of values from a first component of a signal. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more first values that are values or ranges of values from a first component of a signal may be used. In some cases, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more first values that are values or ranges of values from a first component of a signal may be used. In some cases, fewer than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 first values that are values or ranges of values from a first component of a signal may be used. In some cases, 4-20, 4-6, 4-7, 4-8, 4-9, 4-10, 5-6, 5-7, 5-8, 5-9, 5-10, 10-15, or 10-20 first values that are values or ranges of values from a first component of a signal may be used.

In instances in which intensity is a component of a signal that is quantified, such as when a fluorescent signal is utilized, the presence of an analyte may be encoded using a variety of intensities or ranges of intensities. For example, a coding scheme may utilize 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more intensities or ranges of intensities. A coding scheme may utilize at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more intensities or ranges of intensities. A coding scheme may utilize fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 intensities or ranges of intensities. In some cases, a coding scheme may utilize 2-20, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, or 5-10 intensities or ranges of intensities.

The number of analytes that can be encoded may be further expanded by utilizing additional second values (e.g., wavelengths) that are values or ranges of values from a second component of a signal. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more second values that are values or ranges of values from a second component of a signal may be used. In some cases, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more second values that are values or ranges of values from a second component of a signal may be used. In some cases, fewer than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 second values that are values or ranges of values from a second component of a signal may be used. In some cases, 4-20, 4-6, 4-7, 4-8, 4-9, 4-10, 5-6, 5-7, 5-8, 5-9, 5-10, 10-15, or 10-20 second values that are values or ranges of values from a second component of a signal may be used.

In instances in which wavelength is a component of a signal that is quantified, such as when a fluorescent signal is utilized, the presence of an analyte may be encoded using a variety of wavelengths or ranges of wavelengths. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more wavelengths or ranges of wavelengths may be used. In some cases, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more wavelengths or ranges of wavelengths may be used. In some cases, fewer than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wavelengths or ranges of wavelengths may be used. In some cases, 4-20, 4-6, 4-7, 4-8, 4-9, 4-10, 5-6, 5-7, 5-8, 5-9, 5-10, 10-15, or 10-20 wavelengths or ranges of wavelengths may be used.

In some cases, when degeneracy is eliminated, the methods of the invention are capable of detecting the presence or absence of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more analytes in a single volume when each reagent used to generate a signal in the volume generates only one second value (e.g., each reagent, emits light at only one wavelength).

In other cases, when degeneracy is eliminated, the methods of the invention are capable of detecting the presence or absence of at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more analytes in a single volume using a total of four second values in that volume (e.g., a total of four wavelengths or ranges or wavelengths, which might be implemented by using four spectrally resolvable fluorophores).

As described throughout the specification, the assay provided herein utilizes cumulative measurements on a sample. A cumulative measurement may be, for example, a single measurement of intensity values, or a measurement of intensity values at one or more wavelengths or ranges of wavelengths. A plurality of cumulative measurements may be obtained. For example, an intensity may be measured at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more wavelengths or ranges of wavelengths. An intensity may be measured at at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more wavelengths or ranges of wavelengths. An intensity may be measured at less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wavelengths or ranges of wavelengths.

More generally a cumulative measurement may be obtained for any quantifiable component of a signal, and for any quantifiable component of a signal at another quantifiable component of a signal. For example, at least a first component of a signal may be measured at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more second components of a signal. At least a first component of a signal may be measured at at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more second components of a signal. At least a first component of a signal may be measured at less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 second components of a signal.

As is apparent from this disclosure, each analyte to be detected can be encoded as a code utilizing any number of suitable components of a signal or any number of signals. For example, each analyte to be detected can be encoded in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more components of a signal or signals. In some cases, each analyte to be detected can be encoded in at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more components of a signal or signals. In some cases, each analyte to be detected can be encoded in fewer than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 components of a signal or signals. In some cases, 1-4, 4-20, 4-6, 4-7, 4-8, 4-9, 4-10, 5-6, 5-7, 5-8, 5-9, 5-10, 10-15, or 10-20 components of signal or signals may be used to encode each analyte. Each analyte in a coding scheme may be encoded by the same number of components of a signal, or signals, or different numbers of components of a signal, or signals.

A. Probes, Primers, Fluorophores, and Quenchers

Some of the methods provided in this disclosure utilize a reagent that generates a signal in the presence of an analyte. Any suitable reagent may be used with the invention. Generally, a reagent will have an analyte-specific component and a component that generates a signal in the presence of the analyte. In some cases, these reagents are referred to as probes. The probes may be hybridization probes. The hybridization probes may be an oligonucleotide probe attached to a fluorophore and a quencher (e.g., a TAQMAN probe).

The methods of the invention may use one or more reagents or probes to detect the presence or absence of each analyte. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more or probes may be used to detect the presence or absence of each analyte. In some cases, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 probes may be used to detect the presence or absence of each analyte. In some cases, fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 probes may be used to detect the presence or absence of each analyte. In some cases, the number of probes used to detect the presence or absence of each analyte is 1-10, 2-9, 2-8, 2-7, 2-6, 2-5, 2-4, 1-3, or 1-4.

In some cases, a sample is contacted with 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more probes to detect the presence or absence of all analytes. In some cases, a sample is contacted with at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more probes to detect the presence or absence of all analytes. In some cases, a sample is contacted with fewer than 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 probes to detect the presence or absence of all analytes. In some cases, the number of probes that a sample is contacted with to detect the presence or absence of all analytes is 4-50, 4-40, 4-30, 4-20, 5-15, 5-10, or 3-10.

As described above, oligonucleotide probes attached to a fluorophore and a quencher may be used to detect the presence of an analyte in a polynucleotide amplification assay. So long as the quencher and the fluorophore are in proximity, the quencher quenches the fluorescence emitted by the fluorophore upon excitation by a light source. The sequence of the oligonucleotide probe is designed to be complementary to a polynucleotide sequence present in an analyte, and therefore capable of hybridizing to the polynucleotide sequence present in the analyte. Hybridization of the oligonucleotide probe may be performed in a nucleic acid amplification reaction comprising primers (e.g., a polymerase chain reaction). Upon extension of the primers by a DNA polymerase, the 5' to 3' exonuclease activity of the polymerase degrades the probe, releasing the fluorophore and the quencher into the medium. The proximity between the fluorophore and the quencher is broken and the signal from the fluorophore is no longer quenched. Thus, the amount of fluorescence detected is a function of the amount of analyte present. If no analyte is present, the probe will not hybridize to an analyte, and the fluorophore and quencher will remain in close proximity. Little or no signal will be produced.

Oligonucleotide probes may have one or a plurality of fluorophores and quenchers per probe. For example, in some embodiments an oligonucleotide probe may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more fluorophores. An oligonucleotide probe may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores. An oligonucleotide probe may comprise fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores.

An oligonucleotide probe may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more quenchers. An oligonucleotide probe may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 quenchers. An oligonucleotide probe may comprise fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 quenchers.

Attachment of probes and quenchers to a probe may be performed in the same reaction or in serial reactions. A series of reactions may be performed to label probes with at least one fluorophore and the reaction products may be mixed to generate a mixture of probes with different fluorophores.

If an oligonucleotide probe comprises two or more fluorophores, these fluorophores may be arranged to allow Förster (Fluorescence) resonance energy transfer (FRET) to occur between the fluorophores. Briefly, FRET is a mechanism of energy transfer between fluorophores. Using FRET-based probes allows one excitation source to generate two different fluorescence emission signals by excitation of a single fluorophore. For example, the methods described herein may used paired probes, where one probe in the pair is attached to a fluorophore and a quencher and a second probe is attached to two fluorophores (in close enough proximity for FRET to occur) and a quencher. Any combination of fluorophores and quenchers that provide for FRET may be used. Such an approach doubles the number of fluorescent probes that may be used with an excitation source, because a single excitation source can be used to produce two signals: one from the probe with one fluorophore and one from the probe with two fluorophores in close enough proximity to provide for FRET. For example, using the encoding method described in Table 8, the number of unambiguously detectable analytes could be increased from 16 to 32 by pairing each of the probes in Table 8 with a corresponding FRET probe.

The primers may be specific for a particular analyte and capable of amplifying a region complementary to a probe. In some cases, the number of pairs of primers used is equivalent to the number of probes. In other cases, the number of probes used may exceed the number of primer pairs used. In still other cases, the number of primer pairs used may exceed the number of probes used. In some cases a sample to be analyzed is contacted with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more pairs of primers. In some cases a sample to be analyzed is contacted with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more pairs of primers. In some cases a sample to be analyzed is contacted with fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 pairs of primers. In some cases, the number of pairs of primers is 2-10, 3-15, 4-20, 3-10, 4-10, 5-10, 6-8, or 6-10.

The primers may amplify regions of a polynucleotide in which different numbers of hybridization probes hybridize. For example, at least one pair of primers may amplify a region complementary to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 hybridization probes. In some cases, all of said pairs of primers may amplify a region complementary to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 hybridization probes.

In one example, a first probe may be labeled with the fluorophore 5'-fluorescein amidite (5'-FAM) and the quencher black hole quencher 1 (BHQ-1). A second probe may be labeled with 5'-FAM in close proximity (e.g., attached to) to cyanine 5.5 (Cy5.5) and the quencher black hole quencher 3 (BHQ-3). Upon digestion of the probe, via the nuclease activity of the polymerase, two fluorescent signals are generated from a single excitation wavelength (e.g., 470 nm). The fluorophore from the first probe will fluoresce at about 520 nm. The fluorophores on the second probe undergo FRET. The donor fluorophore, FAM is excited by the excitation light source (e.g., 470 nm) and transfers its energy to the acceptor fluorophore, Cy5.5. The acceptor fluorophore emits at about 705 nm. These fluorophores and quenchers are merely exemplary. Any fluorophores that can undergo FRET and any quenchers that can quench fluorescence are suitable for use with the invention. Methods for producing FRET-based probes are described in Jothikumar et al., BioTechniques, 2009, 46(7):519-524.

In some examples, a single hybridization probe may be used for each analyte. In order to utilize multi-color encoding (e.g., as shown in Table 3), each probe may be labeled with a plurality of fluorophores at pre-determined ratios. The ratio may be determined so that a positive control signal provides the same intensity as other positive control signals of the same intensity, in the same color. This approach reduces the number of probes that must be synthesized and may be less expensive to deploy than methods utilizing multiple probes. Moreover, in the case of hybridization probes, it is easier to fit one hybridization probe to an analyte sequence than multiple probes.

Although many aspects of the invention are exemplified using nucleic acid-based probes, one of ordinary skill in the art will readily recognize that other forms of probes would work equally well with the invention described in this disclosure. For example, a binding molecule specific to an analyte could be used as a probe. Non-limiting exemplary binding molecules include an antibody recognizing an analyte, and generating a signal in the presence of an analyte.

In embodiments of the invention that utilize fluorescent labels, any suitable fluorescent label may be used. Exemplary fluorescent labels suitable for use with the invention include rhodamine, rhodol, fluorescein, thiofluorescein, aminofluorescein, carboxyfluorescein, chlorofluorescein, methylfluorescein, sulfluorescein, aminorhodol, carboxyrhodol, chlororhodol, methylrhodol, sulforhodol; aminorhodarnine, carboxyrhodarnine, chlororhodamine, methylrhodarnine, sulforbodamine, and thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, and bilirubin. Exemplary quenchers include black hole quenchers, such as BHQ-0, BHQ-1, BHQ-2, BHQ-3; ATTO quenchers, such as ATTO 540Q, ATTO 580Q, and ATTO612Q; and the like.

The fluorophores that may be used with the invention are not limited to any of the fluorophores described herein. For example, fluorophores with improved properties are continually developed, and these fluorophores could readily be used with the methods provided in this disclosure. Such improved fluorophores include quantum dots, which may emit energy at different wavelengths after being excited at a single wavelength. The advantage of using such fluorophores is that only a single excitation source is needed, but many different signals may be quantified, for example in terms of color and intensity. Moreover, fluorophores with narrow emission spectra would be particularly useful with the method described herein, as such fluorophores could be included in multiplex assays with minimal or no overlap between their emission spectra, thereby offering many more "colors" and boosting significantly the overall number of coded analytes.

In some cases, one or more reagents are lyophilized. Any suitable reagent may be lyophilized. For example, probes, primers, enzymes, antibodies, or any other reagent used for detection may be lyophilized. In some cases, a sample comprising an analyte may also be lyophilized. Lyophilization may be useful, for example, when distributing reagents and/or samples in developing regions where access to cold storage is expensive, not readily available, or not reliably available. In one example, lyophilized reagents comprise any probe or analyte-specific reagent described in this disclosure or otherwise suitable for use with the invention. In another example, lyophilized reagents comprise PCR primers. In yet another example, lyophilized reagents comprise reagents suitable for performing a PCR reaction.

V. Analytical Techniques and Instrumentation

The methods provided herein are suitable for use with a variety of detection methods. For example, the methods may be applied using an analytical technique that measures the wavelength and intensity of a fluorescent signal. This may be accomplished by measuring the intensity of a signal across a spectrum of wavelengths, or by using band pass filters that restrict the passage of certain wavelengths of light, thereby allowing only light of certain wavelengths to reach a photodetector. Many real-time PCR and quantitative PCR instruments comprise an excitation light source and band pass filters that enable the detection of fluorescent signals in four colors (e.g., blue, green, yellow, and red). Therefore, the methods of the invention can be readily applied using instruments widely used in the art. Importantly, the methods and compositions provided herein may be used to detect multiple analytes by obtaining a cumulative measurement on a single solution. No separation is necessary. The invention does not require the use of beads or a solid phase. Of course, one of ordinary skill in the art would understand that the invention could be used with separation, beads, or a solid phase, if desired.

Figure 5:
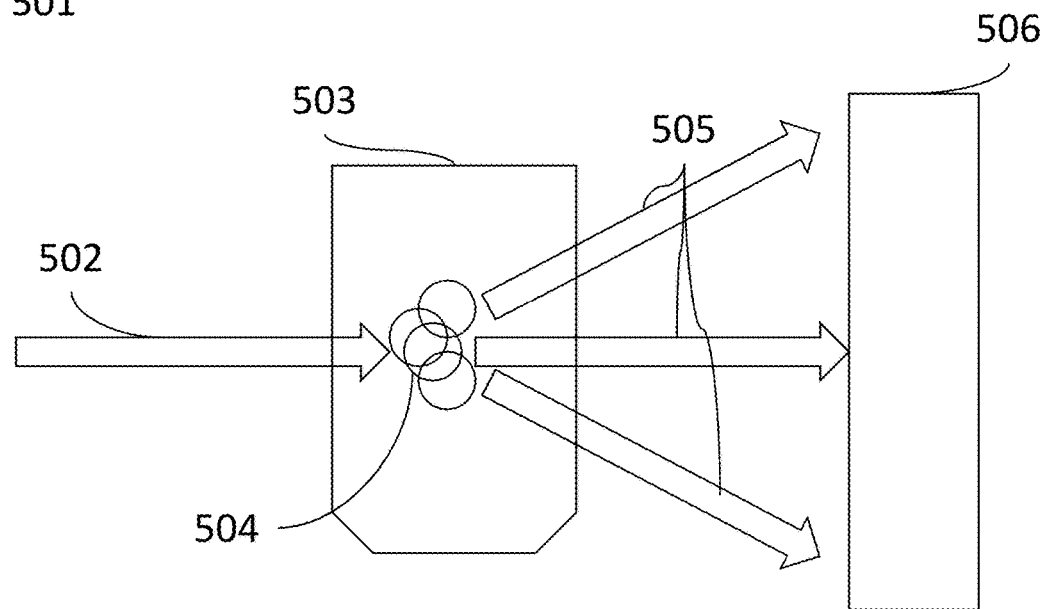
FIG. 5 shows a schematic of two different methods of detecting wavelength and intensity of a light signal, such as a fluorescence emission signal.
Figure 5:
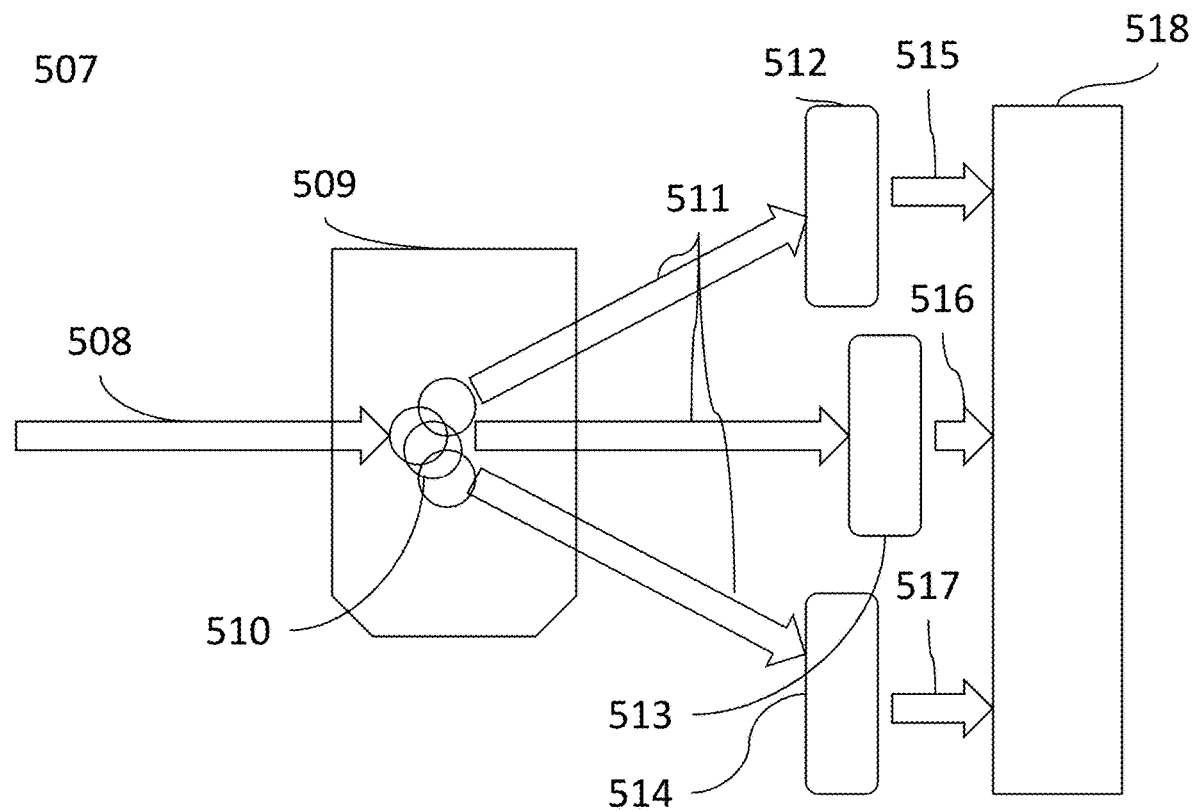

FIG. 5 shows two examples of instrumental configurations that may be used to obtain cumulative measurements useful for the methods of the invention. With reference to FIG. 5, an instrument with a detector configured to detect both wavelength and intensity (e.g., a fluorometer) is shown in 501. With reference to 501, at least one excitation light source 502 is directed into a chamber 503 containing analytes and reagents that generate a signal in the presence of the analytes 504. As described elsewhere, the analyte may be a nucleic acid and the reagents generating the signal may be hybridization probes comprising a fluorophore and a quencher. If the analyte is present, an emission signal 505 is generated. In the configuration shown in 501, the wavelength and intensity of this emission signal are measured across a spectrum by a detector capable of generating a fluorescence emission spectrum 506.

The wavelength and intensity may also be determined using a combination of a photodetector and band pass filters. This configuration is used in several thermal cyclers known in the art. With reference to FIG. 5, an instrument with band pass filters and a photodetector is depicted in 507. With reference to 507, at least one excitation light source 508 is directed into a chamber 509 containing analytes and reagents that generate a signal in the presence of the analytes 510. As described elsewhere, the analyte may be a nucleic acid and the reagents generating the signal may be hybridization probes comprising a fluorophore and a quencher. If the analyte is present, an emission signal 511 is generated. In the configuration shown in 507, band pass filters 512, 513, and 514 are used to restrict the passage of light to light within certain ranges of wavelengths. For example band pass filter 512 may restrict the passage of light to light within wavelength range 1. Band pass filter 513 may restrict the passage of light to light within wavelength range 2. Band pass filter 514 may restrict the passage of light to light within wavelength range 3. Any number of band pass filters (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) may be used with the invention. In addition, the positions of the band pass filters in 507 are not meant to be limiting. In some cases, emitted light may be passed through more than one band pass filter at any time. In other cases, the band pass filters may be configured so that all emitted light passes through only one band pass filter at a time. After passage through a band pass filter, filtered light 515, 516, and 517 is detected by a photodetector. For example, filtered light 515 may be light within wavelength range 1, filtered light 516 may be light within wavelength range 2, and filtered light 517 may be light within wavelength range 3. The intensity of each of the filtered lights 515, 516, and 517 may then be quantified by a photodetector 518.

The methods described in this disclosure are compatible with a variety of amplification methods, including quantitative PCR (qPCR) methods, end point PCR methods, reverse transcriptase PCR, and digital PCR methods. Digital PCR methods (e.g., DROPLET DIGITAL (BIORAD) and DYNAMIC ARRAY (FLUIDIGM)) produce highly sensitive quantification of polynucleotide copy numbers. The methods provided herein can be easily integrated into these systems to significantly expand their throughput by allowing multiplexing in a droplet or a dynamic array.

Similarly, the methods described in this disclosure may be applied in a real-time PCR assay. For example, real-time data may be fully recorded as the PCR runs to completion. The end-point values may then be decoded to indicate the presence or absence of analytes. The individual cycle thresholds (Ct) values may be analyzed for each color by detecting the maxima of the second derivative of the real-time curve in that color. As a particular analyte is amplified, fluorophores are released from its corresponding probes in the same ratios as the color multiplicities in the coding of that sequence. Hence, e.g. a code of 1100 will have the same Ct in blue and green, while a code of 1400 will have its green Ct precede its blue Ct by 2 cycles. This additional data enables determination of the identity and starting quantity of each analyte.

The methods described herein may also be used directly on a tissue sample. For example, a tissue sample may be obtained and photolithographic methods may be used to build wells directly onto the tissue sample. The tissue sample may be fixed prior to building the wells. The tissue sample may then be analyzed by dispensing appropriate reagents into the wells in the tissue sample. The encoding and decoding methods described in this disclosure may be used for the multiplexed detection of analytes within the wells etched into the tissue. Each well may correspond to a single cell or a few cells, providing excellent spatial resolution when analyzing different portions of a tissue for an analyte. This method may be used to detect analytes in different areas of the same tissue.

In some cases, instruments may be modified or constructed, for example, to provide additional excitation light sources, at multiple wavelength, and/or to provide additional band pass filters or a capability of determining a complete spectrum. Including additional excitation sources would allow for the excitation of a larger variety of fluorophores. Including additional band pass filters, or modifying or constructing an instrument capable of determining an entire spectrum allows detection of a wider variety of emissions from fluorophores. These techniques can be used to increase the number of fluorophores that can be used with the methods described in this disclosure and, accordingly, to increase the number of analytes that be simultaneously detected.

In some cases, the methods described in this disclosure utilize end-point PCR methods. However, in some cases a result may be obtained before the end-point. This may be advantageous when, for example, results are needed as soon as possible. For example, in one case calibration experiments are performed in which different starting concentrations of an analyte are analyzed to determine the cycle number at which the signal becomes saturated, as a function of the starting amount of the analyte. Using this data, a computer monitoring a PCR reaction in real-time can be programmed to search for saturation up to the maximal cycle number according to the limit of detection (LOD) of the particular system. If there is no amplification of an analyte (e.g., other than a positive control, if present), by the maximal cycle number, the result for that analyte is negative. If there is amplification of the analyte by the maximal cycle number, the result for that analyte is positive and the saturation intensity in each color may be used to decode the result using the coding scheme. In both cases, there would be no need to run the PCR reaction beyond the number of cycles set by the LOD for that instrument. Although PCR has been used to illustrate this quantitative method, one of ordinary skill in the art will readily recognize that similar principles could be applied in any catalytic system where the starting amount of an analyte limits the rate of reaction, and the rate of reaction can be measured and reported by an evolution in a signal intensity over time.

VI. Compositions and Kits

This disclosure also provides compositions and kits for use with the methods described herein. The compositions may comprise any component, reaction mixture and/or intermediate described herein, as well as any combination. For example, the disclosure provides detection reagents for use with the methods provided herein. Any suitable detection reagents may be provided, including hybridization probes labeled with a fluorophore and a quencher and primers, as described elsewhere in the specification.

In some cases, compositions comprise reagents for the detection of at least seven analytes using four fluorophores. In some cases, compositions comprise reagents for the detection of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes using four fluorophores. In some cases, compositions comprise reagents for the detection of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes using five fluorophores. In some cases, compositions comprise reagents for the detection of at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes using six fluorophores. In some cases, compositions comprise reagents for the detection of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes using seven fluorophores.

In some cases the compositions comprise primers. The compositions may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 pairs of primers.

The invention also provides kits for carrying out the methods of the invention. Accordingly, a variety of kits are provided in suitable packaging. The kits may be used for any one or more of the uses described herein, and, accordingly, may contain instructions for detecting the presence or absence of each analyte of a plurality of analytes. A kit may comprise a coding scheme, or a decoding matrix, to assist the user in converting a cumulative measurement to a result indicating the presence or absence of each of a plurality of analytes. A kit may be a diagnostic kit, for example, a diagnostic kit suitable for the detection of any analyte, including the analytes recited herein. A kit may contain any of the compositions provided in this disclosure, including those recited above.

Figure 6:
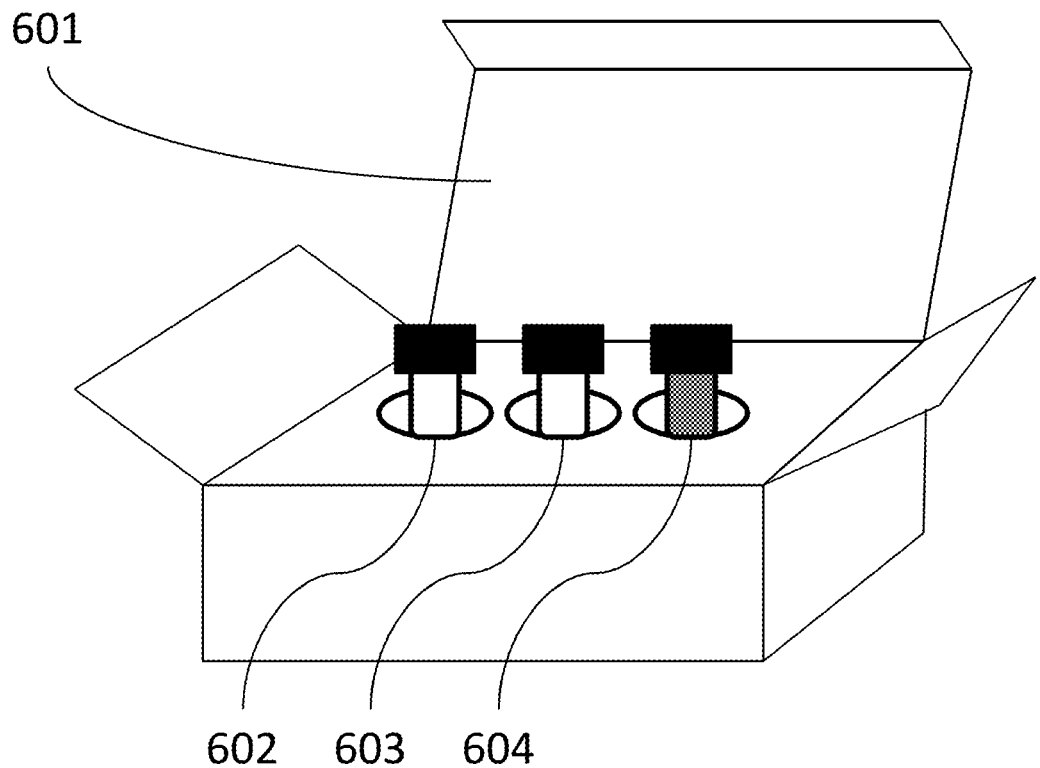
FIG. 6 shows a schematic of exemplary kits.
Figure 6:
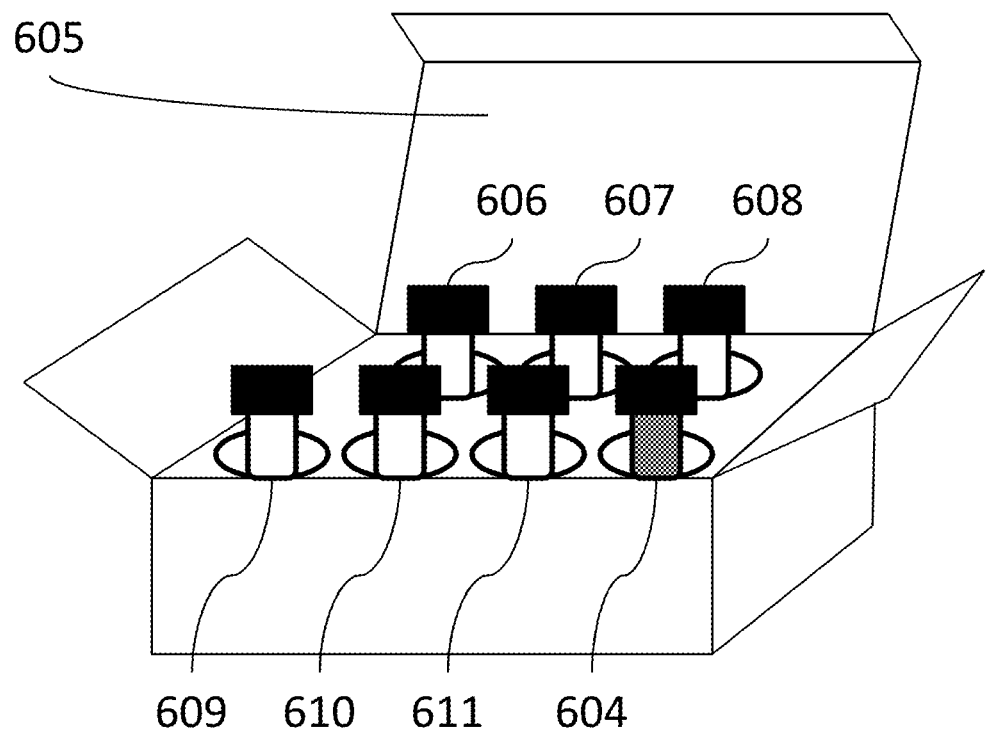

FIG. 6 shows schematics of exemplary kits of the invention. With reference to FIG. 6, a kit comprising a kit body 601 is shown that contains reagents for the detection of analytes (e.g., polynucleotide probes comprising a fluorophore and a quencher) 602 and primers for the amplification of a nucleic acid 603. The kit may also contain any other reagents, such as reagents suitable for performing an amplification reaction 604. In the embodiment depicted in 601, the reagents for the detection of analytes and the primers are each contained in a single volume (e.g., tube or a bottle). However, these reagents may also be provided in separate volumes, as depicted the kit body shown in 605. The kit body 605 contains seven separate volumes. Three volumes (606, 607, and 608) contain reagents for the detection of analytes (or mixtures of such reagents) and three volumes (609, 610, and 611) contain primers (or mixtures of primers). The kit may also contain reagents suitable for performing an amplification reaction 604.

FIG. 6 is provided for illustrative purposes only. Any number of reagents for the detection of analytes (e.g., probes) and any number of primers may be included in a single tube or bottle, as appropriate for the application. For example, in some embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more reagents for the detection of analytes may be included in a single bottle. In other cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more primers for amplification may be included in a single bottle or tube. In some cases, primers and probes may be provided in the same bottle or tube. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more probes may be provided per pair of primers. In other cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more primers may be provided per pair of probes. The kits may contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bottles or tubes. Control analytes, and their associated detection reagents and primers, may also be included in the kit. These may be included in a separate bottle or tube or, for example, included within the bottle or tube providing reagents for an amplification reaction 604. As described elsewhere in the specification, any reagent in the kits may be lyophilized.

VII. Systems and Software

Figure 4:
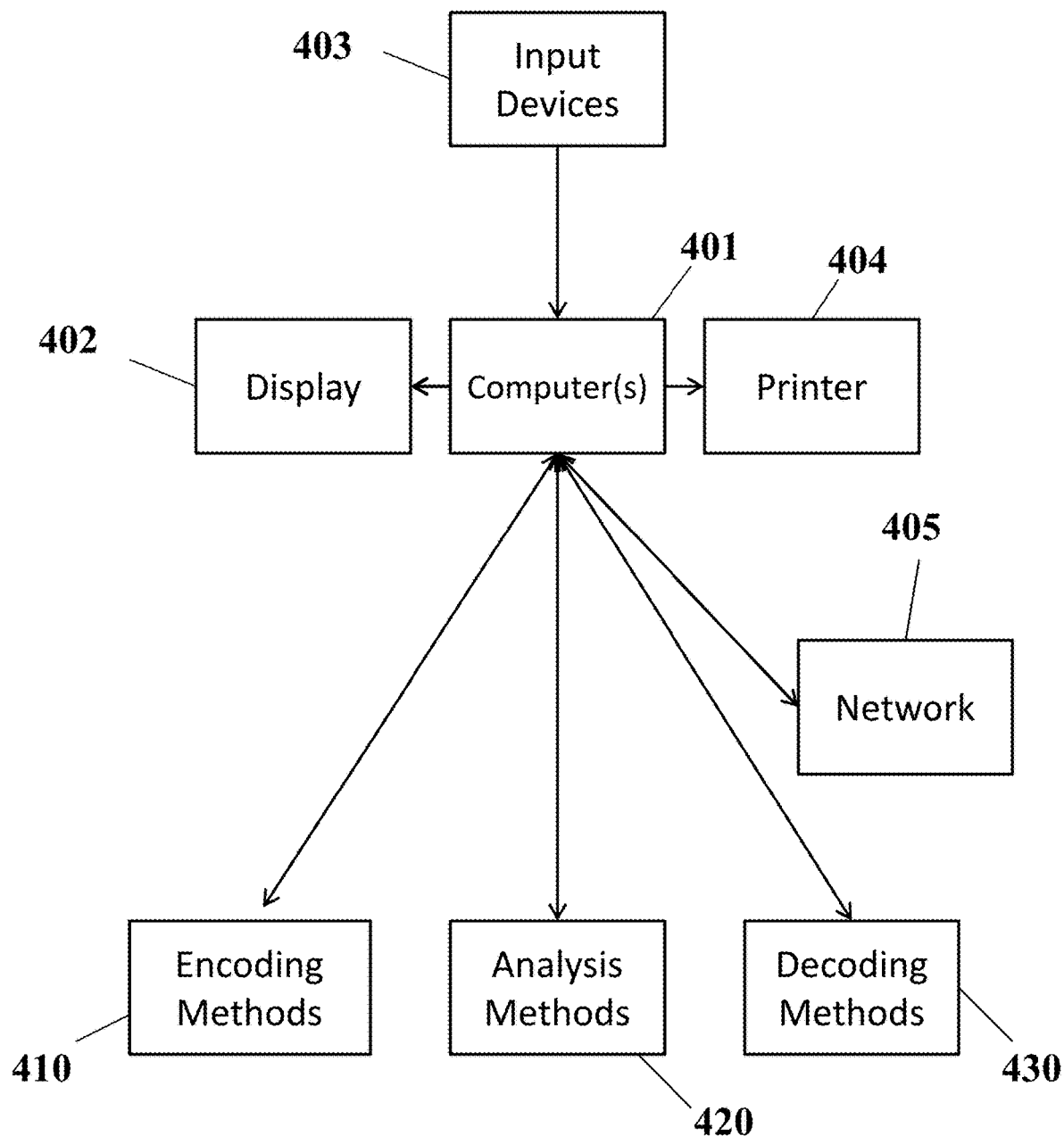
FIG. 4 shows an exemplary embodiment of the invention in which a computer is used to perform one or more steps of the methods provided herein.

The methods of this disclosure may also be performed as part of a system. For example, one or more steps of the methods described herein may be performed by software contained on a computer readable medium. The software may be used to encode analytes, check for degeneracy, reduce or eliminate degeneracy, and/or produce a decoding matrix. The software may also be used to convert cumulative measurements made on an instrument (e.g., a PCR machine) into information concerning the presence or absence of an analyte. For example, with reference to FIG. 4, a computer 401 may be connected to an input device 403, a display 402, and a printer 404. The computer may execute one or more of the steps of any of the methods described in this disclosure, including, for example, encoding methods 410, analysis methods 420, and decoding methods 430. A computer may reduce or eliminate degeneracy, for example as part of the encoding methods 410. Similarly, a computer may generate a coding scheme that is non-degenerate by design using, for example, mathematical iteration. A computer may also be connected to a network 405. The network may be a local network and/or the Internet. The network may be used to perform the methods of the invention on multiple computers in different locations. For example, one computer may perform the encoding, another computer may perform the measuring, and yet another computer may perform the decoding. A computer may perform any or all of these methods. The network may be used to transmit information obtained using the methods described in this disclosure throughout the world, for example across a border.

In one example, the software is embedded in the instrument making the measurement, such as a thermal cycler. In another example, the software is installed on a computer attached to the instrument making the measurement, such as a computer attached to a thermal cycler. In another example, the software is in the "cloud"—i.e., on a computer that another computer may communicate with through a network.

Each of the elements described above may be connected to a controller that communicates with each of the elements and coordinates their actions. For example, a controller may initiate the encoding of a series of analytes into values of color and intensity. As described throughout this disclosure, the controller can execute software to reduce or eliminate degeneracy by removing one or more potential analyte codes from the encoding matrix. The controller may then automatically order probes corresponding to this code from a manufacturer of probes. Alternatively, the controller may operate an oligonucleotide synthesis instrument that can synthesize the appropriate probes. After analysis of the sample on the instrument (which may also be automated), the controller may process the results of the analysis using the decoding matrix. The controller may then provide these results to a user.

VIII. Services

The methods provided herein may also be performed as a service. For example, a service provider may obtain the identity of a plurality of analytes that a customer wishes to analyze. The service provider may then encode each analyte to be detected by any of the methods described herein and provide appropriate reagents to the customer for the assay. The customer may perform the assay and provide the results to the service provider for decoding. The service provider may then provide the decoded results to the customer. The customer may also encode analytes, generate probes, and/or decode results by interacting with software installed locally (at the customer's location) or remotely (e.g., on a server reachable through a network). Exemplary customers include clinical laboratories, physicians, manufacturers of food and consumer products, industrial manufacturers (e.g., petroleum companies) and the like. A customer or party may be any suitable customer or party with a need or desire to use the methods, systems, compositions, and kits of the invention.

EXAMPLES

Example 1: General Materials & Methods

1. General Reagents

TE Buffer, pH7 (LIFE TECHNOLOGIES, Carlsbad, CA); UltraPure RNAse-free Water (LIFE TECHNOLOGIES, Carlsbad, CA); Taq 5× Master Mix (FISHER SCIENTIFIC COMPANY, Tustin, CA).

2. DNA Sequences, Primers, and Probes

Five nucleic acids from organisms of clinical relevance were chosen for the exemplary study: (1) human immunodeficiency virus 1 (HIV-1); (2) *Plasmodium falciparum* (Malaria); (3) herpes simplex virus-2 (HSV-2); (4) *Mycobacterium tuberculosis* (TB); (5) and dengue virus type 3 (dengue fever).

Two regions of diagnostic relevance from the HIV-1 genome, p17 and poly-protease, were selected from the Los Alamos National Laboratory HIV-1 reference sequence. A diagnostic sequence from the *Plasmodium falciparum* ChR7 gene was obtained from the UCSC *Plasmodium falciparum* Genome Browser. A sequence for Herpes Simplex Virus-2 was synthesized from the sequence obtained from the European Molecular Biology Library. Similarly a diagnostic sequence for the rpoB gene in *Mycobacterium tuberculosis* was synthesized from a sequence obtained from the European Molecular Biology Library. A PCR diagnostic sequence for Dengue Virus Type 3 was obtained from the National Institute of Health genetic sequence database.

Oligonucleotides were synthesized by INTEGRATED DNA TECHNOLOGIES (IDT). Probes and primer pairs were chosen for each analyte using OLIGOANALYZER, from IDT. Sense probes containing a fluorophore at the 5' end and a quencher at the 3' end were synthesized for all analytes. All oligonucleotides were lyophilized and reconstituted in TE buffer before use. Tables 9-14 show sequence information, target sequence, primers, and probes for each of the six analytes.

TABLE 9

HIV-1 polyprotease sequence information.

| | |
|---|---|
| Sequence Information | HIV-1 Poly protease 198 mer synthesized from bases 2253-2550 |
| Source | HIV-1 Reference Sequence, Los Alamos National Laboratory |
| Target sequence (3' to 5') | GGAAGCTCTATTAGATACAGGAGCAGATGATACAGTATTAGAAGAAATGA GTTTGCCAGGAAGATGGAAACCAAAAATGATAGGGGGAATTGGAGGTTTT ATCAAAGTAAGACAGTATGATCAGATACTCATAGAAATCTGTGGACATAA AGCTATAGGTACAGTATTAGTAGGACCTACACCTGTCAACATAATTGG (SEQ ID NO: 1) |
| Forward Primer (3' to 5') | GGAAGCTCTATTAGATACAGGAGCAG (SEQ ID NO: 2) |
| Reverse Prime (3' to 5') | CCAATTATGTTGACAGGTGTAGGTCC (SEQ ID NO: 3) |
| Probe 1 (3' to 5') | /56-FAM/TGAGTTTGCCAGGAAGATGGAAACCA/3BHQ_1/ (SEQ ID NO: 4) |

TABLE 10

HIV p17 sequence information.

| | |
|---|---|
| Sequence Name | HIV-1 P17 199 mer synthesized from bases 790-1186 |
| Source | HIV-1 Reference Sequence, Los Alamos National Laboratory |
| Target sequence (3' to 5') | CAGCTACAACCATCCCTTCAGACAGGATCAGAAGAACTTAGATCATTATA TAATACAGTAGCAACCCTCTATTGTGTGCATCAAAGGATAGAGATAAAAG ACACCAAGGAAGCTTTAGACAAGATAGAGGAAGAGCAAAACAAAAGTAAG AAAAAAGCACAGCAAGCAGCAGCTGACACAGGACACAGCAATCAGGTCA (SEQ ID NO: 5) |
| Forward Primer (3' to 5') | CAGCTACAACCATCCCTTCAGACA (SEQ ID NO: 6) |
| Reverse Prime (3' to 5') | TGACCTGATTGCTGTGTCCTGTGT (SEQ ID NO: 7) |
| Probe 1 (3' to 5') | /56-FAM/AGCAACCCTCTATTGTGTGCATCAAAGG/3BHQ_1 (SEQ ID NO: 8) |
| Probe 2 (3' to 5') | /5Cy3/AAAGCACAGCAAGCAGCAGCTGA/3BHQ_2/ (SEQ ID NO: 9) |

TABLE 11

*Plasmodium* ChR7 sequence information

| | |
|---|---|
| Sequence Name | *Plasmodium* ChR7 199 mer synthesized from bases 1139138-1141223 |
| Source | UCSC *Plasmodium falciparum* Genome Browser Gateway |
| Target sequence (3' to 5') | GCCTAACATGGCTATGACGGGTAACGGGGAATTAGAGTTCGATTCCGGAG AGGGAGCCTGAGAAATAGCTACCACATCTAAGGAAGGCAGCAGGCGCGTA AATTACCCAATTCTAAAGAAGAGAGGTAGTGACAAGAAATAACAATGCAA |

TABLE 11-continued

Plasmodium ChR7 sequence information

| | |
|---|---|
| | GGCCAATTTAAAACCTTCCCAGAGTAACAATTGGAGGGCAAGTCTGGTG (SEQ ID NO: 10) |
| Forward Primer (3' to 5') | GCCTAACATGGCTATGACGGGTAA (SEQ ID NO: 11) |
| Reverse Primer (3' to 5') | CACCAGACTTGCCCTCCAATTGTT (SEQ ID NO: 12) |
| Probe 1 (3' to 5') | /56-FAM/ATTCCGGAGAGGGAGCCTGAGAAATA/3BHQ_1/ (SEQ ID NO: 13) |
| Probe 2 (3' to 5') | /56-ROXN/AAGGAAGGCAGCAGGCGCGTAAATTA/3BHQ_2/ (SEQ ID NO: 14) |

15

TABLE 12

Herpes simplex virus 2 sequence information.

| | |
|---|---|
| Sequence Name | HSV-2 193 mer synthesized from HSV-2 genome |
| Source | EMBL Bank AJ303204 |
| Target sequence (3' to 5') | TCAGCCCATCCTCCTTCGGCAGTATGGAGGGTGTCGCGGCGGCGAGCCGC CGTCCCCAAAGACGTGCGGGTCGTACACGTACACGTACCAGGGCGGCGGG CCTCCGACCCGGTACGCTCTCGTAAATGCTTCCCTGCTGGTGCCGATCTG GGACCGCGCCGCGGAGACATTCGAGTACCAGATCGAACTCGG (SEQ ID NO: 15) |
| Forward Primer (3' to 5') | TCAGCCCATCCTCCTTCGGCAGTAT (SEQ ID NO: 16) |
| Reverse Primer (3' to 5') | CCGAGTTCGATCTGGTACTCGAATGT (SEQ ID NO: 17) |
| Probe 1 (3' to 5') | /56-FAM/AAAGACGTGCGGGTCGTACACGTACA/3BHQ_1/ (SEQ ID NO: 18) |
| Probe 2 (3' to 5') | /5Cy5/TAAATGCTTCCCTGCTGGTGCCGAT/3IAbRQSp/ (SEQ ID NO: 19) |

TABLE 13

Mycobacterium tuberculosis rpoB sequence information

| | |
|---|---|
| Sequence Name | Mycobacterium Tuberculosis rpoB 200 mer synthesized from Mycobacterium tuberculosis rpoB genome |
| Source | EMBL Bank GQ395623 |
| Target sequence (3' to 5') | GAGTGCAAAGACAAGGACATGACGTACGCGGCCCCGCTGTTCGTCACGGC CGAGTTCATCAACAACAACACCGGCGAGATCAAGAGCCAGACGGTGTTCA TGGGTGACTTCCCGATGATGACCGAGAAGGGCACCTTCATCATCAACGGC ACCGAGCGCGTCGTGGTCAGCCAGCTGGTCCGCTCGCCCGGTGTGTACTT (SEQ ID NO: 20) |
| Forward Primer (3' to 5') | GAGTGCAAAGACAAGGACATGACG (SEQ ID NO: 21) |
| Reverse Primer (3' to 5') | AAGTACACACCGGGCGAGC (SEQ ID NO: 22) |
| Probe 1 (3' to 5') | /56-FAM/CGCTGTTCGTCACGGCCGAGTTCAT/3BHQ_1/ (SEQ ID NO: 23) |
| Probe 2 (3' to 5') | /5Cy3/AGATCAAGAGCCAGACGGTGTTCATG/3BHQ_2/ (SEQ ID NO: 24) |
| Probe 3 (3' to 5') | /5Cy5/AAGGGCACCTTCATCATCAACGGCA/3IAbRQSp/ (SEQ ID NO: 25) |

TABLE 14

| *Dengue virus* type 3 sequence information | |
|---|---|
| Sequence Name | *Dengue Virus* Type 3 200 mer synthesized from *Dengue Virus* Type 3 genome |
| Source | GenBank M93130 |
| Target sequence (3' to 5') | ATGCCAACTGTGATTGAGCACTTAGAAAGACTACAAAGGAAACATGGAGG AATGCTTGTGAGAAATCCACTCTCACGAAACTCCACGCACGAAATGTATT GGATATCCAATGGTACAGGCAACATCGTCTCATTCACAATGACACACAGG AGACCCACCATAGAGAAAGATGTGGATTTAGGAGCAGGAACCCGACATGT (SEQ ID NO: 26) |
| Foward Primer (3' to 5') | ATGCCAACTGTGATTGAGCACT (SEQ ID NO: 27) |
| Reverse Primer (3' to 5') | ACATGTCGGGTTCCTGCTCCTAAA (SEQ ID NO: 28) |
| Probe 1 (3' to 5') | /56-FAM/ACAAAGGAAACATGGAGGAATGCTTGTGA/3BHQ_1/ (SEQ ID NO: 29) |
| Probe 2 (3' to 5') | /5Cy3/ACTCTCACGAAACTCCACGCACGAAA/3BHQ_2/ (SEQ ID NO: 30) |
| Probe 3 (3' to 5') | /56-ROXN/ACAATGACACACAGGAGACCCACCAT/3BHQ_2/ (SEQ ID NO: 31) |
| Probe 4 (3' to 5') | /5Cy5/GGATATCCAATGGTACAGGCAACATCGT/3IAbRQSp/ (SEQ ID NO: 32) |

3. Polymerase Chain Reactions

All PCR reactions were performed in a ROCHE 480 LIGHTCYCLER instrument. Forty-five thermal cycles were performed, with a 60 second hot-start at 95° C. The cycling conditions for denaturation, annealing, and extension were 45 seconds, 50 seconds, and 60 seconds at 95° C., 65° C., and 70° C., respectively. Each experiment was run in quintuplicate, with a reaction volume of 15 µL. Fluorescence measurements were obtained in the following channels after every annealing step: 483 nm to 533 nm (FAM), 523 nm to 568 nm (Cy3), 558 nm to 610 nm (ROX), and 615 nm to 670 nm (Cy5). Fluorescence measurements were also obtained after the hot-start and the end of the 45 thermal cycles. The change in the fluorescence intensity between these two measurements (after hot-start and at the end of the 45 cycles) determined the end-point fluorescent signal.

Example 2: Simultaneous Detection of Polynucleotide Markers from Pathogens Based on an Encoding Method Using More Than One Color Per Analyte This example describes the simultaneous detection of up to four polynucleotides selected from HIV (2 polynucleotides), HSV-2, *Mycobacterium, Plasmodium*, and dengue virus. Fourteen PCR reactions were assembled, using the reagents described in Table 15.

TABLE 15

Reagents for 14 PCR reactions.

| Reaction No. | Type of Reagent | Reagent | Concentration | Volume |
|---|---|---|---|---|
| 1 | | UltraPure Water | — | 34 µL |
| | | Taq 5x Master Mix | — | 42 µL |
| | Template | Poly Protease Template | 17 nM | 2 µL |
| | Primers | Poly Protease FWD Primer | 1 nM | 2 µL |
| | | Protease RVS Primer | 1 nM | 2 µL |
| | Probe | Poly Protease Probe 1 | 1 nM | 2 µL |
| 2 | | UltraPure Water | — | 28 µL |
| | | Taq 5x Master Mix | — | 42 µL |

TABLE 15-continued

Reagents for 14 PCR reactions.

| Reaction No. | Type of Reagent | Reagent | Concentration | Volume |
|---|---|---|---|---|
| | Templates | Malaria Template | 15 nM | 2 µL |
| | | Herpes Template | 17 nM | 2 µL |
| | | TB Template | 16 nM | 2 µL |
| | | Dengue Virus Template | 17 nM | 2 µL |
| | Primers | Poly Protease FWD Primer | 1 nM | 2 µL |
| | | Protease RVS Primer | 1 nM | 2 µL |
| | Probe | Poly Protease Probe 1 | 1 nM | 2 µL |
| 3 | | UltraPure Water | — | 32 µL |
| | | Taq 5x Master Mix | — | 42 µL |
| | Template | Malaria Template | 15 nM | 2 µL |
| | Primers | Malaria FWD Primer | 1 µM | 2 µL |
| | | Malaria RVS Primer | 1 µM | 2 µL |
| | Probes | Malaria Probe 1 | 1 µM | 2 µL |
| | | Malaria Probe 2 | 1 µM | 2 µL |
| 4 | | UltraPure Water | — | 26 µL |
| | | Taq 5x Master Mix | — | 42 µL |
| | Templates | Poly Protease Template | 17 nM | 2 µL |
| | | Herpes Template | 17 nM | 2 µL |
| | | TB Template | 16 nM | 2 µL |
| | | Dengue Virus Template | 17 nM | 2 µL |
| | Primers | Malaria FWD Primer | 1 µM | 2 µL |
| | | Malaria RVS Primer | 1 µM | 2 µL |
| | Probes | Malaria Probe 1 | 1 µM | 2 µL |
| | | Malaria Probe 2 | 1 µM | 2 µL |
| 5 | | UltraPure Water | — | 32 µL |
| | | Taq 5x Master Mix | — | 42 µL |
| | Template | Herpes Template | 17 nM | 2 µL |
| | Primers | Herpes FWD Primer | 1 µM | 2 µL |
| | | Herpes RVS Primer | 1 µM | 2 µL |
| | Probes | Herpes Probe 1 | 1 µM | 2 µL |
| | | Herpes Probe 2 | 1 µM | 2 µL |
| 6 | | UltraPure Water | — | 26 µL |
| | | Taq 5x Master Mix | — | 42 µL |
| | Templates | Poly Protease Template | 17 nM | 2 µL |
| | | Malaria Template | 15 nM | 2 µL |
| | | TB Template | 16 nM | 2 µL |
| | | Dengue Virus Template | 17 nM | 2 µL |
| | Primers | Herpes FWD Primer | 1 µM | 2 µL |
| | | Herpes RVS Primer | 1 µM | 2 µL |
| | Probes | Herpes Probe 1 | 1 µM | 2 µL |
| | | Herpes Probe 2 | 1 µM | 2 µL |
| 7 | | UltraPure Water | — | 30 µL |
| | | Taq 5x Master Mix | — | 42 µL |

TABLE 15-continued

Reagents for 14 PCR reactions.

| Reaction No. | Type of Reagent | Reagent | Concentration | Volume |
|---|---|---|---|---|
| | Template | TB Template | 16 nM | 2 μL |
| | Primers | TB FWD Primer | 1 μM | 2 μL |
| | | TB RVS Primer | 1 μM | 2 μL |
| | Probes | TB Probe 1 | 1 μM | 2 μL |
| | | TB Probe 2 | 1 μM | 2 μL |
| | | TB Probe 3 | 1 μM | 2 μL |
| 8 | | UltraPure Water | — | 30 μL |
| | | Taq 5x Master Mix | — | 42 μL |
| | Templates | Poly Protease Template | 17 nM | 2 μL |
| | | Malaria Template | 15 nM | 2 μL |
| | | Herpes Template | 17 nM | 2 μL |
| | | Dengue Virus Template | 17 nM | 2 μL |
| | Primers | TB FWD Primer | 1 μM | 2 μL |
| | | TB RVS Primer | 1 μM | 2 μL |
| | Probes | TB Probe 1 | 1 μM | 2 μL |
| | | TB Probe 2 | 1 μM | 2 μL |
| | | TB Probe 3 | 1 μM | 2 μL |
| 9 | | UltraPure Water | — | 28 μL |
| | | Taq 5x Master Mix | — | 42 μL |
| | Template | Dengue Virus Template | 17 nM | 2 μL |
| | Primers | Dengue Virus FWD Primer | 1 μM | 2 μL |
| | | Dengue Virus RVS Primer | 1 μM | 2 μL |
| | Probes | Dengue Virus Probe 1 | 1 μM | 2 μL |
| | | Dengue Virus Probe 2 | 1 μM | 2 μL |
| | | Dengue Virus Probe 3 | 1 μM | 2 μL |
| | | Dengue Virus Probe 4 | 1 μM | 2 μL |
| 10 | | UltraPure Water | — | 22 μL |
| | | Taq 5x Master Mix | — | 42 μL |
| | Templates | Poly Protease Template | 17 nM | 2 μL |
| | | Malaria Template | 15 nM | 2 μL |
| | | Herpes Template | 17 nM | 2 μL |
| | | TB Template | 16 nM | 2 μL |
| | Primers | Dengue Virus FWD Primer | 1 μM | 2 μL |
| | | Dengue Virus RVS Primer | 1 μM | 2 μL |
| | Probes | Dengue Virus Probe 1 | 1 μM | 2 μL |
| | | Dengue Virus Probe 2 | 1 μM | 2 μL |
| | | Dengue Virus Probe 3 | 1 μM | 2 μL |
| | | Dengue Virus Probe 4 | 1 μM | 2 μL |
| 11 | | Taq 5x Master Mix | — | 42 μL |
| | Templates | Poly Protease Template | 17 nM | 2 μL |
| | | Malaria Template | 15 nM | 2 μL |
| | | Herpes Template | 17 nM | 2 μL |
| | | Dengue Virus Template | 17 nM | 2 μL |
| | Primers | Poly Protease FWD Primer | 1 μM | 2 μL |
| | | Poly Protease RVS Primer | 1 μM | 2 μL |
| | | Malaria FWD Primer | 1 μM | 2 μL |
| | | Malaria RVS Primer | 1 μM | 2 μL |
| | | Herpes FWD Primer | 1 μM | 2 μL |
| | | Herpes RVS Primer | 1 μM | 2 μL |
| | | Dengue Virus FWD Primer | 1 μM | 2 μL |
| | | Dengue Virus RVS Primer | 1 μM | 2 μL |
| | Probes | Poly Protease Probe 1 | 1 μM | 2 μL |
| | | Malaria Probe 1 | 1 μM | 2 μL |
| | | Malaria Probe 2 | 1 μM | 2 μL |
| | | Herpes Probe 1 | 1 μM | 2 μL |
| | | Herpes Probe 2 | 1 μM | 2 μL |
| | | Dengue Virus Probe 1 | 1 μM | 2 μL |
| | | Dengue Virus Probe 2 | 1 μM | 2 μL |
| | | Dengue Virus Probe 3 | 1 μM | 2 μL |
| | | Dengue Virus Probe 4 | 1 μM | 2 μL |
| 12 | | UltraPure Water | — | 2 μL |
| | | Taq 5x Master Mix | — | 42 μL |
| | Templates | Poly Protease Template | 17 nM | 2 μL |
| | | Malaria Template | 15 nM | 2 μL |
| | | Herpes Template | 17 nM | 2 μL |
| | | TB Template | 16 nM | 2 μL |
| | Primers | Poly Protease FWD Primer | 1 μM | 2 μL |
| | | Poly Protease FWD Primer | 1 μM | 2 μL |
| | | Malaria FWD Primer | 1 μM | 2 μL |
| | | Malaria RVS Primer | 1 μM | 2 μL |
| | | Herpes FWD Primer | 1 μM | 2 μL |
| | | Herpes RVS Primer | 1 μM | 2 μL |
| | | TB FWD Primer | 1 μM | 2 μL |
| | | TB RVS Primer | 1 μM | 2 μL |
| | Probes | Poly Protease Probe 1 | 1 μM | 2 μL |
| | | Malaria Probe 1 | 1 μM | 2 μL |
| | | Malaria Probe 2 | 1 μM | 2 μL |
| | | Herpes Probe 1 | 1 μM | 2 μL |
| | | Herpes Probe 2 | 1 μM | 2 μL |
| | | TB Probe 1 | 1 μM | 2 μL |
| | | TB Probe 2 | 1 μM | 2 μL |
| | | TB Probe 3 | 1 μM | 2 μL |
| 13 | | UltraPure Water | — | 12 μL |
| | | Taq 5x Master Mix | — | 42 μL |
| | Templates | Poly Protease Template | 17 nM | 2 μL |
| | | Herpes Template | 17 nM | 2 μL |
| | | TB Template | 16 nM | 2 μL |
| | Primers | Poly Protease FWD Primer | 1 μM | 2 μL |
| | | Poly Protease FWD Primer | 1 μM | 2 μL |
| | | Herpes FWD Primer | 1 μM | 2 μL |
| | | Herpes RVS Primer | 1 μM | 2 μL |
| | | TB FWD Primer | 1 μM | 2 μL |
| | | TB RVS Primer | 1 μM | 2 μL |
| | Probes | Poly Protease Probe 1 | 1 μM | 2 μL |
| | | Herpes Probe 1 | 1 μM | 2 μL |
| | | Herpes Probe 2 | 1 μM | 2 μL |
| | | TB Probe 1 | 1 μM | 2 μL |
| | | TB Probe 2 | 1 μM | 2 μL |
| | | TB Probe 3 | 1 μM | 2 μL |
| 14 | | UltraPure Water | — | 10 μL |
| | | Taq 5x Master Mix | — | 42 μL |
| | Templates | Poly Protease Template | 17 nM | 2 μL |
| | | Malaria Template | 15 nM | 2 μL |
| | | Dengue Virus Template | 17 nM | 2 μL |
| | Primers | Poly Protease FWD Primer | 1 μM | 2 μL |
| | | Poly Protease FWD Primer | 1 μM | 2 μL |
| | | Malaria FWD Primer | 1 μM | 2 μL |
| | | Malaria RVS Primer | 1 μM | 2 μL |
| | | Dengue Virus FWD Primer | 1 μM | 2 μL |
| | | Dengue Virus RVS Primer | 1 μM | 2 μL |
| | Probes | Poly Protease Probe 1 | 1 μM | 2 μL |
| | | Malaria Probe 1 | 1 μM | 2 μL |
| | | Malaria Probe 2 | 1 μM | 2 μL |
| | | Dengue Virus Probe 1 | 1 μM | 2 μL |
| | | Dengue Virus Probe 2 | 1 μM | 2 μL |
| | | Dengue Virus Probe 3 | 1 μM | 2 μL |
| | | Dengue Virus Probe 4 | 1 μM | 2 μL |

Referring to Table 15, reactions 1, 3, 5, 7, and 9 (containing HIV polyprotease, *Plasmodium*, HSV, *Mycobacterium*, and dengue analytes, respectively) were positive controls that provided baseline fluorescence intensity for each polynucleotide analytes alone, in the absence of other analytes. The change in fluorescence intensity in each color was used to provide the expected cumulative intensity level for each color in the chromatogram (FIG. 3), as described more fully below. Reactions 2, 4, 6, 8, and 10 were negative controls used to determine the extent of non-specific amplification. In these reactions, the primers provided were not specific for the analytes provided.

Experiments 11, 12, 13, and 14 were multiplex detection experiments. Encoding was performed as indicated in Table 16. The measured fluorescence intensity for each assay, in each color, was plotted as black circles in the chromatogram of FIG. 3.

TABLE 16

Coding scheme for detection of pathogens.

| | FAM | Cy3 | ROX | Cy5 |
|---|---|---|---|---|
| HIV poly-protease | 1 | 0 | 0 | 0 |
| HIV p17 | 1 | 1 | 0 | 0 |

TABLE 16-continued

Coding scheme for detection of pathogens.

| | FAM | Cy3 | ROX | Cy5 |
|---|---|---|---|---|
| *Plasmodium* | 1 | 0 | 1 | 0 |
| HSV | 1 | 0 | 0 | 1 |
| *Mycobacterium* | 1 | 1 | 0 | 1 |
| Dengue Virus | 1 | 1 | 1 | 1 |

Figure 3:
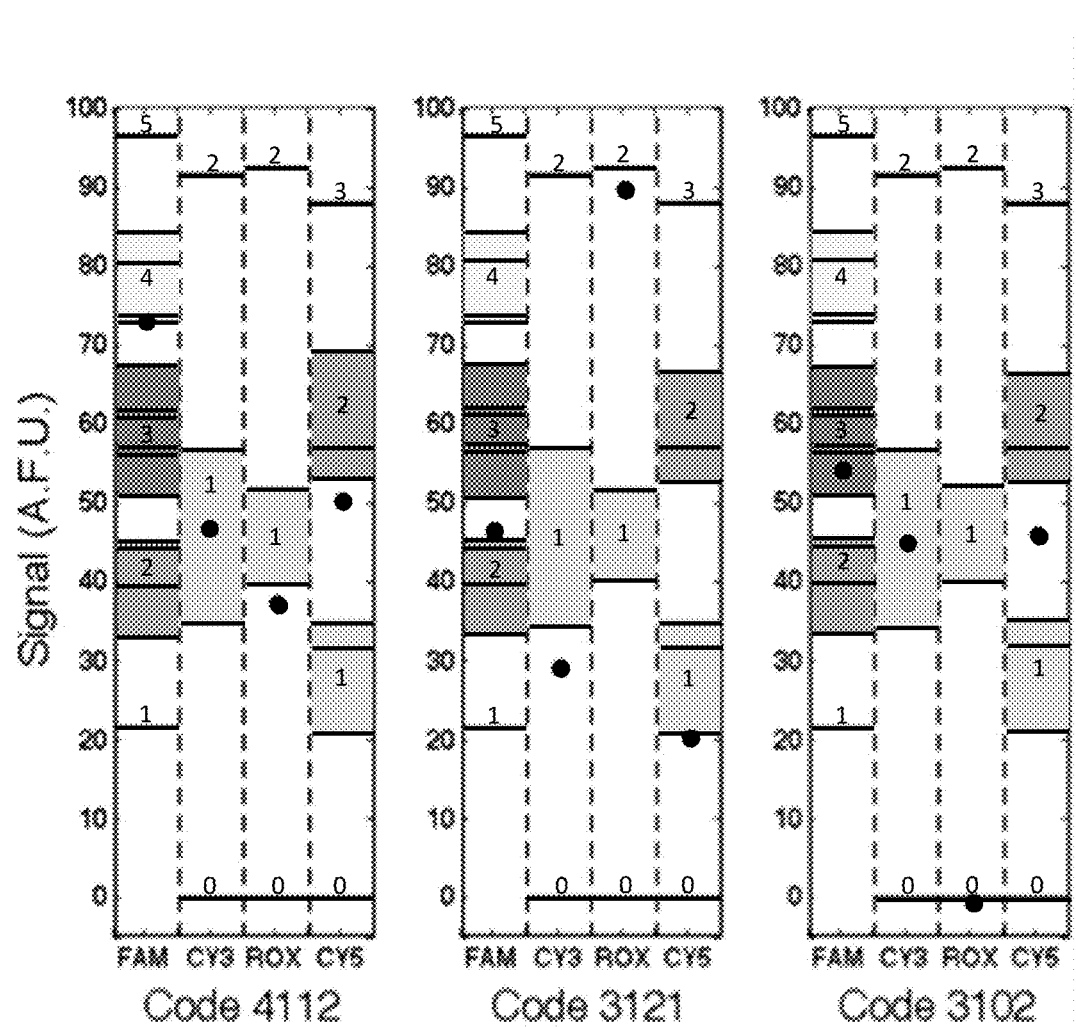
FIG. 3 shows chromatograms of experimental results obtained as described in Example 2.

To construct the chromatogram, the signals of the positive controls (reactions 1, 3, 5, 7, and 9) were used to assemble every possible combination of present sequences, in each color. The cumulative signals were plotted in a diagram, called a "chromatogram" (FIG. 3). Cumulative signals corresponding to all possible combinations of the same rank in the same color were organized into their own "band." Doing this for all four colors produced a level and band structure, against which the experimental results of each combination (reactions 11, 12, 13, and 14) could be evaluated. FIG. 3 shows three replicates of a chromatogram constructed using the positive control samples, with experimental results 4112, 3121, and 3102 superimposed on the chromatogram. The experimental results are indicated by black dots.

Figure 8:
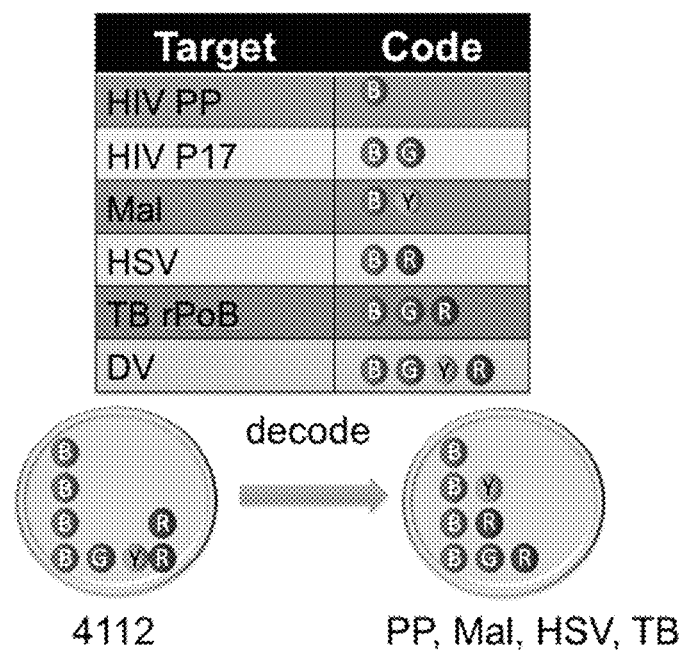
FIG. 8 shows a schematic of a legitimate result (top) and an illegitimate result (bottom).
Figure 8:
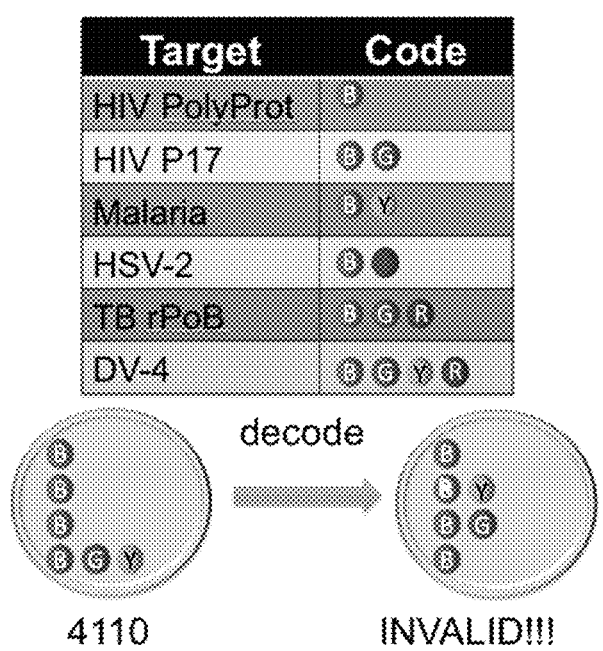

The intensity value for each color in reactions 11-14 was measure in arbitrary fluorescence units (AFU), plotted on the chromatogram, and then assigned to a band based on two criteria. First, if an experimental result was within a band, then the result was assigned to the multiplicity of the band (e.g., the Cy3 value of 1 in the left-most chromatogram of FIG. 3). Second, if an experimental result was between two bands, a two-step analysis was employed. If the experimental result was between two legitimate results, the experimental result was assigned to the closest band. (e.g., the Cy5 value of 2 in the right-most chromatogram of FIG. 3). If the experimental result was between a legitimate result and an illegitimate result, the result was assigned to the band with the legitimate result (e.g., the FAM value of 3 in the middle chromatogram of FIG. 3). FIG. 8 schematically shows a legitimate result of 4112 (top) indicating the presence of HIV polyprotease, *Plasmodium*, herpes simplex, and *Mycobacterium*; and an illegitimate result of 4110 (bottom), which cannot be decoded and indicates a malfunction in the assay.

Using these criteria, the output of Experiment 12 was designated 4112, which was the correct answer. The output of Experiment 14 could have been designated as 2121 or 3121, but 2121 is illegitimate, so the result must be 3121, which is the correct answer. The output of Experiment 13 could be designated as 3102 or 3101, both of which are legitimate, but the result is clearly closer to 2 than 1 in the Cy5 channel, so 3102, the correct answer, was designated as the result. These results provide experimental validation of the methods of the provided herein.

The results indicate a trend of slightly lower combined signal than what would be expected from a simple summation of positive-control signals. This may be because the combination of signals is not perfectly linear. This may be a result of additional effects for which the chromatogram construction does not account for at present. These effects may be related to the absolute concentration of quenchers. The higher the absolute concentration of quenchers, the larger the percentage of reaction volume they quench, so that the same percentage of released fluorophores fails to contribute as much as expected to the cumulative signal. One solution to this problem is to use low concentrations of probes, so that the percentile loss in signal is negligible, regardless of how much quencher is released.

FIG. 3 shows that each rank containing multiple combinations has a relatively wide band. The width of the band is ultimately the difference between the highest and lowest cumulative signals for the positive control samples. If all positive controls in the particular color produced exactly the same fluorescence signal, then the width of each band would be zero. Since instead those signals are somewhat different, the resulting bands are relatively wide. However, there is a simple means to tighten the bands. Instead of loading all probes at the same concentration, as was done for the experiment above, the concentration of each probe can be adjusted so that each of the resulting positive-control signals is the same as the others in the same color. This approach would significantly tighten the bands, making it easier to determine the multiplicity of a signal for a sample containing analytes.

Example 3: Simultaneous Detection of Polynucleotide Markers from Pathogens Based on an Encoding Method Using One Color Per Analyte and Different Intensities This example describes the simultaneous detection of up to three polynucleotides selected from dengue virus, HIV p17, and HIV polyprotease. The coding scheme was as depicted in Table 11. As shown in Table 17, each analyte was encoded as a single value of fluorescence intensity in a single color. In this case, as described elsewhere in this disclosure, the coding scheme is non-degenerate by design. This is achieved by assigning an intensity value to each analyte that is equal to the cumulative intensity values for the prior analytes, plus one. Of course, as described elsewhere in the specification, the initial assigned value can be greater than one, for example to better distinguish over noise. Similarly, the values assigned to each analyte can be greater than the cumulative intensity values for the prior analytes plus one, for example, to increase the separation between the intensities and enable more simple assignment of intensities.

TABLE 17

Coding scheme for detection of dengue virus, HIV polyprotease, and HIV p17.

| | FAM |
|---|---|
| Dengue Virus | 1 |
| HIV p17 | 2 |
| HIV polyprotease | 4 |

The same reagents (e.g., templates, primers, and probes) used in Example 2 were used here. The fluorescence signals generated by the respective probes in positive-control endpoint PCR reactions were measured and used to calculate the probe concentrations that would produce 1×, 2×, and 4× signal intensities. Experiments were then set up to detect the seven non-null combinations of analyte occurrences. Tables 18-24 provide the PCR reaction components for each of these mixtures.

TABLE 18

Binary FAM Experiment 1 Cocktail: HIV Polyprotease, HIV p17, and dengue virus

| Reagents | Concentration | Volume Added |
| --- | --- | --- |
| UltraPure Water | — | 50 µL |
| Taq 5x Master Mix | — | 25 µL |

| Templates | Concentration | Volume Added |
| --- | --- | --- |
| Poly Protease Template | 17 nM | 4 µL |
| P17 Template | 15 nM | 4 µL |
| Dengue Virus Template | 17 nM | 4 µL |

| Primers | Concentration | Volume Added |
| --- | --- | --- |
| Poly Protease FWD Primer | 1 µM | 4 µL |
| Poly Protease RVS Primer | 1 µM | 4 µL |
| P17 FWD Primer | 1 µM | 4 µL |
| P17 RVS Primer | 1 µM | 4 µL |
| Dengue Virus FWD Primer | 1 µM | 4 µL |
| Dengue Virus RVS Primer | 1 µM | 4 µL |

| Probes | Concentration | Volume Added |
| --- | --- | --- |
| Poly Protease Probe 1 | 800 nM | 4 µL |
| P17 Probe 1 | 400 nM | 4 µL |
| Dengue Virus Probe 1 | 200 nM | 4 µL |

TABLE 19

Binary FAM Experiment 2 Cocktail: dengue virus and HIV p17

| Reagents | Concentration | Volume Added |
| --- | --- | --- |
| UltraPure Water | — | 54 µL |
| Taq 5x Master Mix | — | 25 µL |

| Templates | Concentration | Volume Added |
| --- | --- | --- |
| Poly Protease Template | 17 nM | — |
| P17 Template | 15 nM | 4 µL |
| Dengue Virus Template | 17 nM | 4 µL |

| Primers | Concentration | Volume Added |
| --- | --- | --- |
| Poly Protease FWD Primer | 1 µM | 4 µL |
| Poly Protease RVS Primer | 1 µM | 4 µL |
| P17 FWD Primer | 1 µM | 4 µL |
| P17 RVS Primer | 1 µM | 4 µL |
| Dengue Virus FWD Primer | 1 µM | 4 µL |
| Dengue Virus RVS Primer | 1 µM | 4 µL |

| Probes | Concentration | Volume Added |
| --- | --- | --- |
| Poly Protease Probe 1 | 800 nM | 4 µL |
| P17 Probe 1 | 400 nM | 4 µL |
| Dengue Virus Probe 1 | 200 nM | 4 µL |

TABLE 20

Binary FAM Experiment 3 Cocktail: dengue virus and HIV polyprotease

| Reagents | Concentration | Volume Added |
| --- | --- | --- |
| UltraPure Water | — | 54 µL |
| Taq 5x Master Mix | — | 25 µL |

| Templates | Concentration | Volume Added |
| --- | --- | --- |
| Poly Protease Template | 17 nM | 4 µL |
| P17 Template | 15 nM | — |
| Dengue Virus Template | 17 nM | 4 µL |

| Primers | Concentration | Volume Added |
| --- | --- | --- |
| Poly Protease FWD Primer | 1 µM | 4 µL |
| Poly Protease RVS Primer | 1 µM | 4 µL |
| P17 FWD Primer | 1 µM | 4 µL |
| P17 RVS Primer | 1 µM | 4 µL |
| Dengue Virus FWD Primer | 1 µM | 4 µL |
| Dengue Virus RVS Primer | 1 µM | 4 µL |

| Probes | Concentration | Volume Added |
| --- | --- | --- |
| Poly Protease Probe 1 | 800 nM | 4 µL |
| P17 Probe 1 | 400 nM | 4 µL |
| Dengue Virus Probe 1 | 200 nM | 4 µL |

TABLE 21

Binary FAM Experiment 4 Cocktail: HIV polyprotease and HIV p17

| Reagents | Concentration | Volume Added |
| --- | --- | --- |
| UltraPure Water | — | 54 µL |
| Taq 5x Master Mix | — | 25 µL |

| Templates | Concentration | Volume Added |
| --- | --- | --- |
| Poly Protease Template | 17 nM | 4 µL |
| P17 Template | 15 nM | 4 µL |
| Dengue Virus Template | 17 nM | — |

| Primers | Concentration | Volume Added |
| --- | --- | --- |
| Poly Protease FWD Primer | 1 µM | 4 µL |
| Poly Protease RVS Primer | 1 µM | 4 µL |
| P17 FWD Primer | 1 µM | 4 µL |
| P17 RVS Primer | 1 µM | 4 µL |
| Dengue Virus FWD Primer | 1 µM | 4 µL |
| Dengue Virus RVS Primer | 1 µM | 4 µL |

| Probes | Concentration | Volume Added |
| --- | --- | --- |
| Poly Protease Probe 1 | 800 nM | 4 µL |
| P17 Probe 1 | 400 nM | 4 µL |
| Dengue Virus Probe 1 | 200 nM | 4 µL |

TABLE 22

Binary FAM Experiment 5 Cocktail: dengue virus

| Reagents | Concentration | Volume Added |
| --- | --- | --- |
| UltraPure Water | — | 58 µL |
| Taq 5x Master Mix | — | 25 µL |

| Templates | Concentration | Volume Added |
| --- | --- | --- |
| Poly Protease Template | 17 nM | — |
| P17 Template | 15 nM | — |
| Dengue Virus Template | 17 nM | 4 µL |

| Primers | Concentration | Volume Added |
| --- | --- | --- |
| Poly Protease FWD Primer | 1 µM | 4 µL |
| Poly Protease RVS Primer | 1 µM | 4 µL |
| P17 FWD Primer | 1 µM | 4 µL |
| P17 RVS Primer | 1 µM | 4 µL |
| Dengue Virus FWD Primer | 1 µM | 4 µL |
| Dengue Virus RVS Primer | 1 µM | 4 µL |

TABLE 22-continued

Binary FAM Experiment 5 Cocktail: dengue virus

| Probes | Concentration | Volume Added |
|---|---|---|
| Poly Protease Probe 1 | 800 nM | 4 μL |
| P17 Probe 1 | 400 nM | 4 μL |
| Dengue Virus Probe 1 | 200 nM | 4 μL |

TABLE 23

Binary FAM Experiment 6 Cocktail: HIV p17

| Reagents | Concentration | Volume Added |
|---|---|---|
| UltraPure Water | — | 58 μL |
| Taq 5x Master Mix | — | 25 μL |

| Templates | Concentration | Volume Added |
|---|---|---|
| Poly Protease Template | 17 nM | — |
| P17 Template | 15 nM | 4 μL |
| Dengue Virus Template | 17 nM | — |

| Primers | Concentration | Volume Added |
|---|---|---|
| Poly Protease FWD Primer | 1 μM | 4 μL |
| Poly Protease RVS Primer | 1 μM | 4 μL |
| P17 FWD Primer | 1 μM | 4 μL |
| P17 RVS Primer | 1 μM | 4 μL |
| Dengue Virus FWD Primer | 1 μM | 4 μL |
| Dengue Virus RVS Primer | 1 μM | 4 μL |

| Probes | Concentration | Volume Added |
|---|---|---|
| Poly Protease Probe 1 | 800 nM | 4 μL |
| P17 Probe 1 | 400 nM | 4 μL |
| Dengue Virus Probe 1 | 200 nM | 4 μL |

TABLE 24

Binary FAM Experiment 7 Cocktail: HIV polyprotease

| Reagents | Concentration | Volume Added |
|---|---|---|
| UltraPure Water | — | 58 μL |
| Taq 5x Master Mix | — | 25 μL |

| Templates | Concentration | Volume Added |
|---|---|---|
| Poly Protease Template | 17 nM | 4 μL |
| P17 Template | 15 nM | — |
| Dengue Virus Template | 17 nM | — |

| Primers | Concentration | Volume Added |
|---|---|---|
| Poly Protease FWD Primer | 1 μM | 4 μL |
| Poly Protease RVS Primer | 1 μM | 4 μL |
| P17 FWD Primer | 1 μM | 4 μL |
| P17 RVS Primer | 1 μM | 4 μL |
| Dengue Virus FWD Primer | 1 μM | 4 μL |
| Dengue Virus RVS Primer | 1 μM | 4 μL |

| Probes | Concentration | Volume Added |
|---|---|---|
| Poly Protease Probe 1 | 800 nM | 4 μL |
| P17 Probe 1 | 400 nM | 4 μL |
| Dengue Virus Probe 1 | 200 nM | 4 μL |

The total fluorescence signal of each experiment was plotted on a chromatogram (FIG. 7) that was constructed as described above. The width of the bands around each positive control measurement is the propagated uncertainty of the 1× measurement. That uncertainty was equated to the standard deviation of the fluorescence signals of the last five PCR cycles in saturation.

Figure 7:
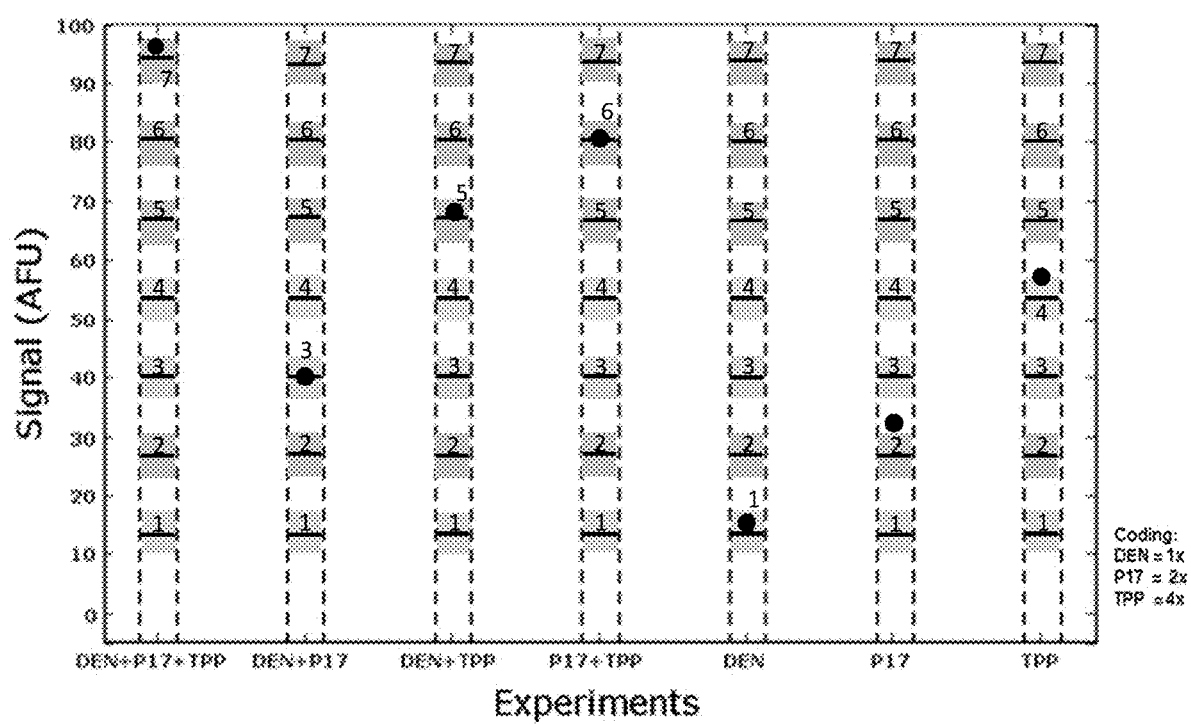
FIG. 7 shows chromatograms of experimental results obtained as described in Example 3.

FIG. 7 shows the results of this experiment. The three right-most results show the measured intensities for dengue virus alone (DEN), HIV p17 alone (P17), and HIV polyprotease (TPP). The assigned intensities for each of these analytes were as indicated in Table 11, and FIG. 7 confirms that the three analytes yielded the expected intensity results when alone (see DEN, P17, and TPP). At the end of the assay, essentially all of the probes have been hydrolyzed, releasing essentially all of the fluorophores, which emit a signal. A fixed amount of a fluorophore produces a fixed and predictable amount of signal. Therefore a target that is present should generally produce a fixed amount of signal, as determined by the amount of probe added to the reaction volume.

As expected, the intensity values for the combinations of analytes are equivalent to the sum of the assigned intensities. Since this coding scheme is designed to be non-degenerate, each result can be unambiguously decoded into the presence or absence of a particular analyte. For example, starting from the left side of FIG. 7, a result of 7 indicates the presence of all three analytes. A result of 3 indicates the presence of dengue virus and HIV p17 analytes, and the absence of HIV polyprotease. A result of 5 indicates the presence of dengue virus and HIV polyprotease, and the absence of HIV p17. Finally a result of 6 indicates the presence of HIV p17 and HIV polyprotease, and the absence of dengue virus. This coding scheme can be extended to encode additional analytes, as described elsewhere in this disclosure.

What is claimed is:

1. An assay that is capable of unambiguously detecting the presence or absence of each of at least M analytes,
 wherein each of said at least M analytes is encoded as a value of one component of a fluorescent signal, thereby generating a coding scheme,
 wherein said fluorescent signal comprises F wavelength components, and
 wherein said assay is capable of unambiguously detecting the presence or absence of each of said at least M analytes, in any combination of presence or absence, in a single sample volume, based on detection of said F wavelength components, when M is greater than F,
 wherein the assay does not require the use of mass spectrometry or immobilization of said at least M analytes, and
 wherein the analytes are amplified in the single sample volume.

2. The assay of claim 1, wherein each of said at least M analytes is encoded as at least one first value in a first component of said fluorescent signal and at least one second value in a second component of said fluorescent signal.

3. The assay of claim 2, wherein said first value is an intensity or range of intensities.

4. The assay of claim 2, wherein said coding scheme is made nondegenerate by enumerating every legitimate result that can be obtained from said coding scheme, identifying each legitimate result that is degenerate, and eliminating at least one potential analyte code from said coding scheme to eliminate degeneracy.

5. The assay of claim 1, wherein said detecting is performed with reagents comprising hybridization probes.

6. The assay of claim 5, wherein said hybridization probes comprise one or more hybridization probes specific for different analytes and comprising an identical fluorophore or combination of fluorophores.

7. The assay of claim 5, wherein said fluorescence signal from said hybridization probes are used to construct a chromatogram.

8. The assay of claim 1, wherein said signal is generated during a polymerase chain reaction.

9. The assay of claim 1, wherein at least one of said analytes is encoded by at least one additional value, wherein said at least one additional value is selected from the group consisting of a value from at least one additional component of said signal, a value from at least one component of an additional signal, and combinations thereof.

10. The assay of claim 1, wherein at least one of said analytes comprises a polynucleotide.

11. The assay of claim 1, further comprising transmitting information concerning the presence or absence of at least one of said analytes through a computer network.

12. The assay of claim 1, wherein at least one step of said assay is performed using a computer and wherein said computer is connected to a thermal cycler.

13. The assay of claim 1, wherein said coding scheme is innately nondegenerate or non-degenerate by construction.

14. A kit for detecting the presence or absence of at least M analytes by generating a single cumulative measurement, comprising analyte-specific reagents, wherein:
 a. each of said at least M analytes is encoded as a value of one component of a fluorescent signal, thereby generating a coding scheme, wherein each of said at least M analytes is represented in said coding scheme by said value, and wherein said encoding is performed in a manner that eliminates degeneracy; and
 b. each of said analyte-specific reagents, when contacted with a sample comprising its corresponding analyte, generates the value;
 wherein said kit is capable of unambiguously detecting the presence or absence of each analyte of M analytes in a single sample volume, in any combination of presence or absence, and wherein the kit does not require the use of mass spectrometry or immobilization of said M analytes, and
 wherein the analytes are simplified in the single sample volume.

15. The kit of claim 14, wherein said fluorescent signal comprises F wavelength components and said kit is capable of unambiguously detecting the presence or absence of M analytes, in any combination of presence or absence, when M is greater than F.

16. The kit of claim 14, wherein said analyte-specific reagents comprise a plurality of hybridization probes.

17. The kit of claim 16, wherein said plurality of hybridization probes comprise a fluorophore, and wherein said plurality of hybridization probes are specific for different analytes.

18. The kit of claim 17, wherein said number of hybridization probes in the kit is greater than M.

19. The kit of claim 14, wherein the analyte-specific reagents are each present at a different amount in the kit.

* * * * *

SEQUENCE LISTING

<160> NUMBER OF SEQ ID NOS: 32

<210> SEQ ID NO 1
<211> LENGTH: 198
<212> TYPE: DNA
<213> ORGANISM: Human immunodeficiency virus 1

<400> SEQUENCE: 1

```
ggaagctcta ttagatacag gagcagatga tacagtatta gaagaaatga gtttgccagg      60
aagatggaaa ccaaaaatga tagggggaat tggaggtttt atcaaagtaa gacagtatga    120
tcagatactc atagaaatct gtggacataa agctataggt acagtattag taggacctac    180
```

```
acctgtcaac ataattgg                                                   198

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggaagctcta ttagatacag gagcag                                           26

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccaattatgt tgacaggtgt aggtcc                                           26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'6-FAM
<220> FEATURE:
<223> OTHER INFORMATION: 3'BHQ_1

<400> SEQUENCE: 4
tgagtttgcc aggaagatgg aaacca                                           26

<210> SEQ ID NO 5
<211> LENGTH: 199
<212> TYPE: DNA
<213> ORGANISM: Human immunodeficiency virus 1

<400> SEQUENCE: 5
cagctacaac catcccttca gacaggatca gaagaactta gatcattata taatacagta      60
gcaaccctct attgtgtgca tcaaaggata gagataaaag acaccaagga agctttagac     120
aagatagagg aagagcaaaa caaaagtaag aaaaaagcac agcaagcagc agctgacaca     180
ggacacagca atcaggtca                                                  199

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagctacaac catcccttca gaca                                             24

<210> SEQ ID NO 7
<211> LENGTH: 24
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 7
tgacctgatt gctgtgtcct gtgt                                           24

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'6-FAM
<220> FEATURE:
<223> OTHER INFORMATION: 3'BHQ_1

<400> SEQUENCE: 8
agcaaccctc tattgtgtgc atcaaagg                                       28

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'Cy3
<220> FEATURE:
<223> OTHER INFORMATION: 3'BHQ_2

<400> SEQUENCE: 9
aaagcacagc aagcagcagc tga                                            23

<210> SEQ ID NO 10
<211> LENGTH: 199
<212> TYPE: DNA
<213> ORGANISM: Plasmodium falciparum

<400> SEQUENCE: 10
gcctaacatg gctatgacgg gtaacgggga attagagttc gattccggag agggagcctg    60
agaaatagct accacatcta aggaaggcag caggcgcgta aattacccaa ttctaaagaa    120
gagaggtagt gacaagaaat aacaatgcaa ggccaattta aaaccttccc agagtaacaa   180
ttggagggca agtctggtg                                                199

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcctaacatg gctatgacgg gtaa                                           24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 12
caccagactt gccctccaat tgtt                                          24

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'6-FAM
<220> FEATURE:
<223> OTHER INFORMATION: 3'BHQ_1

<400> SEQUENCE: 13
attccggaga gggagcctga gaaata                                        26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'6-ROXN
<220> FEATURE:
<223> OTHER INFORMATION: 3'BHQ_2

<400> SEQUENCE: 14
aaggaaggca gcaggcgcgt aaatta                                        26

<210> SEQ ID NO 15
<211> LENGTH: 192
<212> TYPE: DNA
<213> ORGANISM: Herpes simplex virus 2

<400> SEQUENCE: 15
tcagcccatc ctccttcggc agtatggagg gtgtcgcggc ggcgagccgc cgtccccaaa    60
gacgtgcggg tcgtacacgt acacgtacca gggcggcggg cctccgaccc ggtacgctct   120
cgtaaatgct tccctgctgg tgccgatctg ggaccgcgcc gcggagacat tcgagtacca   180
gatcgaactc gg                                                      192

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcagcccatc ctccttcggc agtat                                         25

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccgagttcga tctggtactc gaatgt                                            26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'6-FAM
<220> FEATURE:
<223> OTHER INFORMATION: 3'BHQ_1

<400> SEQUENCE: 18
aaagacgtgc gggtcgtaca cgtaca                                            26

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'Cy5
<220> FEATURE:
<223> OTHER INFORMATION: 3'3IAbRQSp

<400> SEQUENCE: 19
taaatgcttc cctgctggtg ccgat                                             25

<210> SEQ ID NO 20
<211> LENGTH: 200
<212> TYPE: DNA
<213> ORGANISM: Mycobacterium tuberculosis

<400> SEQUENCE: 20
gagtgcaaag acaaggacat gacgtacgcg gccccgctgt tcgtcacggc cgagttcatc        60
aacaacaaca ccggcgagat caagagccag acggtgttca tgggtgactt cccgatgatg      120
accgagaagg gcaccttcat catcaacggc accgagcgcg tcgtggtcag ccagctggtc      180
cgctcgcccg gtgtgtactt                                                  200

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gagtgcaaag acaaggacat gacg                                              24

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aagtacacac cgggcgagc                                                    19

```
<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'6-FAM
<220> FEATURE:
<223> OTHER INFORMATION: 3'BHQ_1

<400> SEQUENCE: 23
cgctgttcgt cacggccgag ttcat                                            25

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'Cy3
<220> FEATURE:
<223> OTHER INFORMATION: 3'BHQ_2

<400> SEQUENCE: 24
agatcaagag ccagacggtg ttcatg                                           26

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'Cy5
<220> FEATURE:
<223> OTHER INFORMATION: 3'IAbRQSp

<400> SEQUENCE: 25
aagggcacct tcatcatcaa cggca                                            25

<210> SEQ ID NO 26
<211> LENGTH: 200
<212> TYPE: DNA
<213> ORGANISM: Dengue virus 3

<400> SEQUENCE: 26
atgccaactg tgattgagca cttagaaaga ctacaaagga acatggagg aatgcttgtg       60 agaaatccac tctcacgaaa ctccacgcac gaaatgtatt ggatatccaa tggtacaggc     120
aacatcgtct cattcacaat gacacacagg agacccacca tagagaaaga tgtggattta     180
ggagcaggaa cccgacatgt                                                 200

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgccaactg tgattgagca ct                                               22
```

```
<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acatgtcggg ttcctgctcc taaa                                              24

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'6-FAM
<220> FEATURE:
<223> OTHER INFORMATION: 3'BHQ_1

<400> SEQUENCE: 29
acaaaggaaa catggaggaa tgcttgtga                                         29

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'Cy3
<220> FEATURE:
<223> OTHER INFORMATION: 3'BHQ_2

<400> SEQUENCE: 30
actctcacga aactccacgc acgaaa                                            26

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'6-ROXN
<220> FEATURE:
<223> OTHER INFORMATION: 3'BHQ_2

<400> SEQUENCE: 31
acaatgacac acaggagacc caccat                                            26

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'Cy5
<220> FEATURE:
<223> OTHER INFORMATION: 3'IAbRQSp
```

```
<400> SEQUENCE: 32
ggatatccaa tggtacaggc aacatcgt                                          28
```